US012544309B2

(12) United States Patent
Fangrow

(10) Patent No.: US 12,544,309 B2
(45) Date of Patent: *Feb. 10, 2026

(54) PRESSURE-REGULATING VIAL ADAPTORS

(71) Applicant: ICU Medical, Inc., San Clemente, CA (US)

(72) Inventor: Thomas F. Fangrow, Mission Viejo, CA (US)

(73) Assignee: ICU MEDICAL, INC., San Clemente, CA (US)

( * ) Notice: Subject to any disclaimer, the term of this patent is extended or adjusted under 35 U.S.C. 154(b) by 520 days.

This patent is subject to a terminal disclaimer.

(21) Appl. No.: 18/066,506

(22) Filed: Dec. 15, 2022

(65) Prior Publication Data

US 2023/0225943 A1 Jul. 20, 2023

Related U.S. Application Data

(63) Continuation of application No. 16/415,765, filed on May 17, 2019, now Pat. No. 11,529,289, which is a (Continued)

(51) Int. Cl.

*A61J 1/20* (2006.01)
*A61J 1/14* (2023.01)
*A61M 5/32* (2006.01)

(52) U.S. Cl.

CPC .......... *A61J 1/2072* (2015.05); *A61J 1/1406* (2013.01); *A61J 1/201* (2015.05); *A61J 1/2037* (2015.05);

(Continued)

(58) Field of Classification Search

CPC ........ A61J 1/2072; A61J 1/2075; A61J 1/201; A61J 1/2037; A61J 1/2048; A61J 1/2082;

(Continued)

(56) References Cited

U.S. PATENT DOCUMENTS

| | | | |
|---|---|---|---|
| 2,074,223 | A | 3/1937 | Horiuchi et al. |
| 2,409,734 | A | 10/1946 | Bucher et al. |

(Continued)

FOREIGN PATENT DOCUMENTS

| | | | |
|---|---|---|---|
| AU | 2013200393 A1 | 2/2013 |
| CA | 1037428 | 8/1978 |

(Continued)

OTHER PUBLICATIONS

European Opposition, re EP Application No. 12823375.6, dated Jul. 24, 2023.

(Continued)

*Primary Examiner* — Philip R Wiest

(74) *Attorney, Agent, or Firm* — Knobbe, Martens, Olson & Bear, LLP

(57) ABSTRACT

A vial adaptor can include a connector interface and/or a piercing member. The vial adaptor can include a regulator assembly. The regulator assembly can include a regulator base, a regulator nest coupled with the regulator base, and/or a storage chamber formed at least partially by one or both of the regulator base and regulator nest. The regulator assembly can include a cover connected to one or both of the regulator base and regulator nest and fitted around a radially outward portion of one or both of the regulator base and regulator nest. In some cases, the regular assembly includes a flexible enclosure connected to the regulator nest and configured to transition between a contracted configuration and an expanded configuration. In some cases, the flexible enclosure is inhibited from transitioning to the expanded configuration prior to removal or modification of the cover from the regulator assembly.

17 Claims, 36 Drawing Sheets

Related U.S. Application Data continuation of application No. 16/073,715, filed as application No. PCT/US2017/015468 on Jan. 27, 2017, now Pat. No. 10,292,904.

(60) Provisional application No. 62/288,950, filed on Jan. 29, 2016.

(52) U.S. Cl.
CPC .......... *A61J 1/2048* (2015.05); *A61J 1/2082* (2015.05); *A61J 1/2096* (2013.01); *A61M 5/32* (2013.01); *A61J 1/1456* (2015.05)

(58) Field of Classification Search
CPC ...... A61J 1/1406; A61J 1/2096; A61J 1/1456; A61M 5/32
See application file for complete search history.

(56) References Cited

U.S. PATENT DOCUMENTS

| | | | |
|---|---|---|---|
| 2,419,401 | A | 4/1947 | Hinds |
| 2,668,533 | A | 2/1954 | Evans |
| 2,673,013 | A | 3/1954 | Hester |
| 2,793,758 | A | 5/1957 | Billingsley et al. |
| 2,852,024 | A | 9/1958 | Ryan |
| 2,999,499 | A | 9/1961 | Willet |
| 2,999,500 | A | 9/1961 | Schurer |
| 3,291,151 | A | 12/1966 | Loken |
| RE26,488 | E | 11/1968 | Bull |
| 3,542,240 | A | 11/1970 | Solowey |
| 3,557,778 | A | 1/1971 | Hughes |
| 3,584,770 | A | 6/1971 | Taylor |
| 3,797,521 | A | 3/1974 | King |
| 3,822,700 | A | 7/1974 | Pennington |
| 3,844,283 | A | 10/1974 | Dabney |
| 3,853,157 | A | 12/1974 | Madaio |
| 3,882,909 | A | 5/1975 | Ogle |
| 3,923,058 | A | 12/1975 | Weingarten |
| 3,938,520 | A | 2/1976 | Scislowcz et al. |
| 3,940,003 | A | 2/1976 | Larson |
| 3,941,167 | A | 3/1976 | Haury-Wirtz et al. |
| 3,957,082 | A | 5/1976 | Fuson et al. |
| 3,980,082 | A | 9/1976 | Miller |
| 3,993,063 | A | 11/1976 | Larrabee |
| 4,046,291 | A | 9/1977 | Goda |
| 4,058,121 | A | 11/1977 | Choski et al. |
| 4,143,853 | A | 3/1979 | Abramson |
| 4,207,923 | A | 6/1980 | Giurtino |
| 4,219,021 | A | 8/1980 | Fink |
| 4,240,433 | A | 12/1980 | Bordow |
| 4,240,833 | A | 12/1980 | Myles |
| 4,253,459 | A | 3/1981 | Willis |
| 4,262,671 | A | 4/1981 | Kersten |
| 4,286,640 | A | 9/1981 | Knox et al. |
| 4,301,799 | A | 11/1981 | Pope, Jr. et al. |
| 4,312,349 | A | 1/1982 | Cohen |
| 4,314,586 | A | 2/1982 | Folkman |
| 4,334,551 | A | 6/1982 | Pfister |
| 4,349,035 | A | 9/1982 | Thomas et al. |
| 4,376,634 | A | 3/1983 | Prior et al. |
| 4,381,776 | A | 5/1983 | Latham, Jr. |
| 4,396,016 | A | 8/1983 | Becker |
| 4,410,321 | A | 10/1983 | Pearson et al. |
| 4,458,733 | A | 7/1984 | Lyons |
| 4,475,915 | A | 10/1984 | Sloane |
| 4,493,348 | A | 1/1985 | Lemmons |
| 4,505,709 | A | 3/1985 | Froning et al. |
| 4,534,758 | A | 8/1985 | Akers et al. |
| 4,564,054 | A | 1/1986 | Gustavsson |
| 4,573,993 | A | 3/1986 | Hoag et al. |
| 4,576,211 | A | 3/1986 | Valentini et al. |
| 4,588,403 | A | 5/1986 | Weiss et al. |
| 4,600,040 | A | 7/1986 | Naslund |
| 4,645,073 | A | 2/1987 | Homan |
| 4,673,404 | A | 6/1987 | Gustavsson |
| 4,730,635 | A | 3/1988 | Linden |
| 4,735,608 | A | 4/1988 | Sardam |
| 4,743,243 | A | 5/1988 | Vaillancourt |
| 4,768,568 | A | 9/1988 | Fournier et al. |
| 4,785,859 | A | 11/1988 | Gustavsson et al. |
| 4,798,578 | A | 1/1989 | Ranford |
| 4,857,068 | A | 8/1989 | Kahn |
| 4,929,230 | A | 5/1990 | Pfleger |
| 4,981,464 | A | 1/1991 | Suzuki |
| 5,006,114 | A | 4/1991 | Rogers |
| 5,060,704 | A | 10/1991 | Rohrbough |
| 5,104,379 | A | 4/1992 | Nakamura et al. |
| 5,169,393 | A | 12/1992 | Moorehead et al. |
| 5,176,673 | A | 1/1993 | Marrucchi |
| 5,334,163 | A | 8/1994 | Sinnett |
| 5,349,984 | A | 9/1994 | Weinheimer et al. |
| 5,405,331 | A | 4/1995 | Behnke et al. |
| 5,445,630 | A | 8/1995 | Richmond |
| 5,478,337 | A | 12/1995 | Okamoto et al. |
| 5,580,351 | A | 12/1996 | Helgren et al. |
| 5,660,796 | A | 8/1997 | Sheehy |
| 5,685,866 | A | 11/1997 | Lopez |
| 5,700,245 | A | 12/1997 | Sancoff et al. |
| 5,725,500 | A | 3/1998 | Micheler |
| 5,749,394 | A | 5/1998 | Boehmer et al. |
| 5,766,147 | A | 6/1998 | Sancoff et al. |
| 5,772,079 | A | 6/1998 | Gueret |
| 5,776,125 | A | 7/1998 | Dudar et al. |
| 5,803,311 | A | 9/1998 | Fuchs |
| 5,833,213 | A | 11/1998 | Ryan |
| 5,890,610 | A | 4/1999 | Jansen et al. |
| 6,003,553 | A | 12/1999 | Wahlberg |
| 6,013,051 | A | 1/2000 | Nelson |
| 6,071,270 | A | 6/2000 | Fowles et al. |
| 6,139,534 | A | 10/2000 | Niedospial et al. |
| 6,159,192 | A | 12/2000 | Fowles et al. |
| 6,221,041 | B1 | 4/2001 | Russo |
| 6,238,372 | B1 | 5/2001 | Zinger et al. |
| 6,358,236 | B1 | 3/2002 | DeFoggi et al. |
| 6,457,488 | B2 | 10/2002 | Loo |
| 6,478,788 | B1 | 11/2002 | Aneas |
| 6,503,240 | B1 | 1/2003 | Niedospial, Jr. et al. |
| 6,544,246 | B1 | 4/2003 | Niedospial, Jr. |
| 6,551,299 | B2 | 4/2003 | Miyoshi et al. |
| 6,572,256 | B2 | 6/2003 | Seaton et al. |
| 6,679,290 | B2 | 1/2004 | Matthews et al. |
| 6,692,478 | B1 | 2/2004 | Paradis |
| 6,715,520 | B2 | 4/2004 | Andreasson et al. |
| 6,719,719 | B2 | 4/2004 | Carmel et al. |
| 6,890,328 | B2 | 5/2005 | Fowles et al. |
| 6,989,002 | B2 | 1/2006 | Guala |
| 6,997,910 | B2 | 2/2006 | Howlett et al. |
| 6,997,917 | B2 | 2/2006 | Niedospial, Jr. et al. |
| 7,004,926 | B2 | 2/2006 | Navia et al. |
| 7,048,720 | B1 | 5/2006 | Thorne, Jr. et al. |
| 7,086,431 | B2 | 8/2006 | D'Antonio et al. |
| 7,101,354 | B2 | 9/2006 | Thorne, Jr. et al. |
| 7,140,401 | B2 | 11/2006 | Wilcox et al. |
| 7,192,423 | B2 | 3/2007 | Wong |
| 7,213,702 | B2 | 5/2007 | Takimoto et al. |
| 7,291,131 | B2 | 11/2007 | Call |
| 7,306,584 | B2 | 12/2007 | Wessman et al. |
| 7,354,427 | B2 | 4/2008 | Fangrow |
| 7,507,227 | B2 | 3/2009 | Fangrow |
| 7,510,547 | B2 | 3/2009 | Fangrow |
| 7,510,548 | B2 | 3/2009 | Fangrow |
| 7,513,895 | B2 | 4/2009 | Fangrow |
| 7,534,238 | B2 | 5/2009 | Fangrow |
| 7,547,300 | B2 | 6/2009 | Fangrow |
| 7,569,043 | B2 | 8/2009 | Fangrow |
| 7,618,408 | B2 | 11/2009 | Yandell |
| 7,632,261 | B2 | 12/2009 | Zinger et al. |
| 7,645,271 | B2 | 1/2010 | Fangrow |
| 7,654,995 | B2 | 2/2010 | Warren et al. |
| 7,658,733 | B2 | 2/2010 | Fangrow |
| 7,678,333 | B2 | 3/2010 | Reynolds et al. |
| 7,703,486 | B2 | 4/2010 | Costanzo |
| 7,731,678 | B2 | 6/2010 | Tennican et al. |

(56) References Cited

U.S. PATENT DOCUMENTS

| | | | |
|---|---|---|---|
| 7,743,799 | B2 | 6/2010 | Mosler et al. |
| 7,744,580 | B2 | 6/2010 | Reboul |
| 7,758,560 | B2 | 7/2010 | Connell et al. |
| 7,789,871 | B1 | 9/2010 | Yandell |
| D630,732 | S | 1/2011 | Lev et al. |
| 7,862,537 | B2 | 1/2011 | Zinger et al. |
| 7,879,018 | B2 | 2/2011 | Zinger et al. |
| 7,883,499 | B2 | 2/2011 | Fangrow |
| 7,887,528 | B2 | 2/2011 | Yandell |
| 7,900,659 | B2 | 3/2011 | Whitley et al. |
| D637,713 | S | 5/2011 | Nord et al. |
| 7,963,954 | B2 | 6/2011 | Kavazov |
| D641,080 | S | 7/2011 | Zinger et al. |
| 7,972,321 | B2 | 7/2011 | Fangrow |
| 7,981,089 | B2 | 7/2011 | Weilbacher |
| 7,981,101 | B2 | 7/2011 | Walsh |
| 7,998,106 | B2 | 8/2011 | Thorne, Jr. et al. |
| 8,021,325 | B2 | 9/2011 | Zinger et al. |
| 8,025,653 | B2 | 9/2011 | Capitqaine et al. |
| 8,029,747 | B2 | 10/2011 | Helmerson |
| 8,074,964 | B2 | 12/2011 | Mansour et al. |
| 8,100,154 | B2 | 1/2012 | Reynolds et al. |
| 8,109,285 | B2 | 2/2012 | Ehrman et al. |
| 8,122,923 | B2 | 2/2012 | Kraus et al. |
| 8,123,736 | B2 | 2/2012 | Kraushaar et al. |
| 8,141,601 | B2 | 3/2012 | Fehr et al. |
| 8,156,971 | B2 | 4/2012 | Costanzo |
| 8,162,006 | B2 | 4/2012 | Guala |
| 8,162,013 | B2 | 4/2012 | Rosenquist et al. |
| 8,162,914 | B2 | 4/2012 | Kraushaar et al. |
| 8,167,863 | B2 | 5/2012 | Yow |
| 8,167,864 | B2 | 5/2012 | Browne |
| 8,172,794 | B2 | 5/2012 | Lum et al. |
| 8,172,825 | B2 | 5/2012 | Solomon et al. |
| 8,177,768 | B2 | 5/2012 | Leinsing |
| 8,196,614 | B2 | 6/2012 | Kriheli |
| 8,197,459 | B2 | 6/2012 | Jansen et al. |
| 8,206,367 | B2 | 6/2012 | Warren et al. |
| 8,211,082 | B2 | 7/2012 | Hasegawa et al. |
| 8,221,382 | B2 | 7/2012 | Moy et al. |
| 8,225,826 | B2 | 7/2012 | Horppu et al. |
| 8,231,567 | B2 | 7/2012 | Tennican et al. |
| 8,241,265 | B2 | 8/2012 | Moy et al. |
| 8,262,643 | B2 | 9/2012 | Tennican |
| 8,267,127 | B2 | 9/2012 | Kriheli |
| 8,267,913 | B2 | 9/2012 | Fangrow |
| 8,281,807 | B2 | 10/2012 | Trombley, III et al. |
| 8,286,936 | B2 | 10/2012 | Kitani et al. |
| 8,287,513 | B2 | 10/2012 | Ellstrom et al. |
| 8,317,741 | B2 | 11/2012 | Kraushaar |
| 8,336,587 | B2 | 12/2012 | Rosenquist et al. |
| 8,356,644 | B2 | 1/2013 | Chong et al. |
| 8,356,645 | B2 | 1/2013 | Chong et al. |
| 8,357,137 | B2 | 1/2013 | Yandell |
| 8,381,776 | B2 | 2/2013 | Horppu |
| 8,403,905 | B2 | 3/2013 | Yow |
| 8,409,164 | B2 | 4/2013 | Fangrow |
| 8,409,165 | B2 | 4/2013 | Niedospial et al. |
| 8,414,554 | B2 | 4/2013 | Garfield et al. |
| 8,414,555 | B2 | 4/2013 | Garfield et al. |
| 8,425,487 | B2 | 4/2013 | Beiriger et al. |
| 8,449,521 | B2 | 5/2013 | Thorne, Jr. et al. |
| 8,454,579 | B2 | 6/2013 | Fangrow, Jr. |
| 8,469,939 | B2 | 6/2013 | Fangrow |
| 8,506,548 | B2 | 8/2013 | Okiyama |
| 8,511,352 | B2 | 8/2013 | Kraus et al. |
| 8,512,307 | B2 | 8/2013 | Fangrow |
| 8,522,832 | B2 | 9/2013 | Lopez et al. |
| 8,523,838 | B2 | 9/2013 | Tornqvist |
| 8,540,692 | B2 | 9/2013 | Fangrow |
| 8,602,067 | B2 | 12/2013 | Kuhni et al. |
| 8,608,723 | B2 | 12/2013 | Lev et al. |
| 8,622,985 | B2 | 1/2014 | Ellstrom |
| 8,641,656 | B2 | 2/2014 | Bene |
| 8,657,803 | B2 | 2/2014 | Helmerson et al. |
| 8,667,996 | B2 | 3/2014 | Gonnelli et al. |
| 8,684,992 | B2 | 4/2014 | Sullivan et al. |
| 8,684,994 | B2 | 4/2014 | Lev et al. |
| 8,701,696 | B2 | 4/2014 | Guala |
| 8,702,675 | B2 | 4/2014 | Imai |
| 8,720,496 | B2 | 5/2014 | Huwiler et al. |
| 8,721,614 | B2 | 5/2014 | Takemoto |
| 8,753,325 | B2 | 6/2014 | Lev et al. |
| 8,795,231 | B2 | 8/2014 | Chong et al. |
| 8,801,678 | B2 | 8/2014 | Panian et al. |
| 8,821,436 | B2 | 9/2014 | Mosler et al. |
| 8,827,977 | B2 | 9/2014 | Fangrow |
| 8,864,725 | B2 | 10/2014 | Ranalletta et al. |
| 8,864,737 | B2 | 10/2014 | Hasegawa et al. |
| 8,870,832 | B2 | 10/2014 | Raday et al. |
| 8,870,846 | B2 | 10/2014 | Davis et al. |
| 8,882,738 | B2 | 11/2014 | Fangrow et al. |
| 8,900,212 | B2 | 12/2014 | Kubo |
| 8,910,919 | B2 | 12/2014 | Bonnal et al. |
| 8,926,554 | B2 | 1/2015 | Okuda et al. |
| 8,945,084 | B2 | 2/2015 | Warren et al. |
| 8,973,622 | B2 | 3/2015 | Lopez |
| 8,974,433 | B2 | 3/2015 | Fangrow |
| 8,986,262 | B2 | 3/2015 | Young et al. |
| 8,992,501 | B2 | 3/2015 | Siefert et al. |
| 9,005,179 | B2 | 4/2015 | Fangrow et al. |
| 9,005,180 | B2 | 4/2015 | Siefert et al. |
| 9,060,921 | B2 | 6/2015 | Siefert et al. |
| 9,067,049 | B2 | 6/2015 | Panian et al. |
| 9,072,657 | B2 | 7/2015 | Siefert et al. |
| 9,089,474 | B2 | 7/2015 | Cederschiöld |
| 9,089,475 | B2 | 7/2015 | Fangrow |
| 9,107,808 | B2 | 8/2015 | Fangrow |
| 9,117,012 | B2 | 8/2015 | Basaglia |
| 9,132,062 | B2 | 9/2015 | Fangrow |
| 9,132,063 | B2 | 9/2015 | Lev et al. |
| 9,144,646 | B2 | 9/2015 | Barron, III et al. |
| 9,198,832 | B2 | 12/2015 | Moy et al. |
| 9,205,248 | B2 | 12/2015 | Wu et al. |
| 9,211,231 | B2 | 12/2015 | Mansour et al. |
| 9,278,206 | B2 | 3/2016 | Fangrow |
| 9,345,640 | B2 | 5/2016 | Mosler et al. |
| 9,345,641 | B2 | 5/2016 | Kraus et al. |
| 9,351,905 | B2 | 5/2016 | Fangrow et al. |
| 9,358,182 | B2 | 6/2016 | Garfield et al. |
| 9,370,466 | B2 | 6/2016 | Garfield et al. |
| 9,381,135 | B2 | 7/2016 | Reynolds et al. |
| 9,381,137 | B2 | 7/2016 | Garfield et al. |
| 9,381,339 | B2 | 7/2016 | Wu et al. |
| 9,440,060 | B2 | 9/2016 | Fangrow |
| 9,511,989 | B2 | 12/2016 | Lopez |
| 9,572,750 | B2 | 2/2017 | Mansour et al. |
| 9,585,812 | B2 | 3/2017 | Browka et al. |
| 9,597,260 | B2 | 3/2017 | Ivosevic |
| 9,610,217 | B2 | 4/2017 | Fangrow |
| 9,615,997 | B2 | 4/2017 | Fangrow |
| 9,662,272 | B2 | 5/2017 | Warren et al. |
| 9,763,855 | B2 | 9/2017 | Fangrow et al. |
| 9,827,163 | B2 | 11/2017 | Lopez et al. |
| 9,895,291 | B2 | 2/2018 | Fangrow |
| 9,895,526 | B2 | 2/2018 | Korogi et al. |
| 9,919,826 | B2 | 3/2018 | Ivosevic |
| 9,931,275 | B2 | 4/2018 | Fangrow |
| 9,931,276 | B2 | 4/2018 | Lopez |
| 9,987,195 | B2 | 6/2018 | Fangrow |
| 9,993,390 | B2 | 6/2018 | Seifert et al. |
| 9,993,391 | B2 | 6/2018 | Warren et al. |
| 9,999,569 | B2 | 6/2018 | Kriheli |
| 10,016,339 | B2 | 7/2018 | Guala |
| 10,022,302 | B2 | 7/2018 | Warran et al. |
| 10,071,020 | B2 | 9/2018 | Warren et al. |
| 10,086,188 | B2 | 10/2018 | Fangrow |
| 10,117,807 | B2 | 11/2018 | Fangrow |
| 10,201,476 | B2 | 2/2019 | Fangrow |
| 10,292,904 | B2 | 5/2019 | Fangrow |
| 10,299,989 | B2 | 5/2019 | Fangrow |
| 10,327,989 | B2 | 6/2019 | Fangrow |
| 10,327,991 | B2 | 6/2019 | Seifert et al. |
| 10,327,992 | B2 | 6/2019 | Fangrow et al. |

(56) References Cited

U.S. PATENT DOCUMENTS 10,327,993 B2 6/2019 Fangrow et al.
10,369,349 B2 8/2019 Nelson
10,391,293 B2 8/2019 Fangrow
10,406,072 B2 9/2019 Chhikara et al.
10,492,993 B2 12/2019 Seifert et al.
10,688,022 B2 6/2020 Fangrow
10,806,672 B2 10/2020 Fangrow
10,918,573 B2 2/2021 Fangrow
10,987,277 B2 4/2021 Fangrow
11,013,664 B2 5/2021 Fangrow et al.
11,129,773 B2 9/2021 Fangrow
11,185,471 B2 11/2021 Fangrow
11,504,302 B2 11/2022 Chhikara et al.
11,529,289 B2 * 12/2022 Fangrow ................. A61M 5/32
11,648,181 B2 5/2023 Chhikara et al.
11,654,086 B2 5/2023 Fangrow
11,672,734 B2 6/2023 Fangrow
11,696,871 B2 7/2023 Seifert et al.
11,744,775 B2 9/2023 Chhikara et al.
11,857,499 B2 1/2024 Fangrow
11,963,932 B2 4/2024 Seifert et al.
12,280,013 B2 4/2025 Fangrow
12,350,234 B2 7/2025 Warren et al.
12,350,237 B2 7/2025 Fangrow
12,377,022 B2 8/2025 Fangrow
12,383,469 B2 8/2025 Fangrow
2002/0087144 A1 7/2002 Zinger et al.
2002/0095133 A1 7/2002 Gillis et al.
2002/0193777 A1 12/2002 Aneas
2003/0070726 A1 4/2003 Andreasson et al.
2003/0153895 A1 8/2003 Leinsing
2003/0216695 A1 11/2003 Yang
2003/0229330 A1 12/2003 Hickle
2004/0073169 A1 4/2004 Amisar et al.
2004/0073189 A1 4/2004 Wyatt et al.
2004/0123868 A1 7/2004 Rutter
2005/0087715 A1 4/2005 Doyle
2005/0131357 A1 6/2005 Denton et al.
2005/0148992 A1 7/2005 Simas, Jr. et al.
2005/0203481 A1 9/2005 Orlu et al.
2006/0025747 A1 2/2006 Sullivan et al.
2006/0111667 A1 5/2006 Matsuura et al.
2006/0149309 A1 7/2006 Paul et al.
2006/0184103 A1 8/2006 Paproski et al.
2006/0184139 A1 8/2006 Quigley et al.
2007/0071243 A1 3/2007 Nanda
2007/0093775 A1 4/2007 Daly
2007/0106244 A1 5/2007 Mosler et al.
2007/0112324 A1 5/2007 Hamedi-Sangsari
2007/0208320 A1 9/2007 Muramatsu et al.
2008/0045919 A1 2/2008 Jakob et al.
2008/0067462 A1 3/2008 Miller et al.
2008/0140021 A1 6/2008 Richmond
2008/0172003 A1 7/2008 Plishka et al.
2008/0177244 A1 7/2008 Capitaine et al.
2008/0208159 A1 8/2008 Stanus et al.
2008/0287914 A1 11/2008 Wyatt et al.
2009/0057258 A1 3/2009 Tornqvist
2010/0000035 A1 1/2010 Lee
2010/0059474 A1 3/2010 Brandenburger et al.
2010/0076397 A1 3/2010 Reed et al.
2010/0084397 A1 4/2010 Kubo et al.
2010/0106129 A1 4/2010 Goeckner et al.
2010/0160889 A1 6/2010 Smith et al.
2010/0179506 A1 7/2010 Shemesh et al.
2010/0218846 A1 9/2010 Kriheli
2010/0242993 A1 9/2010 Hoang et al.
2010/0249723 A1 9/2010 Fangrow, Jr.
2010/0280485 A1 11/2010 Choi et al.
2010/0305548 A1 12/2010 Kraushaar
2011/0004183 A1 1/2011 Carrez et al.
2011/0125104 A1 5/2011 Lynn
2011/0125128 A1 5/2011 Nord et al.
2011/0175347 A1 7/2011 Okiyama
2011/0184382 A1 7/2011 Cady
2011/0208128 A1 8/2011 Wu et al.
2011/0224611 A1 9/2011 Lum et al.
2011/0240158 A1 10/2011 Py
2011/0257621 A1 10/2011 Fangrow
2011/0264037 A1 10/2011 Foshee et al.
2012/0046636 A1 2/2012 Kriheli
2012/0053555 A1 3/2012 Ariagno et al.
2012/0059346 A1 3/2012 Sheppard et al.
2012/0067429 A1 3/2012 Mosler et al.
2012/0078091 A1 3/2012 Suchecki
2012/0078214 A1 3/2012 Finke et al.
2012/0078215 A1 3/2012 Finke et al.
2012/0109077 A1 5/2012 Ryan
2012/0157964 A1 6/2012 Haimi
2012/0172830 A1 7/2012 Yokoyama et al.
2012/0215181 A1 8/2012 Lee
2012/0220978 A1 8/2012 Lev et al.
2012/0298254 A1 11/2012 Brem et al.
2012/0302986 A1 11/2012 Brem et al.
2013/0033034 A1 2/2013 Trombley, III et al.
2013/0053814 A1 2/2013 Mucientes et al.
2013/0053815 A1 2/2013 Mucientes et al.
2013/0060226 A1 3/2013 Fini et al.
2013/0066293 A1 3/2013 Garfield et al.
2013/0110053 A1 5/2013 Yoshino et al.
2013/0130197 A1 5/2013 Jessop et al.
2013/0180618 A1 7/2013 Py
2013/0199669 A1 8/2013 Moy et al.
2013/0218121 A1 8/2013 Waller et al.
2013/0226099 A1 8/2013 Fangrow
2013/0228239 A1 9/2013 Cederschiöld
2013/0231630 A1 9/2013 Kraus et al.
2013/0306169 A1 11/2013 Weibel
2014/0000738 A1 1/2014 Reynolds et al.
2014/0014210 A1 1/2014 Cederschiöld
2014/0020792 A1 1/2014 Kraus et al.
2014/0107588 A1 4/2014 Fangrow
2014/0124087 A1 5/2014 Anderson et al.
2014/0124092 A1 5/2014 Gonnelli et al.
2014/0150925 A1 6/2014 Sjogren et al.
2014/0230932 A1 8/2014 Fangrow
2014/0261727 A1 9/2014 Mansour et al.
2014/0261860 A1 9/2014 Heath et al.
2014/0261876 A1 9/2014 Mansour et al.
2014/0261877 A1 9/2014 Ivosevic et al.
2014/0276386 A1 9/2014 Mansour et al.
2014/0276649 A1 9/2014 Ivosevic et al.
2015/0065987 A1 3/2015 Fangrow
2015/0068640 A1 3/2015 Garfield et al.
2015/0082746 A1 3/2015 Ivosevic et al.
2015/0123398 A1 5/2015 Sanders et al.
2015/0126958 A1 5/2015 Sanders et al.
2015/0157848 A1 6/2015 Wu et al.
2015/0209230 A1 7/2015 Lev et al.
2015/0209232 A1 7/2015 Haindl
2015/0209233 A1 7/2015 Fukuoka
2015/0209572 A1 7/2015 Garfield et al.
2015/0250680 A1 9/2015 Browka et al.
2015/0250681 A1 9/2015 Lev et al.
2015/0265500 A1 9/2015 Russo et al.
2015/0297451 A1 10/2015 Marici et al.
2015/0297453 A1 10/2015 Kim et al.
2015/0297454 A1 10/2015 Sanders et al.
2015/0297456 A1 10/2015 Marici et al.
2015/0297459 A1 10/2015 Sanders et al.
2015/0297817 A1 10/2015 Guala
2015/0297839 A1 10/2015 Sanders et al.
2015/0320642 A1 * 11/2015 Fangrow ................... A61J 1/22
137/798
2015/0320992 A1 11/2015 Bonnet et al.
2015/0359709 A1 12/2015 Kriheli et al.
2015/0366758 A1 12/2015 Noguchi et al.
2016/0000653 A1 1/2016 Kramer
2016/0008534 A1 1/2016 Cowan et al.
2016/0038373 A1 2/2016 Ohlin
2016/0038374 A1 2/2016 Merhold et al.
2016/0051446 A1 2/2016 Lev et al.
2016/0058667 A1 3/2016 Kriheli
2016/0081878 A1 3/2016 Marks et al.

(56) References Cited

U.S. PATENT DOCUMENTS

| | | | |
|---|---|---|---|
| 2016/0081879 | A1 | 3/2016 | Garfield et al. |
| 2016/0101020 | A1 | 4/2016 | Guala |
| 2016/0106970 | A1 | 4/2016 | Fangrow |
| 2016/0136051 | A1 | 5/2016 | Lavi |
| 2016/0136412 | A1 | 5/2016 | McKinnon et al. |
| 2016/0206511 | A1 | 7/2016 | Garfield et al. |
| 2016/0206512 | A1 | 7/2016 | Chhikara et al. |
| 2016/0213568 | A1 | 7/2016 | Mansour et al. |
| 2016/0250102 | A1 | 9/2016 | Garfield et al. |
| 2016/0262981 | A1 | 9/2016 | Carrez et al. |
| 2016/0262982 | A1 | 9/2016 | Cederschiold |
| 2017/0007501 | A1 | 1/2017 | Schuldt-Lieb et al. |
| 2017/0027820 | A1 | 2/2017 | Okiyama et al. |
| 2017/0095404 | A1 | 4/2017 | Fangrow |
| 2017/0196772 | A1 | 7/2017 | Seifert |
| 2017/0196773 | A1 | 7/2017 | Fangrow |
| 2017/0202742 | A1 | 7/2017 | Cheng et al. |
| 2017/0202744 | A1 | 7/2017 | Fangrow |
| 2017/0202745 | A1 | 7/2017 | Seifert |
| 2017/0239140 | A1 | 8/2017 | Fangrow |
| 2017/0258682 | A1 | 9/2017 | Kriheli |
| 2017/0296431 | A1 | 10/2017 | Fangrow |
| 2017/0312176 | A1 | 11/2017 | Fangrow |
| 2017/0333288 | A1 | 11/2017 | Fangrow |
| 2018/0028402 | A1 | 2/2018 | Kriheli et al. |
| 2018/0099137 | A1 | 4/2018 | Fangrow |
| 2018/0125759 | A1 | 5/2018 | Fangrow |
| 2018/0161245 | A1 | 6/2018 | Kriheli |
| 2018/0193227 | A1 | 7/2018 | Marci et al. |
| 2018/0207063 | A1 | 7/2018 | Lopez et al. |
| 2018/0221572 | A1 | 8/2018 | Schlitt et al. |
| 2018/0250195 | A1 | 9/2018 | Fangrow |
| 2018/0280240 | A1 | 10/2018 | Fangrow et al. |
| 2019/0001114 | A1 | 1/2019 | Fangrow |
| 2019/0117515 | A1 | 4/2019 | Fangrow |
| 2019/0254926 | A1 | 8/2019 | Seifert |
| 2019/0269900 | A1 | 9/2019 | Fangrow |
| 2019/0350812 | A1 | 11/2019 | Chhikara et al. |
| 2019/0358125 | A1 | 11/2019 | Chhikara |
| 2020/0006372 | A1 | 1/2020 | Zhang et al. |
| 2020/0038293 | A1 | 2/2020 | Chhikara et al. |
| 2020/0069519 | A1 | 3/2020 | Fangrow |
| 2020/0069520 | A1 | 3/2020 | Fangrow |
| 2020/0093695 | A1 | 3/2020 | Seifert |
| 2020/0337948 | A1 | 10/2020 | Fangrow |
| 2021/0106499 | A1 | 4/2021 | Fangrow |
| 2021/0228444 | A1 | 7/2021 | Fangrow |
| 2021/0353500 | A1 | 11/2021 | Warren |
| 2022/0000798 | A1 | 1/2022 | Robbins et al. |
| 2022/0071848 | A1 | 3/2022 | Fangrow |
| 2022/0079843 | A1 | 3/2022 | Fangrow |
| 2023/0075991 | A1 | 3/2023 | Chhikara |
| 2023/0355476 | A1 | 11/2023 | Fangrow |
| 2024/0024197 | A1 | 1/2024 | Chhikara |
| 2024/0091104 | A1 | 3/2024 | Fangrow |
| 2024/0156685 | A1 | 5/2024 | Fangrow |
| 2024/0252399 | A1 | 8/2024 | Seifert |
| 2024/0315926 | A1 | 9/2024 | Fangrow |
| 2025/0143971 | A1 | 5/2025 | Fangrow |
| 2025/0161164 | A1 | 5/2025 | Fangrow |
| 2025/0170024 | A1 | 5/2025 | Fangrow |

FOREIGN PATENT DOCUMENTS

| | | |
|---|---|---|
| CN | 101801440 A | 8/2010 |
| EP | 0 829 250 | 3/1998 |
| EP | 2 036 529 | 3/2009 |
| EP | 2 744 469 | 10/2022 |
| GB | 2 000 685 | 1/1979 |
| JP | 39-17386 | 8/1961 |
| JP | 45-20604 | 8/1970 |
| JP | 57-208362 | 12/1982 |
| JP | H02-193677 | 7/1990 |
| JP | H06-66682 | 9/1994 |
| JP | 2001-505083 | 4/2001 |
| JP | 2011-516172 | 5/2011 |
| JP | 2012-228332 | 11/2012 |
| JP | 2015-077217 | 4/2015 |
| JP | 2015-211763 | 11/2015 |
| RU | 2264231 | 2/2005 |
| WO | WO 1984/004673 | 12/1984 |
| WO | WO 1997/02853 | 1/1997 |
| WO | WO 2000/035517 | 6/2000 |
| WO | WO 2005/065626 | 7/2005 |
| WO | WO 2008/036101 | 3/2008 |
| WO | WO 2008/129550 | 10/2008 |
| WO | WO 2008/153459 | 12/2008 |
| WO | WO 2008/153460 | 12/2008 |
| WO | WO 2009/105489 | 8/2009 |
| WO | WO 2009/146088 | 12/2009 |
| WO | WO 2010/069359 | 6/2010 |
| WO | WO 2010/093581 | 8/2010 |
| WO | WO 2010/120953 | 10/2010 |
| WO | WO 2011/150037 | 12/2011 |
| WO | WO 2013/104736 | 7/2013 |
| WO | WO 2013/134246 | 9/2013 |
| WO | WO 2014/116602 | 7/2014 |
| WO | WO 2014/163851 | 10/2014 |
| WO | WO 2015/029018 | 3/2015 |
| WO | WO 2015/118432 | 8/2015 |
| WO | WO 2015/166993 | 11/2015 |
| WO | WO 2016/142369 | 9/2016 |
| WO | WO 2016/147178 | 9/2016 |
| WO | WO 2018/064206 | 4/2018 |
| WO | WO 2018/186361 | 10/2018 |

OTHER PUBLICATIONS

ICU's Response dated Dec. 8, 2023 to European Opposition (dated Jul. 24, 2023), re EP Application No. 12823375.6.
Opposer's Response to ICU's Response to the Opposition, dated Mar. 4, 2024, re EP Application No. 12823375.6.
Summons to attend oral proceedings, dated Apr. 12, 2024, re EP Application No. 12823375.6.
Wehmeir, Sally: "Oxford Advanced Learner's" Oxford University Press, 2000—in two pages.
Wikipedia, "Check Valve," [https://en.wikipedia.org/wiki/Check_valve], Aug. 16, 2011, in four pages.
English translation of Notice of Opposition filed by B. Braun Melsungen AG against European Patent No. EP 2 744 469 B1, dated Jul. 19, 2023.
Reply to Opposition filed against European Patent No. EP 2 744 469 B1, dated Dec. 8, 2023.
Auxiliary Requests filed with Reply to Opposition filed against European Patent No. EP 2 744 469 B1, dated Dec. 8, 2023.
Opposer's Response to Reply to Opposition filed against European Patent No. EP 2 744 469 B1, dated Feb. 27, 2024.
Preliminary Opinion of the European Patent Office in Opposition filed against European Patent No. EP 2 744 469 B1, dated Apr. 12, 2024.
European Extended Search Report re EP Application No. EP 17745028.5, dated Jul. 15, 2019.
International Invitation to Pay Additional Fees (w/cited art), re PCT Application No. PCT/US2017/015468, mailed Mar. 7, 2017.
International Search Report and /Written Opinion, re PCT Application No. PCT/US2017/015468, mailed May 25, 2017.
International Preliminary Report on Patentability, re PCT Application No. PCT/US2017/015468, issued Jul. 31, 2018.
Clave—NeedleFree Connector, 2-page brochure. Jan. 2012 ICU Medical, Inc. (M1-1065 Rev. 04).
Equashield, Hazardous Drugs Closed System Transfer Device. Two webpages: http:/www.equashield.com, downloaded Jul. 22, 2013.
Genie—Closed Vial Access Device, 2-page brochure. Jan. 2012 ICU Medical, Inc. (M1-1186 Rev. 11).
OnGuard Contained Medication System with Tevadaptor Components, B. Braun Medical, Inc., Apr. 2007.
PhaSeal, The PhaSeal® Solution, http://www.phaseal.com/siteUS/page.asp?menuitem=145&right=0, dated Jan. 9, 2006.
PhaSeal, How to Use PhaSeal®, http://www.phaseal.com/siteUS/movies.asp?main=filmsmain&right=filmsright, dated Jul. 25, 2005.

(56) References Cited

OTHER PUBLICATIONS

"Protection Safety Products", IV Sets and Access Devices Medication Delivery Catalog, CHEMO-AIDE Dispensing Pin, Dec. 2002, pp. 7,21, Baxter Healthcare Corporation, Round Lake, IL.
Spiros—Closed Male Luer. 2-page brochure. Jan. 2012 ICU Medical, Inc. (M1-1184 Rev. 11).
ICU's Response Letter dated Aug. 5, 2024, regarding the Preliminary Opinion of the EPO Opposition (Opposition filed against European Patent No. EP 2 744 469 B1).
Minutes, Oral Proceedings, re EP App., 12823375.6, dated Nov. 25, 2024.
Braun's response/comments with English translation dated Sep. 6, 2024, to ICU's response dated Aug. 5, 2024 (Opposition filed against European Patent No. EP 2 744 469 B1).
EPO Decision on Opposition filed against European Patent No. EP 2 744 469, dated Nov. 25, 2024, in 30 pages.
EPO Withdrawal of the appeal filed against European Patent No. EP 2 744 469, dated Feb. 11, 2025.

* cited by examiner

PRESSURE-REGULATING VIAL ADAPTORS

RELATED APPLICATIONS

This application is a continuation of U.S. application Ser. No. 16/415,765, filed on May 17, 2019, and issued as U.S. Pat. No. 11,529,289 on Dec. 20, 2022, which is a continuation of U.S. application Ser. No. 16/073,715, filed on Jul. 27, 2018, and issued as U.S. Pat. No. 10,292,904 on May 21, 2019, which is a national phase of International Application No. PCT/US2017/015468 designating the United States, with an international filing date of Jan. 27, 2017, which claims the benefit of U.S. Provisional Patent Application No. 62/288,950, filed on Jan. 29, 2016, and entitled "Pressure-Regulating Vial Adaptors," the entire contents of each of which are incorporated by reference herein and made part of this specification.

BACKGROUND

Technical Field

Certain embodiments disclosed herein relate to adaptors for coupling with medicinal vials, and components thereof, and methods to contain vapors and/or to aid in regulating pressures within medicinal vials.

Description of the Related Art

It is a common practice to store medicines or other medically related fluids in vials or other containers. In some instances, the medicines or fluids so stored are therapeutic if injected into the bloodstream, but harmful if inhaled or if contacted by exposed skin. Certain known systems for extracting potentially harmful medicines from vials suffer from various drawbacks.

SUMMARY

A method of injecting fluid into a vial can include inserting a piercing member of a vial adaptor at least partially into a vial. In some embodiments, the method includes at least partially removing a cover from a regulator assembly of the vial adaptor. In some embodiments, the regulator assembly includes a regulator base. The regulator base can be in fluid communication with the vial when the piercing member is inserted at least partially into the vial. The regulator assembly can include a regulator nest. In some embodiments, the regulator nest is coupled with the regulator base and/or positioned within the regulator base. In some embodiments, the cover is fitted around a radially outward portion of the regulator assembly. In some cases, the regulator assembly includes a flexible enclosure. The flexible enclosure can be connected to the regulator nest and/or can be configured to be positioned within a storage chamber within the regulator base in a contracted configuration. In some embodiments, the flexible enclosure is configured to be positioned at least partially outside of the regulator base in an expanded configuration. In some embodiments, the method includes injecting fluid through the piercing member from a connector interface of the vial adaptor after the cover is at least partially removed from the regulator assembly. The method can include expanding the flexible enclosure outside of the regulator nest only after the cover is at least partially removed from the regulator assembly.

According to some embodiments, the step of at least partially removing a cover comprises inflating the flexible enclosure, thereby causing tearing of the cover. According to some embodiments, causing tearing of the cover comprises causing tearing of perforated portions of the cover.

According to some embodiments, the at least partially removing a cover step is performed sequentially before the injecting fluid step.

According to some embodiments, the expanding the flexible enclosure step cannot be performed prior to the at least partially removing a cover step.

According to some embodiments, the method includes connecting a syringe to the connector interface of the vial adaptor.

According to some embodiments, injecting fluid through the piercing member increases pressure within the vial, and increasing pressure within the vial directs fluid into the flexible enclosure.

According to some embodiments, the method includes reducing pressure within the vial via expansion of the flexible enclosure after the step of at least partial removal of the cover.

According to some embodiments, the method includes withdrawing fluid from the vial via the connector interface.

According to some embodiments, the method includes introducing ambient air to the vial via an intake valve during at least a portion of the withdrawing fluid step.

According to some embodiments, the at least partially removing a cover step includes tearing at least a portion of the cover along a perforation.

According to some embodiments, the at least partially removing a cover step includes pulling a tab connected to the cover.

According to some embodiments, the method includes completely removing the cover.

According to some embodiments, the method includes inhibiting expansion of the flexible enclosure prior to the at least partially removing a cover step.

According to some embodiments, a vial adaptor can include a connector interface. In some embodiments, the vial adaptor includes a piercing member. The piercing member can be in partial communication with the connector interface and/or a regulator lumen. In some embodiments, the vial adaptor includes a regulator assembly. The regulator assembly can include a regulator base. In some embodiments, the regulator base has a coupling protrusion configured to couple with the regulator lumen. In some embodiments, the regulator assembly includes a regulator nest. The regulator nest can be coupled with the regulator base. In some embodiments, the regulator assembly includes a storage chamber. The storage chamber can be formed at least partially by one or both of the regulator base and regulator nest. In some embodiments, the regulator assembly includes a cover. The cover can be connected to one or both of the regulator base and regulator nest. In some embodiments, the cover is fitted around a radially outward portion of one or both of the regulator base and regulator nest. In some embodiments, the regulator assembly includes a flexible enclosure. The flexible enclosure can be connected to the regulator nest. In some embodiments, the flexible enclosure is configured to be positioned within the storage chamber in a contracted configuration and/or is configured to be positioned at least partially outside of the regulator base in an expanded configuration. In some embodiments, the flexible enclosure is inhibited from transitioning to the expanded configuration prior to removal or modification of the cover from the regulator assembly.

According to some embodiments, the flexible enclosure is inhibited from transitioning to the expanded configuration prior to removal of the cover from the regulator assembly by a user of the vial adaptor.

According to some embodiments, the cover is constructed from a material configured to retain the flexible enclosure within the storage chamber until a user removes at least a portion of the cover from the regulator assembly.

According to some embodiments, the cover is connected to the regulator base in a manner configured to prevent expansion of the flexible enclosure outside of the storage chamber prior to removal by a user of at least a portion of the cover from the regulator assembly.

According to some embodiments, the cover is configured to inhibit user access to the storage chamber prior to at least partial removal of the cover from the regulator assembly.

According to some embodiments, the flexible enclosure is configured to expand only after a user at least partially removes the cover from the regulator assembly.

According to some embodiments, the cover is perforated and is configured to tear in response to expansion of the flexible enclosure.

According to some embodiments, a medical adaptor can be capable of coupling with a sealed container. The medical adaptor can include a housing. The housing can include a medical connector interface. In some embodiments, the housing includes an access channel. The access channel can be capable of removing medicinal fluid from a sealed container and can extend between the medical connector interface and a distal access port. In some embodiments, the housing includes a regulator channel. The medical adaptor can include a regulator assembly. The regulator assembly can be in fluid communication with the regulator channel. In some embodiments, the regulator assembly includes a storage chamber. In some embodiments, the regulator assembly includes a flexible enclosure. The flexible enclosure can be in fluid communication with the regulator channel. In some embodiments, the flexible enclosure is capable of transitioning between a stored configuration wherein the flexible enclosure is positioned within the storage chamber and a deployed configuration wherein at least a portion of the flexible enclosure is positioned outside of the storage chamber. In some embodiments, the flexible enclosure has a stored volume when in the stored configuration and a deployed volume when in the deployed configuration. In some embodiments, the flexible enclosure has a stored width when in the stored configuration and a deployed width when in the deployed configuration. The regulator assembly can include an intake valve. The intake valve can be in fluid communication with the flexible enclosure and/or can be positioned between the flexible enclosure and the regulator channel. In some embodiments, the intake valve is capable of transitioning between an opened configuration and a closed configuration. The intake valve can be configured to facilitate fluid communication from an ambient environment to an interior of the regulator assembly when the intake valve is in the opened configuration. In some embodiments, the intake valve comprises a flexible disc having a central aperture and an outer perimeter. In some embodiments, the regulator assembly includes a biasing structure positioned between the central aperture and the outer perimeter. In some embodiments, the biasing structure is configured to bias the intake valve to the closed configuration.

A method of manufacturing a vial adaptor can include providing a regulator base. In some embodiments, the regulator base comprises one or more coupling features and/or one or more air intake apertures. In some embodiments, the method includes covering the one or more air intake apertures with a filter. In some embodiments, the method includes positioning an annular diaphragm in contact with the regulator base. The method can include coupling a regulator nest to the regulator base such that the diaphragm is positioned at least partially between the regulator base and the regulator nest. In some embodiments, the method includes connecting a flexible enclosure to the regulator nest such that an interior of the flexible enclosure is in fluid communication with the diaphragm and the flexible enclosure is positioned within a storage chamber when in a stored configuration. The method can include connecting a cover to one or more of the regulator base and regulator nest such that the flexible enclosure is inhibited from expanding out from the storage chamber before removal of at least a portion of the cover from one or more of the regulator base and regulator nest.

According to some embodiments, the method includes connecting the regulator base to a lumen of a body portion of the vial adaptor such that the flexible enclosure is in fluid communication with a piercing member of the vial adaptor.

According to some embodiments, the method includes perforating a portion of the cover.

According to some embodiments, the method includes connecting a tab to the cover.

According to some embodiments, the method includes connecting a cover to one or more of the regulator base and regulator nest such that the flexible enclosure is inhibited from expanding out from the storage chamber before a user removes at least a portion of the cover from one or more of the regulator base and regulator nest.

According to some embodiments, the cover is configured to tear in response to expansion of the flexible enclosure.

According to some embodiments, a vial adaptor includes a connector interface. The vial adaptor can include a piercing member. In some embodiments, the piercing member is in partial communication with the connector interface. In some embodiments, the vial adaptor includes a lumen that extends radially outward generally perpendicular from the connector interface. In some embodiments, the vial adaptor includes a regulator assembly. The regulator assembly can include a regulator base. The regulator base can have a coupling protrusion configured to couple with the lumen. In some embodiments, the regulator assembly includes a regulator nest. The regulator nest can be configured to couple with the regulator base and/or can be positioned within the regulator base. In some embodiments, the regulator assembly includes a storage chamber defined at least partially by one or both of the regulator base and regulator nest. In some embodiments, the regulator assembly includes an expansion inhibitor. The expansion inhibitor can be connected to one or both of the regulator base and regulator nest. In some embodiments, the expansion inhibitor has an aperture on a side of the regulator assembly opposite the coupling protrusion of the regulator base. In some embodiments, the expansion inhibitor includes one or more weakened portions. The regulator assembly can include a flexible enclosure. The flexible enclosure can be connected to the regulator nest and/or can be configured to be positioned within the storage chamber in a contracted configuration. The flexible enclosure can be configured to be positioned at least partially outside of the regulator base in an expanded configuration. In some embodiments expansion of the flexible enclosure is configured to tear a weakened portion of the expansion inhibitor.

According to some embodiments, at least one of the one or more weakened portions is a perforation.

According to some embodiments, the expansion inhibitor extends over at least a portion of a side of the regulator assembly adjacent the coupling protrusion and over at least a portion of a side of the regulator assembly opposite the coupling protrusion.

According to some embodiments, a width of the aperture of the expansion inhibitor is between 3/10 and 1/2 of a width of the regulator assembly, as measured perpendicular to an axis of the coupling protrusion.

A method of manufacturing a vial adaptor can include providing a body portion having connector interface, a piercing member in partial communication with the connector interface, and/or a lumen that extends radially outward generally perpendicular from the connector interface. In some embodiments, the method includes assembling a regulator assembly. Assembling the regulator assembly can comprise providing a base having a protrusion configured to couple with the lumen. In some embodiments, assembling the regulator assembly comprises coupling a nest with the base and/or positioning the nest at least partially within the base. In some embodiments, a storage chamber is formed at least partially by one or both of the base and nest. Assembling the regulator assembly can include connecting a cover to one or both of the base and nest. The cover can have an aperture on a side of the regulator assembly opposite the coupling protrusion of the base and one or more weakened portions. In some embodiments, the method of manufacturing a vial adaptor includes connecting an inflatable enclosure to the nest. In some embodiments, the inflatable enclosure is configured to be positioned within the storage chamber in a contracted configuration and configured to be positioned at least partially outside of the base in an expanded configuration. In some embodiments, expansion of the inflatable enclosure is configured to tear a weakened portion of the cover.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

FIG. 3I illustrates a front partial cross-sectional view of the vial adaptor of FIG. 3A with the flexible enclosure in the expanded configuration.

DETAILED DESCRIPTION

Figure 1:
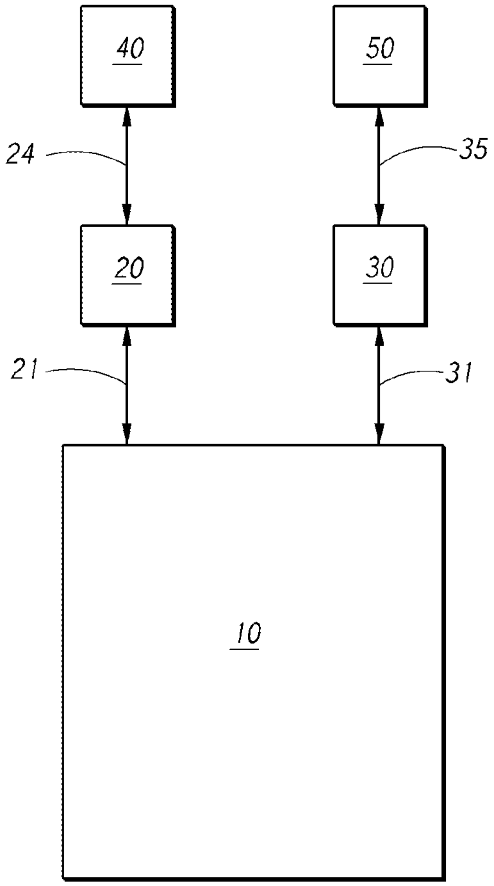
FIG. 1 schematically illustrates a system for removing fluid from and/or injecting fluid into a vial.

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The drawing showing certain embodiments can be semi-diagrammatic and not to scale and, particularly, some of the dimensions are for the clarity of presentation and are shown greatly exaggerated in the drawings.

For expository purposes, the term "horizontal" as used herein is defined as a plane parallel to the plane or surface of the floor of the area in which the device being described is used or the method being described is performed, regardless of its orientation. The term "floor" floor can be interchanged with the term "ground." The term "vertical" refers to a direction perpendicular to the horizontal as just defined. Terms such as "above," "below," "bottom," "top," "side," "higher," "lower," "upper," "over," and "under," are defined with respect to the horizontal plane.

Numerous medicines and other therapeutic fluids are stored and distributed in medicinal vials or other containers of various shapes and sizes. These vials are hermetically sealed to prevent contamination or leaking of the stored fluid. The pressure differences between the interior of the sealed vials and the particular atmospheric pressure in which the fluid is later removed often give rise to various problems, as well as the release of potentially harmful vapors.

For instance, introducing a piercing member of a vial adaptor through the septum of a vial can cause the pressure within the vial to rise. This pressure increase can cause fluid to leak from the vial at the interface of the septum and piercing member or at the attachment interface of the adaptor and a medical device, such as a syringe. Also, it can be difficult to withdraw an accurate amount of fluid from a sealed vial using an empty syringe, or other medical instrument, because the fluid may be naturally urged back into the vial once the syringe plunger is released. Furthermore, as the syringe is decoupled from the vial, pressure differences can often cause an amount of fluid to spurt from the syringe or the vial.

Moreover, in some instances, introducing a fluid into the vial can cause the pressure to rise in the vial. For example, in certain cases it can be desirable to introduce a solvent (such as sterile saline) into the vial, e.g., to reconstitute a lyophilized pharmaceutical in the vial. Such introduction of fluid into the vial can cause the pressure in the vial to rise above the pressure of the surrounding environment, which can result in fluid leaking from the vial at the interface of the septum and piercing member or at the attachment interface of the adaptor and a medical device, such as a syringe. Further, the increased pressure in the vial can make it difficult to introduce an accurate amount of the fluid into the vial with a syringe, or other medical instrument. Also, should the syringe be decoupled from the vial when the pressure inside the vial is greater than the surrounding pressure (e.g., atmospheric), the pressure gradient can cause a portion of the fluid to spurt from the vial.

Additionally, in many instances, air bubbles are drawn into the syringe as fluid is withdrawn from the vial. Such bubbles are generally undesirable as they could result in an embolus if injected into a patient. To rid a syringe of bubbles after removal from the vial, medical professionals often flick the syringe, gathering all bubbles near the opening of the syringe, and then forcing the bubbles out. In so doing, a small amount of liquid is usually expelled from the syringe as well. Medical personnel generally do not take the extra step to re-couple the syringe with the vial before expelling the bubbles and fluid. In some instances, this may even be prohibited by laws and regulations. Such laws and regulations may also necessitate expelling overdrawn fluid at some location outside of the vial in certain cases. Moreover, even if extra air or fluid were attempted to be reinserted in the vial, pressure differences can sometimes lead to inaccurate measurements of withdrawn fluid.

To address these problems caused by pressure differentials, medical professionals frequently pre-fill an empty syringe with a precise volume of ambient air corresponding to the volume of fluid that they intend to withdraw from the vial. The medical professionals then pierce the vial and expel this ambient air into the vial, temporarily increasing the pressure within the vial. When the desired volume of fluid is later withdrawn, the pressure differential between the interior of the syringe and the interior of the vial is generally near equilibrium. Small adjustments of the fluid volume within the syringe can then be made to remove air bubbles without resulting in a demonstrable pressure differential between the vial and the syringe. However, a significant disadvantage to this approach is that ambient air, especially in a hospital setting, may contain various airborne viruses, bacteria, dust, spores, molds, and other unsanitary and harmful contaminants. The pre-filled ambient air in the syringe may contain one or more of these harmful substances, which may then mix with the medicine or other therapeutic fluid in the vial. If this contaminated fluid is injected directly into a patient's bloodstream, it can be particularly dangerous because it circumvents many of the body's natural defenses to airborne pathogens. Moreover, patients who need the medicine and other therapeutic fluids are more likely to be suffering from a diminished infection-fighting capacity.

In the context of oncology and certain other drugs, all of the foregoing problems can be especially serious. Such drugs, although helpful when injected into the bloodstream of a patient, can be extremely harmful if inhaled or touched. Accordingly, such drugs can be dangerous if allowed to spurt unpredictably from a vial due to pressure differences. Furthermore, these drugs are often volatile and may instantly aerosolize when exposed to ambient air. Accordingly, expelling a small amount of such drugs in order to clear a syringe of bubbles or excess fluid, even in a controlled manner, is generally not a viable option, especially for medical personnel who may repeat such activities numerous times each day.

Some devices use rigid enclosures for enclosing all or a portion of a volume-changing component or region for assisting in regulating pressure within a container. Although such enclosures can provide rigidity, they generally make the devices bulky and unbalanced. Coupling such a device with a vial generally can create a top-heavy, unstable system that is prone to tipping-over and possibly spilling the contents of the device and/or the vial.

Indeed, certain of such coupling devices include relatively large and/or heavy, rigid components that are cantilevered or otherwise disposed a distance from of the axial center of the device, thereby exacerbating the tendency for the device to tip-over.

Additionally, such rigid enclosures can increase the size of the device, which can require an increase in material to form the device and otherwise increase costs associated manufacturing, transporting, and/or storing the device. Further, such rigid enclosures can hamper the ability of the device to expand or contract to deliver a regulating fluid to the vial. No feature, structure, or step disclosed herein is essential or indispensable.

FIG. 1 is a schematic illustration of a container 10, such as a medicinal vial, that can be coupled with an accessor 20 and a regulator 30. In certain arrangements, the regulator 30 allows the removal of some or all of the contents of the container 10 via the accessor 20 without a significant change of pressure within the container 10.

In general, the container 10 is hermetically sealed to preserve the contents of the container 10 in a sterile environment. The container 10 can be evacuated or pressurized upon sealing. In some instances, the container 10 is partially or completely filled with a liquid, such as a drug or other medical fluid. In such instances, one or more gases can also be sealed in the container 10. In some instances, a solid or powdered substance, such as a lyophilized pharmaceutical, is disposed in the container 10.

The accessor 20 generally provides access to contents of the container 10 such that the contents may be removed or added to. In certain arrangements, the accessor 20 includes an opening between the interior and exterior of the container 10. The accessor 20 can further comprise a passageway between the interior and exterior of the container 10. In some configurations, the passageway of the accessor 20 can be selectively opened and closed. In some arrangements, the accessor 20 comprises a conduit extending through a surface of the container 10. The accessor 20 can be integrally formed with the container 10 prior to the sealing thereof or introduced to the container 10 after the container 10 has been sealed.

In some configurations, the accessor 20 is in fluid communication with the container 10, as indicated by an arrow 21. In certain of these configurations, when the pressure inside the container 10 varies from that of the surrounding environment, the introduction of the accessor 20 to the container 10 causes a transfer through the accessor 20. For example, in some arrangements, the pressure of the environment that surrounds the container 10 exceeds the pressure within the container 10, which may cause ambient air from the environment to ingress through the accessor 20 upon insertion of the accessor 20 into the container 10. In other arrangements, the pressure inside the container 10 exceeds that of the surrounding environment, causing the contents of the container 10 to egress through the accessor 20.

In some configurations, the accessor 20 is coupled with an exchange device 40. In certain instances, the accessor 20 and the exchange device 40 are separable. In some instances, the accessor 20 and the exchange device 40 are integrally formed. The exchange device 40 is configured to accept fluids and/or gases from the container 10 via the accessor 20, to introduce fluids and/or gases to the container 10 via the accessor 20, or to do some combination of the two. In some arrangements, the exchange device 40 is in fluid communication with the accessor 20, as indicated by an arrow 24. In certain configurations, the exchange device 40 comprises a medical instrument, such as a syringe.

In some instances, the exchange device 40 is configured to remove some or all of the contents of the container 10 via the accessor 20. In certain arrangements, the exchange device 40 can remove the contents independent of pressure differences, or lack thereof, between the interior of the container 10 and the surrounding environment. For example, in instances where the pressure outside of the container 10 exceeds that within the container 10, an exchange device 40 comprising a syringe can remove the contents of the container 10 if sufficient force is exerted to extract the plunger from the syringe. The exchange device 40 can similarly introduce fluids and/or gases to the container 10 independent of pressure differences between the interior of the container 10 and the surrounding environment.

In certain configurations, the regulator 30 is coupled with the container 10. The regulator 30 generally regulates the pressure within the container 10. As used herein, the term "regulate," or any derivative thereof, is a broad term used in its ordinary sense and includes, unless otherwise noted, any active, affirmative, or positive activity, or any passive, reactive, respondent, accommodating, or compensating activity that tends to effect a change. In some instances, the regulator 30 substantially maintains a pressure difference, or equilibrium, between the interior of the container 10 and the surrounding environment. As used herein, the term "maintain," or any derivative thereof, is a broad term used in its ordinary sense and includes the tendency to preserve an original condition for some period, with some small degree of variation permitted as may be appropriate in the circumstances. In some instances, the regulator 30 maintains a substantially constant pressure within the container 10. In certain instances, the pressure within the container 10 varies by no more than about 1 psi, no more than about 2 psi, no more than about 3 psi, no more than about 4 psi, or no more than about 5 psi. In still further instances, the regulator 30 equalizes pressures exerted on the contents of the container 10. As used herein, the term "equalize," or any derivative thereof, is a broad term used in its ordinary sense and includes the tendency for causing quantities to be the same or close to the same, with some small degree of variation permitted as may be appropriate in the circumstances. In certain configurations, the regulator 30 is coupled with the container 10 to allow or encourage equalization of a pressure difference between the interior of the container 10 and some other environment, such as the environment surrounding the container 10 or an environment within the exchange device 40. In some arrangements, a single device comprises the regulator 30 and the accessor 20. In other arrangements, the regulator 30 and the accessor 20 are separate units.

The regulator 30 is generally in communication with the container 10, as indicated by an arrow 31, and a reservoir 50, as indicated by another arrow 35. In some configurations, the reservoir 50 comprises at least a portion of the environment surrounding the container 10. In certain configurations, the reservoir 50 comprises a container, canister, bag, or other holder dedicated to the regulator 30. As used herein, the term "bag," or any derivative thereof, is a broad term used in its ordinary sense and includes, for example, any sack, balloon, bladder, receptacle, enclosure, diaphragm, or membrane capable of expanding and/or contracting, including structures comprising a flexible, supple, pliable, resilient, elastic, and/or expandable material. In some embodiments, the reservoir 50 includes a gas and/or a liquid. As used herein, the term "flexible," or any derivative thereof, is a broad term used in its ordinary sense and describes, for example, the ability of a component to bend, expand, contract, fold, unfold, or otherwise substantially deform or change shape when fluid is flowing into or out of the container 10 (e.g., via the accessor 20). Also, as used herein, the term "rigid," or any derivative thereof, is a broad term used in its ordinary sense and describes, for example, the ability of a component to generally avoid substantial deformation under normal usage when fluid is flowing into or out of the container 10 (e.g., via the accessor 20).

In certain embodiments, the regulator 30 provides fluid communication between the container 10 and the reservoir 50. In certain of such embodiments, the fluid in the reservoir 50 includes mainly gas so as not to appreciably dilute liquid contents of the container 10. In some arrangements, the regulator 30 comprises a filter to purify or remove contaminants from the gas or liquid entering the container 10, thereby reducing the risk of contaminating the contents of the container 10. In certain arrangements, the filter is hydrophobic such that air can enter the container 10 but fluid cannot escape therefrom. In some configurations, the regulator 30 comprises an orientation-actuated or orientation-sensitive check valve which selectively inhibits fluid communication between the container 10 and the filter. In some configurations, the regulator 30 comprises a check valve which selectively inhibits fluid communication between the container 10 and the filter when the valve and/or the container 10 are oriented so that the regulator 30 is held above (e.g., further from the floor than) the regulator 30.

In some embodiments, the regulator 30 prevents fluid communication between the container 10 and the reservoir 50. In certain of such embodiments, the regulator 30 serves as an interface between the container 10 and the reservoir 50. In some arrangements, the regulator 30 comprises a substantially impervious bag for accommodating ingress of gas and/or liquid to the container 10 or egress of gas and/or liquid from the container 10.

Figure 2:
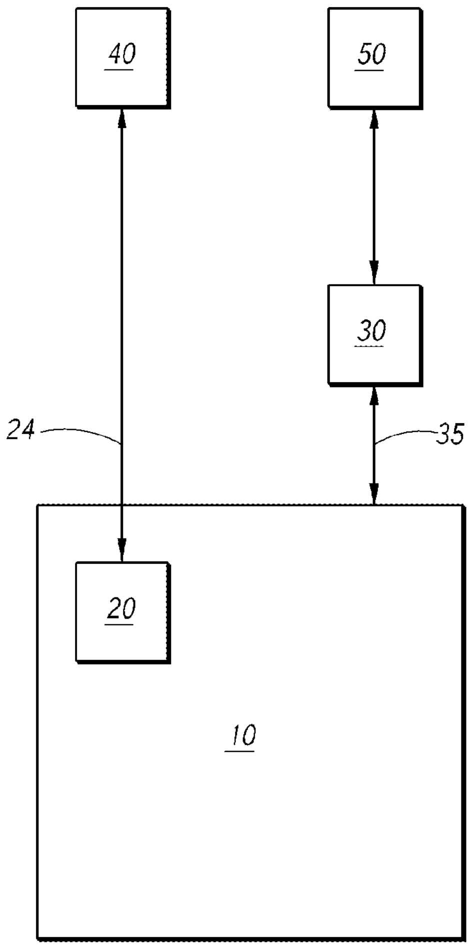
FIG. 2 schematically illustrates another system for removing fluid from and/or injecting fluid into a vial.

As schematically illustrated in FIG. 2, in certain embodiments, the accessor 20, or some portion thereof, is located within the container 10. As detailed above, the accessor 20 can be integrally formed with the container 10 or separate therefrom. In some embodiments, the regulator 30, or some portion thereof, is located outside the container 10. In some arrangements, the regulator 30 is integrally formed with the container 10. It is possible to have any combination of the accessor 20, or some portion thereof, entirely within, partially within, or outside of the container 10 and/or the regulator 30, or some portion thereof, entirely within, partially within, or outside of the container 10.

In certain embodiments, the accessor 20 is in fluid communication with the container 10. In further embodiments, the accessor 20 is in fluid communication with the exchange device 40, as indicated by the arrow 24.

The regulator 30 can be in fluid or non-fluid communication with the container 10. In some embodiments, the regulator 30 is located entirely outside the container 10. In certain of such embodiments, the regulator 30 comprises a closed bag configured to expand or contract external to the container 10 to maintain a substantially constant pressure within the container 10. In some embodiments, the regulator 30 is in communication, either fluid or non-fluid, with the reservoir 50, as indicated by the arrow 35.

Figure 2A:
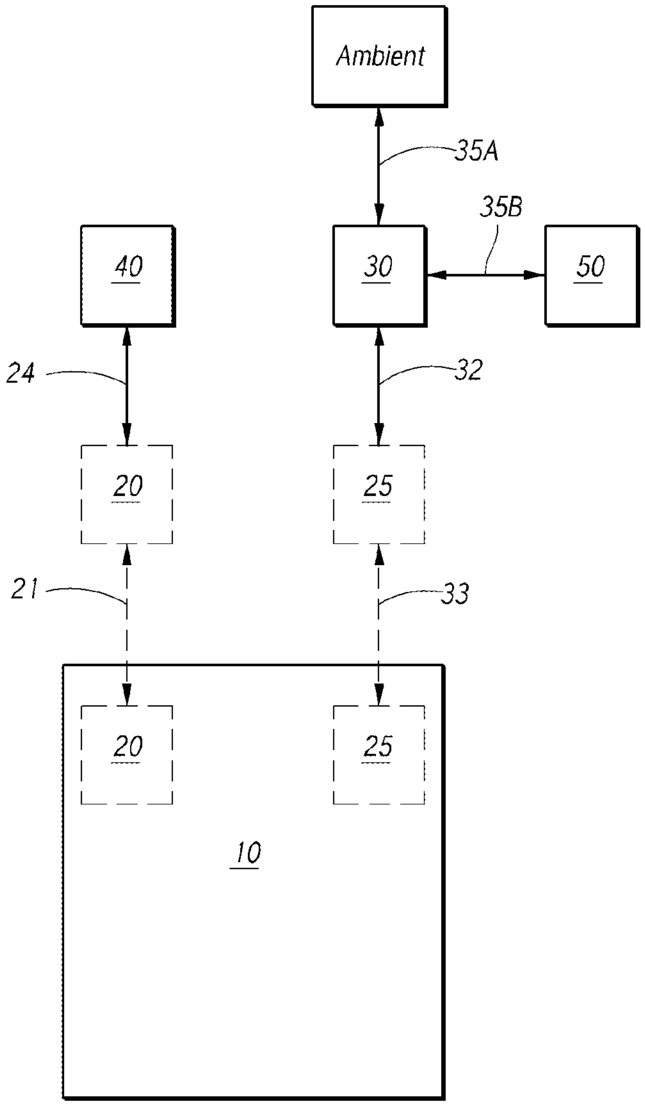
FIG. 2A schematically illustrates another system for removing fluid from and/or injecting fluid into a vial.

As schematically illustrated in FIG. 2A, in certain embodiments, the accessor 20, or some portion thereof, can be located within the container 10. In some embodiments, the accessor 20, or some portion thereof, can be located outside the container 10. In some embodiments, a valve 25, or some portion thereof, can be located outside the container 10. In some embodiments, the valve 25, or some portion thereof, can be located within the container 10. In some embodiments, the regulator 30 is located entirely outside the container 10. In some embodiments, the regulator 30, or some portion thereof, can be located within the container 10. It is possible to have any combination of the accessor 20, or some portion thereof, entirely within, partially within, or outside of the container 10 and/or the valve 25, or some portion thereof, entirely within, partially within, or outside of the container 10. It is also possible to have any combination of the accessor 20, or some portion thereof, entirely within, partially within, or outside of the container 10 and/or the regulator 30, or some portion thereof, entirely within, partially within, or outside of the container 10.

The accessor 20 can be in fluid communication with the container 10, as indicated by the arrow 21. In some embodiments, the accessor 20 can be in fluid communication with the exchange device 40, as indicated by the arrow 24.

In certain embodiments, the regulator 30 can be in fluid or non-fluid communication with a valve 25, as indicated by the arrow 32. In some embodiments, the valve 25 can be integrally formed with the container 10 or separate therefrom. In some embodiments, the valve 25 can be integrally formed with the regulator 30 or separate therefrom. In certain embodiments, the valve 25 can be in fluid or non-fluid communication with the container 10, as indicated by the arrow 33.

In some embodiments the regulator 30 can be in fluid or non-fluid communication with the ambient surroundings, as indicated by the arrow 35A. In some embodiments, the regulator 30 can be in fluid or non-fluid communication with a reservoir 50, as indicated by the arrow 35B. In some embodiments, the reservoir 50 can comprise a bag or other flexible enclosure. In some embodiments, the reservoir 50 comprises a rigid container surrounding a flexible enclosure. In some embodiments, the reservoir 50 comprises a partially-rigid enclosure.

According to some configurations, the regulator 30 can comprise a filter. In some embodiments, the filter can selectively inhibit passage of liquids and/or contaminants between the valve 25 and the reservoir 50 or the ambient surroundings. In some embodiments, the filter can selectively inhibit passage of liquids and/or contaminants between the reservoir 50 or ambient surroundings and the valve 25.

In some embodiments, the valve 25 can be a one-way check valve. In some embodiments, the valve 25 can be a two-way valve. According to some configurations, the valve 25 can selectively inhibit liquid communication between the filter and/or reservoir 50 and the container 10. In some embodiments, the valve 25 can selectively inhibit liquid communication between the container 10 and the filter and/or reservoir 50 when the container 10 is oriented above the exchange device 40.

Figure 2B:
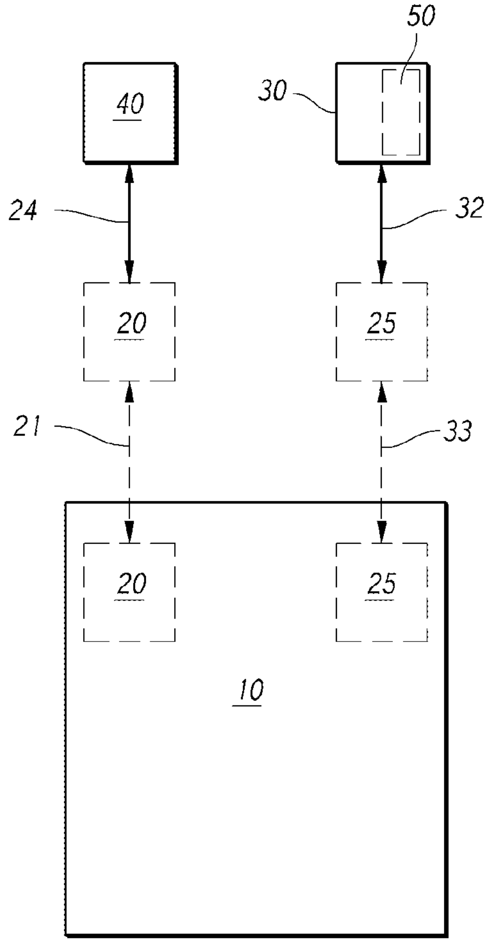
FIG. 2B schematically illustrates another system for removing fluid from and/or injecting fluid into a vial, wherein the flexible enclosure is in a contracted position.
Figure 2C:
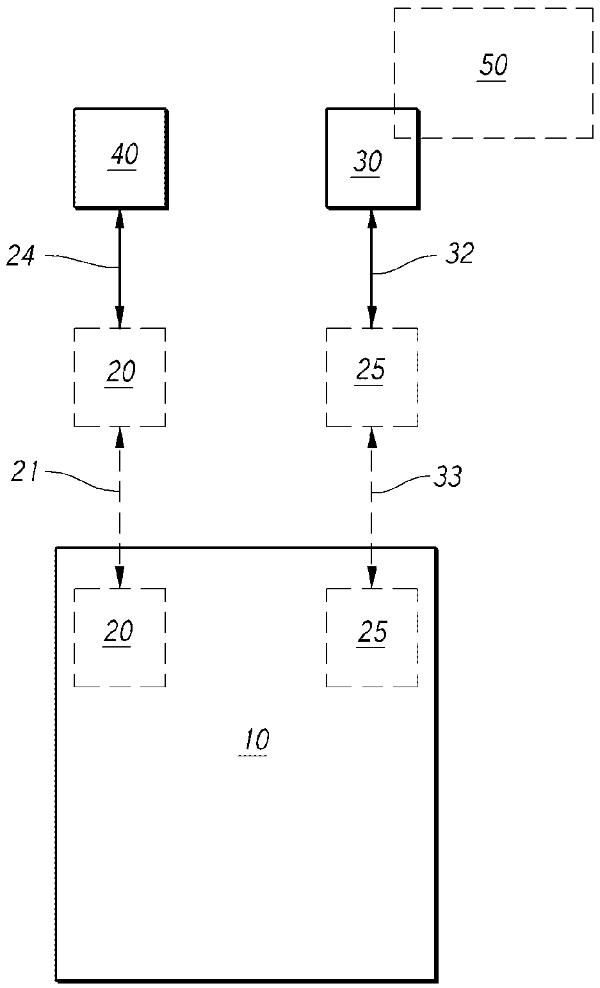
FIG. 2C schematically illustrates the system of FIG. 2B, wherein the flexible enclosure is in an expanded position.

As schematically illustrated in FIGS. 2B and 2C, in certain embodiments, the reservoir 50 can be located at least partially within the regulator 30. The regulator 30 can be in fluid communication with the container 10, as illustrated by arrows 32 and 33. In some embodiments, a valve 25 is located in the fluid path between the container 10 and the regulator 30. The regulator 30 can be configured to maintain a substantially constant pressure within the container 10 as fluid is introduced into and/or withdrawn from the vial 10. For example, in some embodiments, the reservoir 50 is configured to transition from a contracted or primarily interior configuration (e.g., as illustrated in FIG. 2B) to a primarily exterior or expanded configuration (e.g., as illustrated in FIG. 2C), upon addition of fluid into the container 10 via the accessor 20 or otherwise. As used herein, the term "expanded" is used in its broad and ordinary sense and includes configurations such as those shown in the figures, including deployed, unstored, unfolded, stretched, extended, unrolled, unfurled, or any combination thereof. As used herein, the term "contracted" is used in its broad and ordinary sense and includes configurations such as those shown in the figures, including stored, undeployed, folded, compacted, unstretched, unextended, rolled, furled, or any combination thereof. As shown in the drawings, "expanded" or "contracted," or variants of these words, or similar terms, do not require complete or total expansion or contraction to the fullest possible degree.

In some embodiments, the reservoir 50 is contained entirely within the regulator 30 when the reservoir 50 is in the contracted configuration. In some such embodiments, a cap or other enclosing structure can confine the reservoir 50 within the regulator 30. In some embodiments, the reservoir 50 is partially enclosed within the regulator 30. The enclosing structure and/or regulator 30 can limit or prevent access to (e.g., physical contact with) the reservoir 50 when the reservoir 50 is in the contracted configuration.

In some embodiments, the volume of the reservoir 50 in the contracted configuration is substantially smaller than the volume of the container 10. For example, the volume of the contracted reservoir 50 can be less than or equal to about 20% of the volume within the container 10 and/or greater than or equal to about 2% of the volume within the container 10. In some embodiments, the volume of the contracted reservoir 50 is approximately 5% of the volume of the container 10. The volume of the portion of the regulator 30 in which the contracted reservoir 50 is contained can be approximately equal to the volume of the contracted reservoir 50. In some embodiments, the volume of the portion of the regulator 30 in which the contracted reservoir 50 is contained is greater than or equal to about 105% of the volume of the contracted reservoir 50 and/or less than about 120% of the volume of the contracted reservoir 50.

At least a portion of the reservoir 50 can expand outside of the regulator 30 when the reservoir 50 transitions to the expanded configuration. In some embodiments, as illustrated, substantially all of the volume-enclosing region of the reservoir 50 can move to the exterior of the regulator 30 in the primarily exterior position. The volume of the reservoir 50 in this configuration can be substantially greater than the volume of the reservoir 50 in the contracted configuration. For example, the volume of the reservoir 50 in the expanded configuration can be greater than or equal to about 15% of the volume of the container 10 and/or less than about 70% of the volume of the container 10. In some embodiments, the volume of the expanded reservoir 50 is approximately 50% of the volume of the container 10. Many variations are possible.

FIGS. 3A-3J illustrate an embodiment of a vial adaptor 100. The vial adaptor 100 can include a connector interface 140. The connector interface 140 can be configured to facilitate coupling the vial adaptor 100 with a medical connector (not shown) (e.g., a luer connector or other medical connector), another medical device (not shown), or any other instrument used in extracting fluid from or injecting fluid into a vial (not shown). The vial adaptor 100 can be configured to inhibit or prevent release of vapors or other harmful materials from the vial when the vial adaptor 100 is coupled with the vial.

The vial adaptor 100 can include a body portion 180. The body portion 180 can include a central portion 181. In some embodiments, the central portion 181 is curved. In some embodiments, the body portion includes one or more legs 182 (e.g., which can be opposing). Each or either of the legs 182 can be supported at a proximal end of the leg 182 by the central portion 181 of the body portion 180. In some embodiments, the distal ends of the legs 182 are unrestrained to allow the legs 182 to deflect. The body portion 180 can be removably secured to a vial (not shown). In some embodiments, the body portion 180 includes only a single tab, the single tab configured to removably secure the vial adaptor 100 to the outside surface of the vial and to facilitate the removal of the vial adaptor 100 from the vial.

Figure 3A:
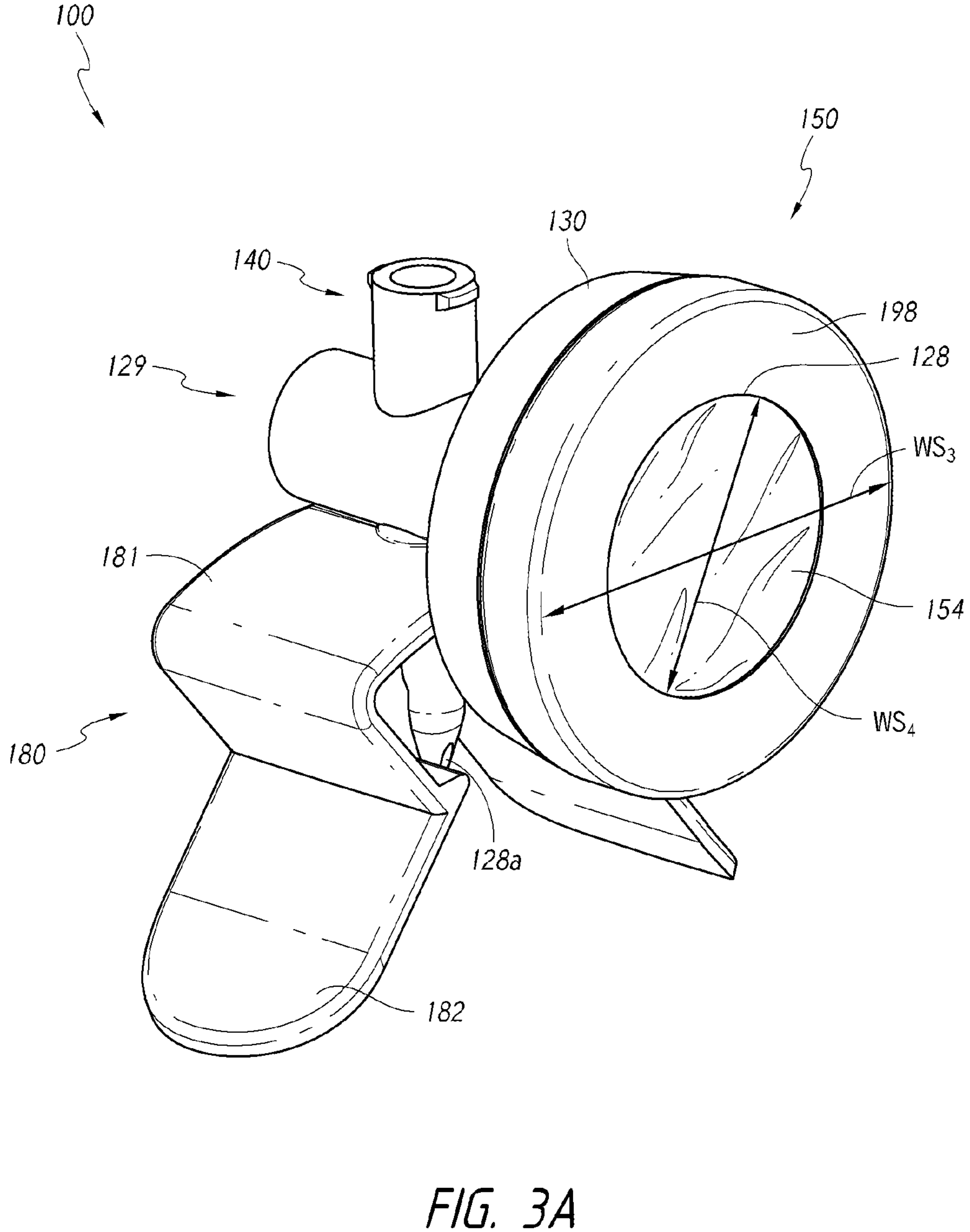
FIG. 3A illustrates a perspective view of another vial adaptor.
Figure 3B:
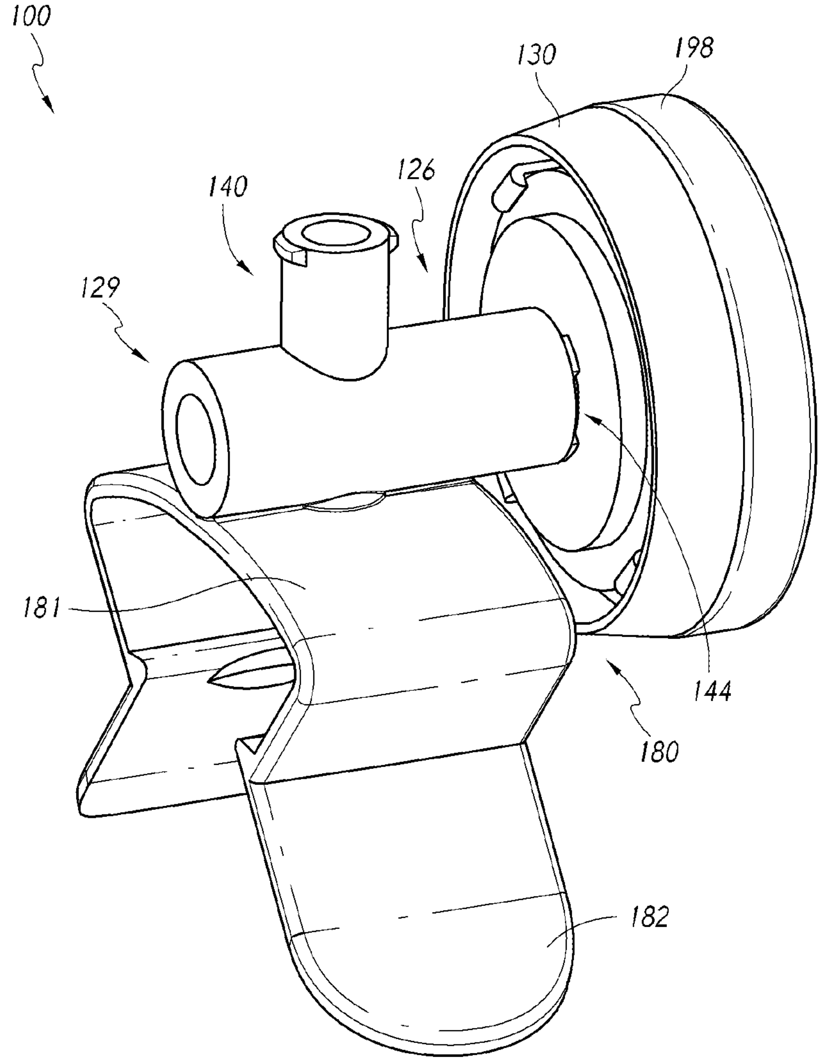
FIG. 3B illustrates another perspective view of the vial adaptor of FIG. 3A.
Figure 3C:
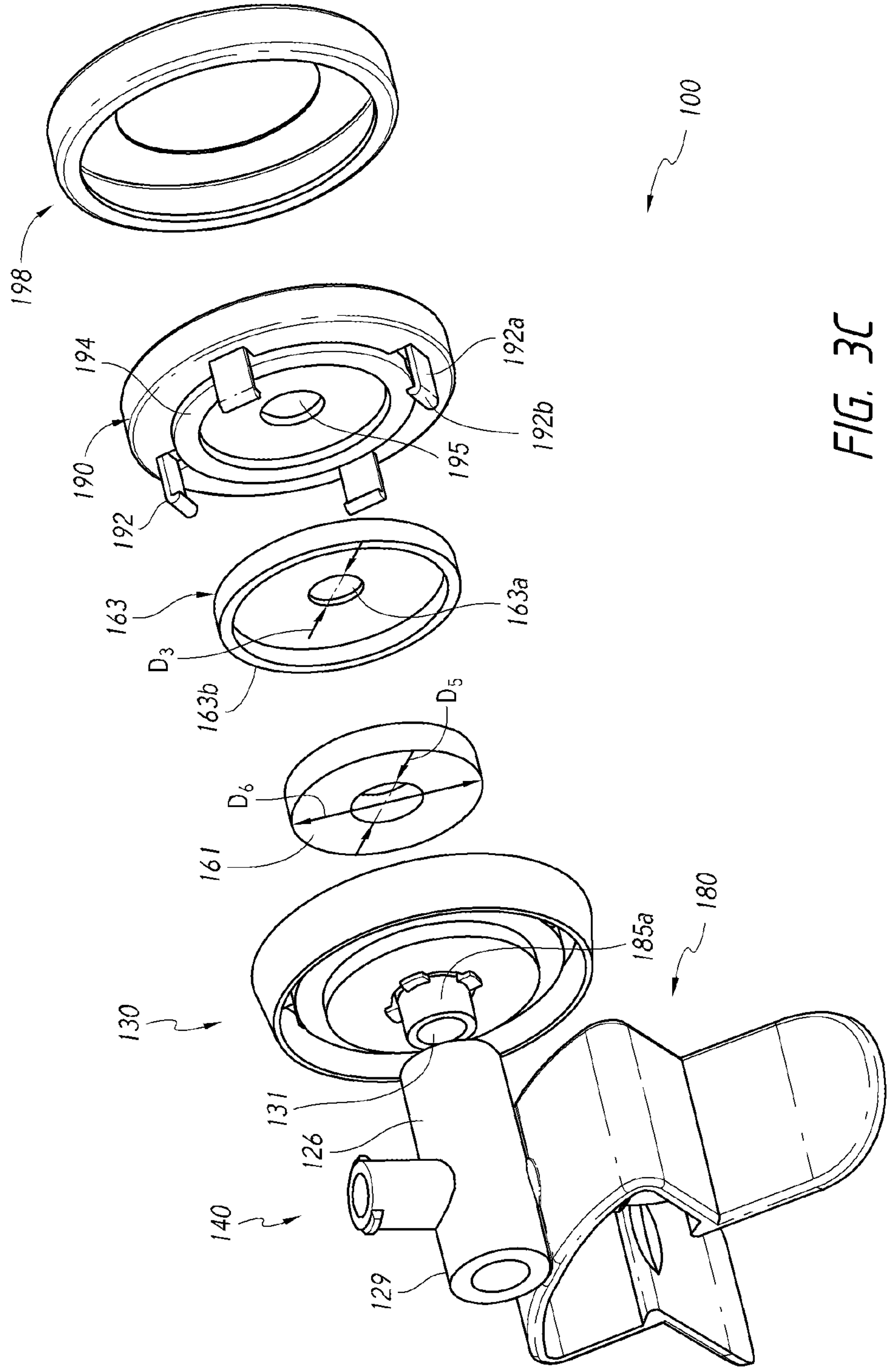
FIG. 3C illustrates an exploded view of the vial adaptor of FIG. 3A.

The vial adaptor 100 can include a piercing member 120. The piercing member 120 can be supported by the body portion 180. The piercing member 120 can project distally from the central portion 181 of the body portion 180. In some embodiments, the piercing member 180 includes an access channel 145 and a regulator channel 125. In some embodiments, the regulator channel 125 begins at a distal regulator aperture 128*a*, passes generally through the piercing member 120, passes through a lumen 126 that extends radially outward from the connector interface 140, and terminates at a proximal regulator aperture 128. In some embodiments, the lumen 126 extends radially outward from the connector interface 140 in only one direction. In some embodiments, the lumen 126 extends radially outward from the connector interface 140 in more than one direction (e.g., in two opposing directions). For example, the lumen 126 can extend through the connector interface 140 to a second lumen 129. Some of the views shown in FIGS. 3A-3J, including FIGS. 3C, 3D, and 3J, do not include an illustration of the flexible enclosure 154 positioned in the storage chamber 196 of the adaptor 100, even though the flexible enclosure 154 is stored in the chamber 196, as shown in FIGS. 3G-3I.

In some embodiments, the regulator assembly 150 includes a regulator base configured to couple (e.g., releasably couple or fixedly couple) with a regulator nest 190. The regulator base 130 can be constructed from a rigid or semi-rigid material. In some embodiments, the regulator base 130 is constructed from a polymer (e.g., a polycarbonate plastic). The regulator base 130 can include a coupling protrusion 185*a*. In some embodiments, the coupling protrusion 185*a* defines a coupling passage 131 (e.g., a regulator assembly channel). The coupling protrusion 185*a* can be configured to couple with the lumen 126 of the vial adaptor 100. For example, the coupling protrusion 185*a* has an outer cross-sectional shape (e.g., a circle, oval, polygon, or other shape) sized and shaped to generally match an interior cross-section of a lumen 126 of the vial adaptor 100. In some embodiments, the coupling protrusion 185*a* can be configured to friction-fit into the lumen 126. In some embodiments, one or more attachments are used, such as one or more sonic welds, glues, or adhesives, to affix the coupling protrusion 185*a* to the lumen 126. As illustrated in FIG. 3G, coupling passage 131 can be in fluid communication with the regulator channel 125 of the vial adaptor 100 when the coupling protrusion 185*a* is coupled with or otherwise associated with the lumen 126. For example, the coupling protrusion 185*a* may be coupled with a proximal passageway (e.g., proximal regulator passageway) defined by a portion of the regulator channel 125 between the valve 170 and the proximal end of the lumen 126. In some embodiments, the regulator assembly 150 does not include a valve in the regulator channel 125 or in the lumen 131.

Figure 3D:
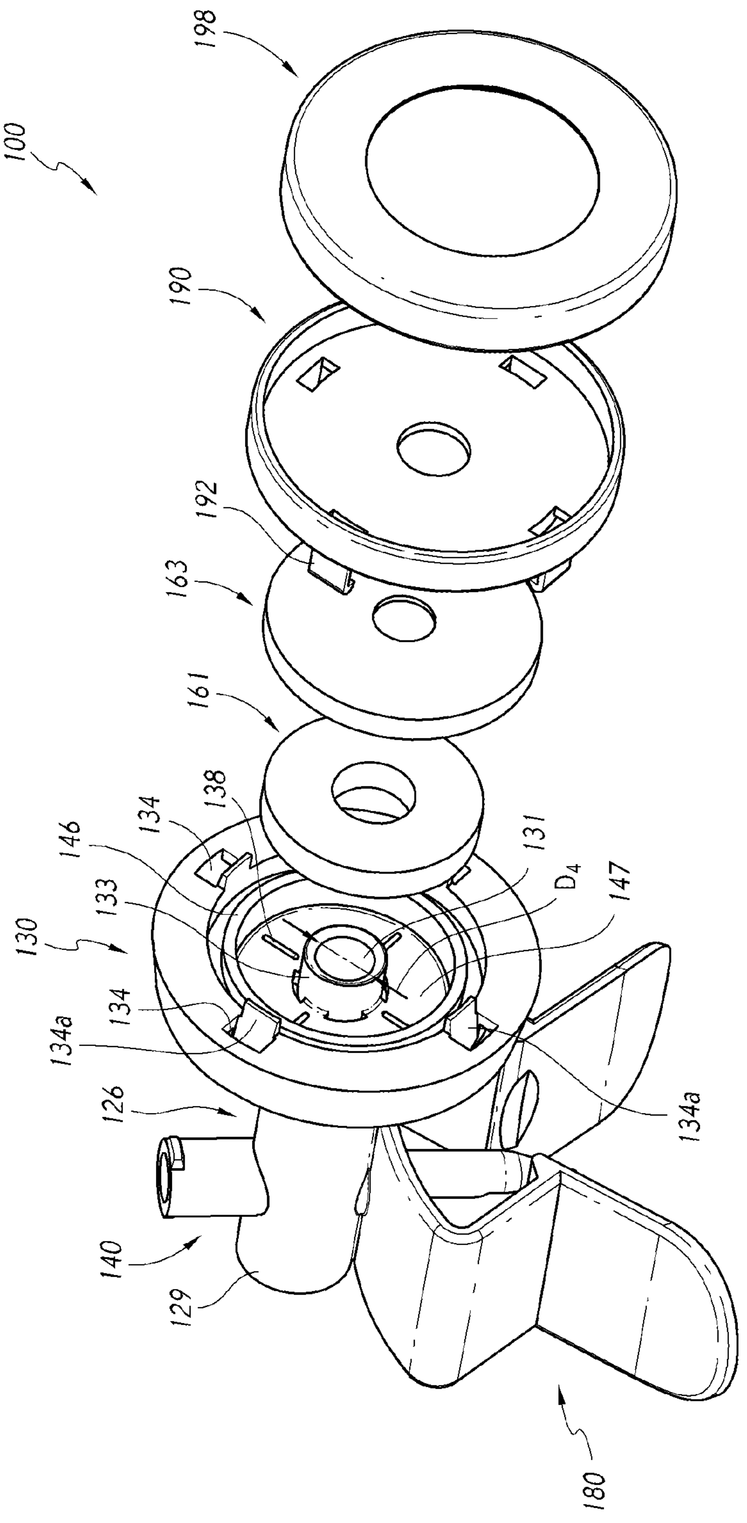
FIG. 3D illustrates another exploded view of the vial adaptor of FIG. 3A.
Figure 3F:
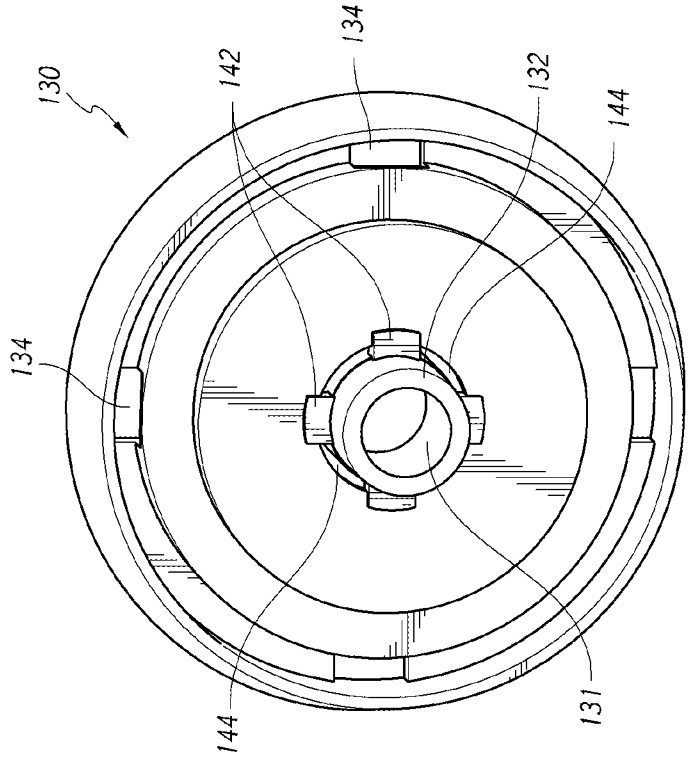
FIG. 3F illustrates another perspective view of the regulator base of FIG. 3E.
Figure 3E:
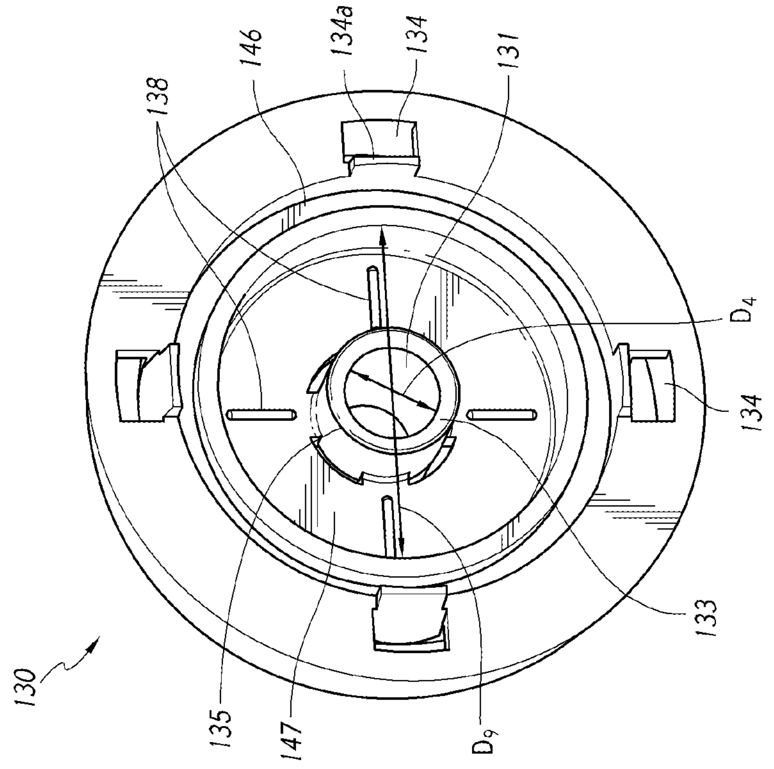
FIG. 3E illustrates a perspective view of a regulator base of the vial adaptor of FIG. 3A.
Figure 3G:
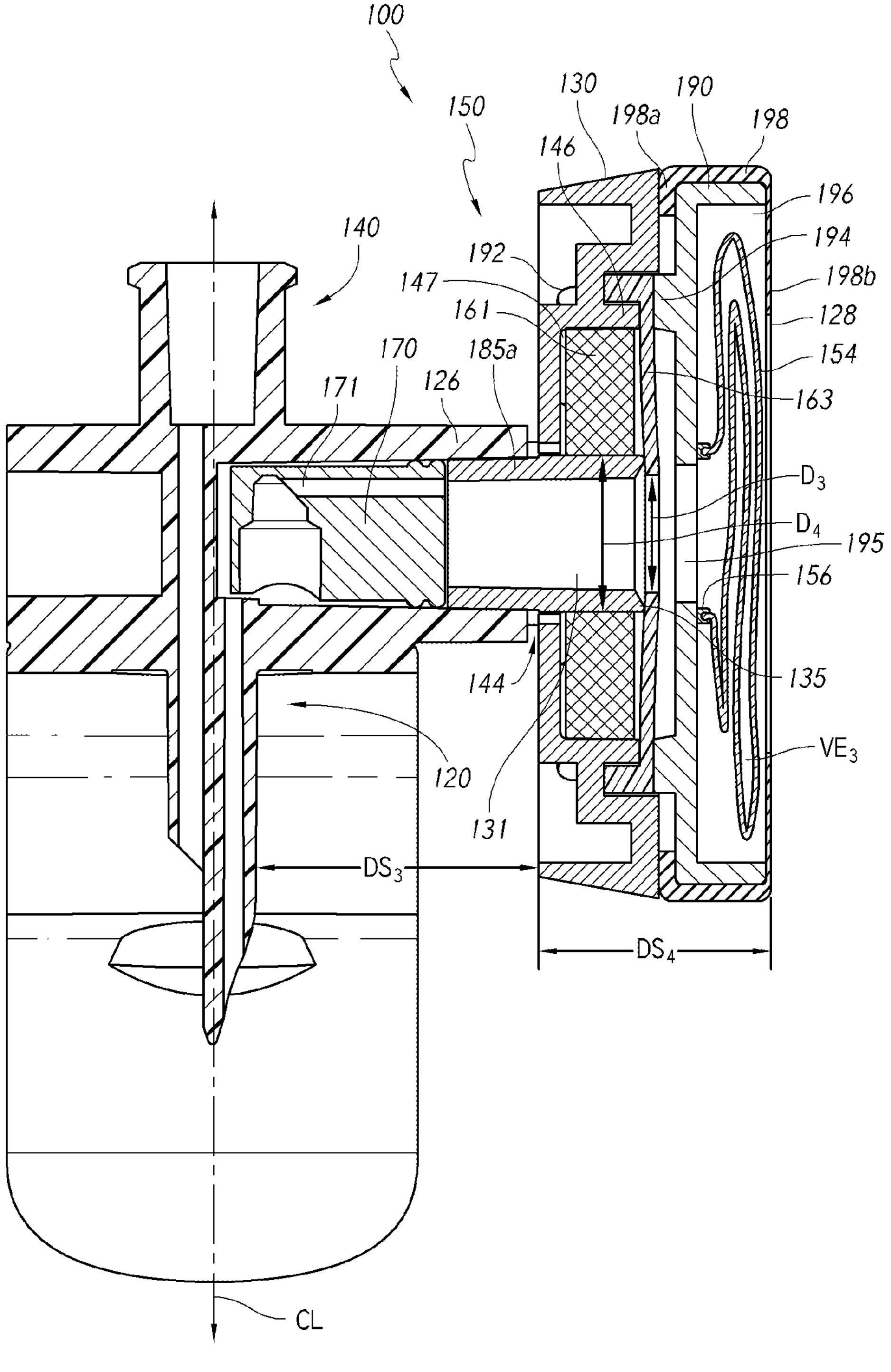
FIG. 3G illustrates a front partial cross-sectional view of the vial adaptor of FIG. 3A.
Figure 3H:
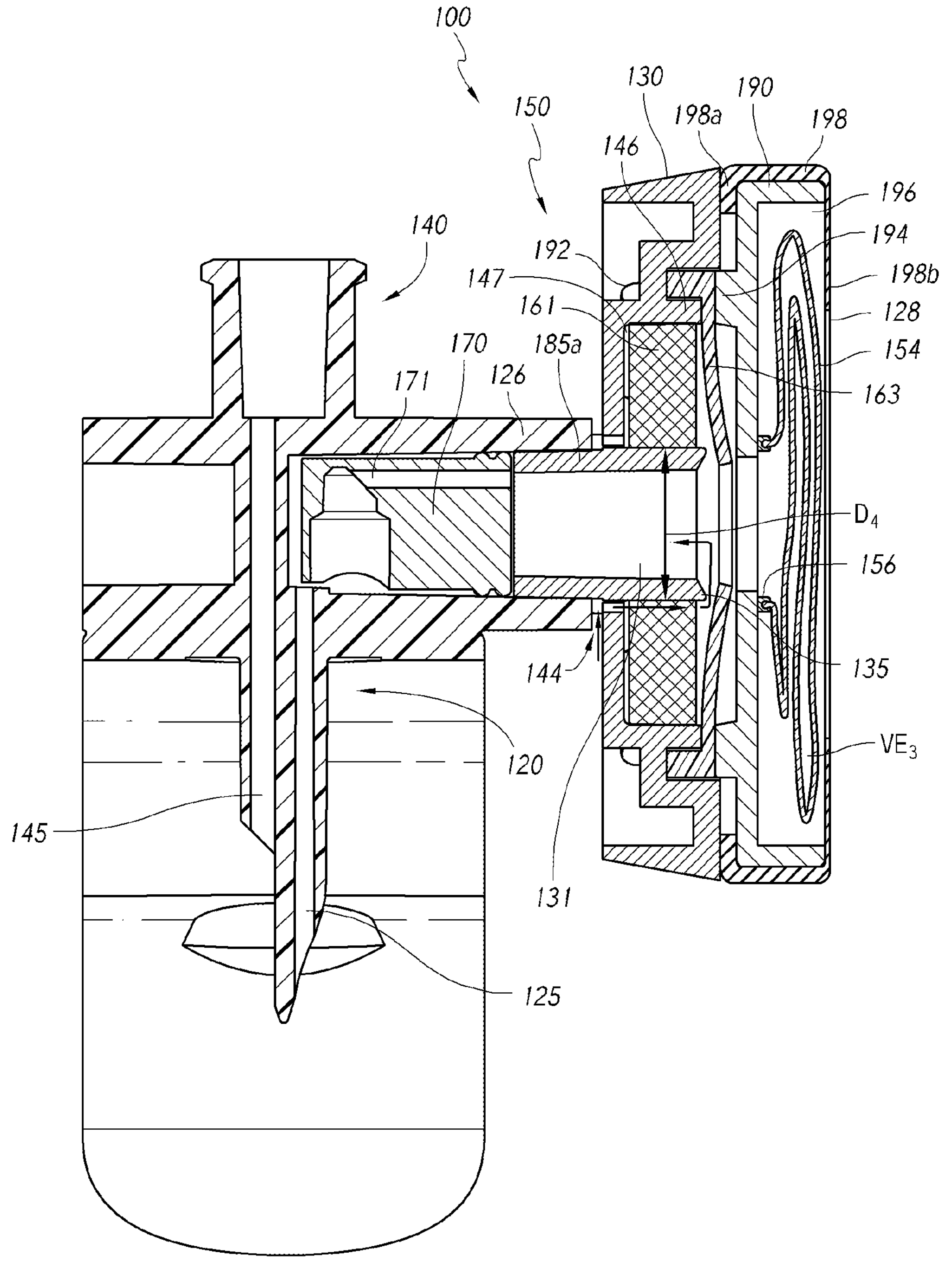
FIG. 3H illustrates a front partial cross-sectional view of the vial adaptor of FIG. 3A with the diaphragm check valve in an open position.
Figure 31:
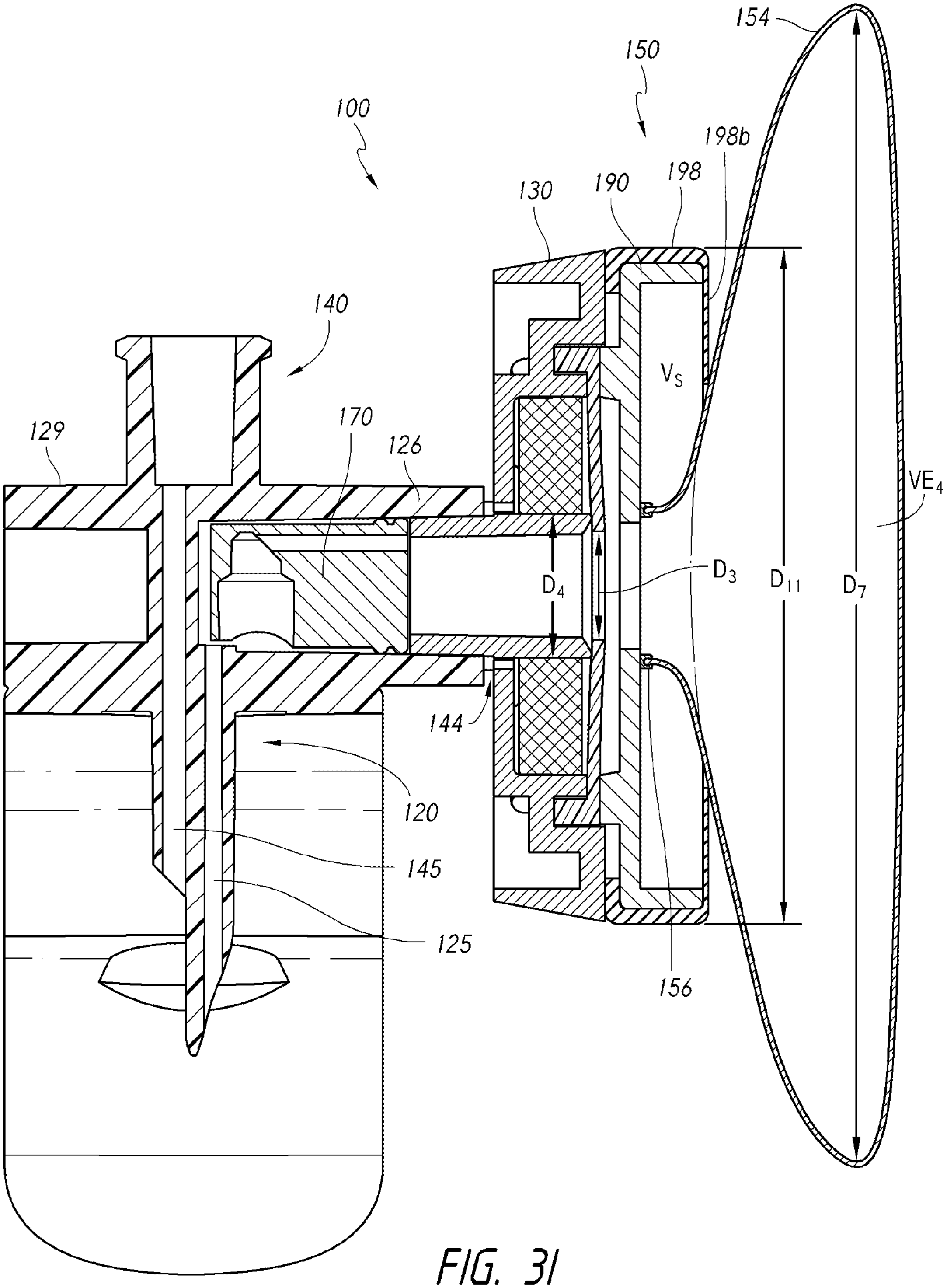
Figure 3J:
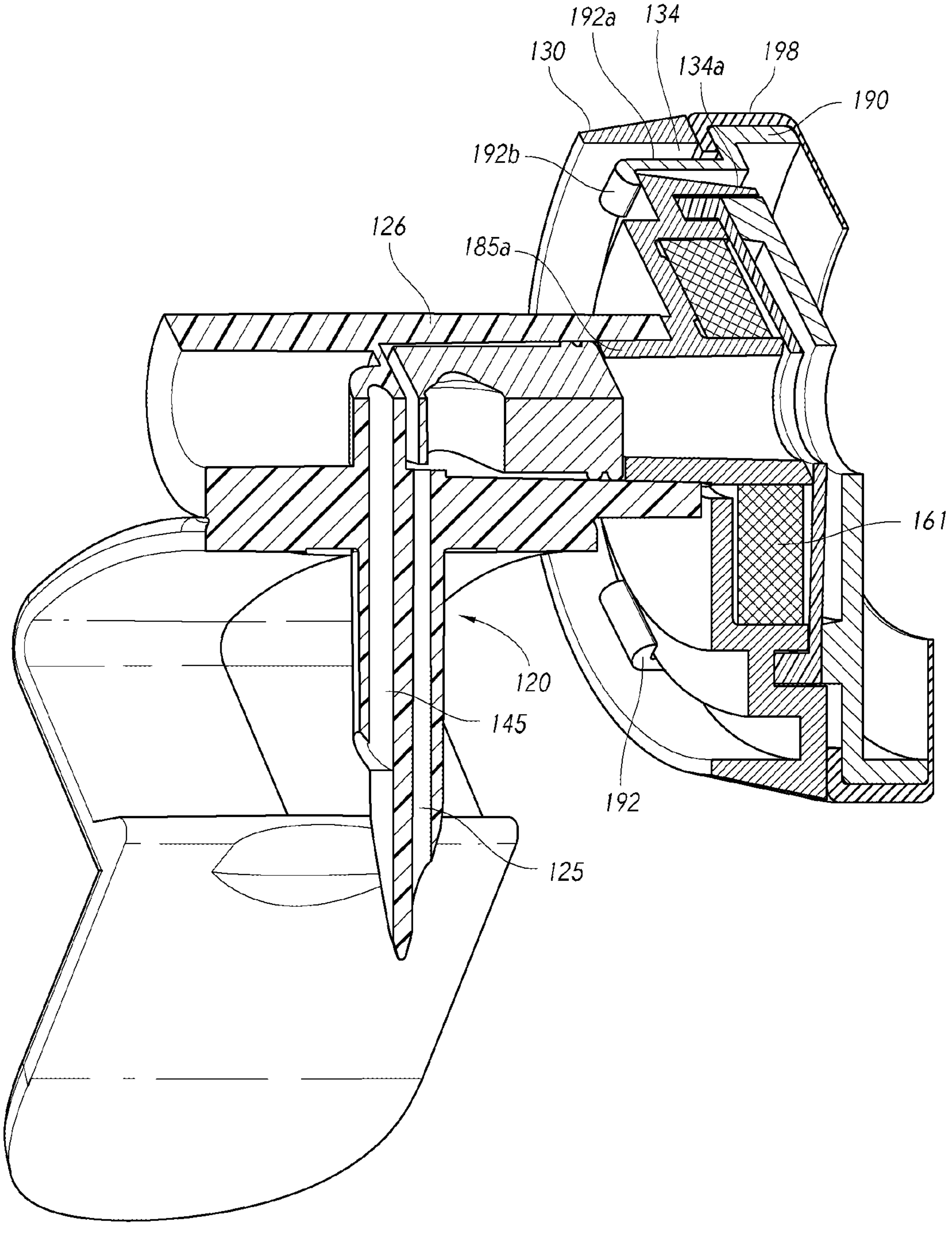
FIG. 3J illustrates a partial perspective cross-sectional view of the vial adaptor of FIG. 3A.

As illustrated in FIG. 3D, the regulator base 130 can include a base protrusion 133 that extends from the regulator base 130 in a direction generally opposite from the direction in which the coupling protrusion 185*a* extends. The base protrusion 133 can have an outer width (e.g. an outer diameter) D4. An inner wall of the base protrusion 133 can comprise a portion of the coupling passage 131. The regulator base 130, in some embodiments, can include an axial projection 146. The axial projection 146 can extend from the regulator base 130 in the same direction as the base protrusion 133. The axial projection 146 can, in some embodiments, have a generally annular shape. In some embodiments, the axial projection 146 has a generally oval shape, generally polygonal shape, generally circular shape, or any other appropriate shape.

In some embodiments, a filter cavity 147 (e.g., filter chamber) can be positioned in a space between the base protrusion 133 and the axial projection 146 (e.g., surrounding a portion of the lumen 131). The inner width of the filter cavity 147 can be the width D4 of the base protrusion 133 (e.g., the inner wall of the filter cavity 147 can have a width D4). The outer width D9 of the filter cavity 147 can be the inner width of the axial projection 146 (e.g., the outer wall of the filter cavity 147 can have a width substantially equal to the width of the axial projection 146). In some embodiments, the filter cavity 147 has a generally toroidal shape. The word "toroidal" is used herein in its broad and ordinary sense and includes, for example, toroidal shapes (e.g., tori, rectangular toroids, polygonal toroids), irregular toroidal shapes (e.g., toroids with protrusions, non-circular shapes, notches, cutouts, etc.), or any combination thereof. In some embodiments, the filter cavity 147 has a generally square, generally rectangular, generally triangular, generally oval shape, or other shape.

A filter 161 can be sized to fit within the filter cavity 147. The filter 161 can have an inner width (e.g., diameter) D5 configured to be less than or equal to about the inner width D4 of the filter cavity 147. In some embodiments, the inner width D5 of the filter 161 is greater than the inner width D4 of the filter cavity 147. In some embodiments, the filter 161 has an outer width (e.g., diameter) D6 that is greater than or equal to about the outer width D9 of the filter cavity 147. The filter 161 can be a hydrophobic and/or an antibacterial filter. In some embodiments, the filter 161 is constructed from a paper, polymer, foam, or other material, such as a light-weight porous material. In some embodiments, the filter 161 is constructed from a flexible or semi-flexible material. The filter 161 can be configured to deform when inserted into the filter cavity 147. For example, the inner width D5 of the filter 161 can fit snugly onto or stretch onto the width D4 of the base protrusion 133. In some embodiments, the outer width D6 of the filter 161 fits snugly against or is compressed into the outer width D9 of the filter cavity 147. In some embodiments, a snug fit between the filter 161 and the filter cavity 147 can inhibit fluid from flowing into and/or out of the filter cavity 147 and/or coupling channel 131 without going through the filter 161.

The regulator assembly 150 can include a diaphragm 163. The diaphragm 163 can, in some embodiments, have a generally circular or generally annular shape (e.g., a generally toroidal shape, as illustrated). In some embodiments, the shape of the diaphragm 163 is configured to generally match the shape of the axial projection 146 of the regulator base 130. The diaphragm 163 can be inserted into or onto the base portion 130. For example, a lip 163*b* of the diaphragm 163 can be configured to fit around the radial (e.g., up and down in FIG. 3H) outside of the axial projection 146. The diaphragm 163 can include an inner aperture 163*a* (e.g., an orifice defined by an inner perimeter, as illustrated) having a width (e.g., a diameter) D3. For example, the inner aperture 163*a* may have a generally circular shape. In some embodiments, as illustrated, the width D3 can be less than the outer width D4 of the base protrusion 133. In some embodiments, as illustrated, the diaphragm 163 is positioned generally coaxially with the base protrusion 133. In some embodiments, the diaphragm 163 is positioned generally coaxially with the coupling passage 131, as illustrated. In some embodiments, as illustrated, the inner aperture 163*a* (e.g., orifice or inner orifice) of the diaphragm 163 comprises a portion of the regulator assembly channel 131.

The regulator nest 190 can be configured to releasably or otherwise couple with the regulator base 130. As illustrated in FIG. 3C, the regulator nest 190 can include one or more fixation members 192. The fixation members 192 can be constructed and/or configured to engage with fixation apertures 134 on the regulator base 130. The fixation members 192 can comprise clips, tabs, or other projections configured to insert into the fixation apertures 134 of the regulator base 130. For example, the fixation members 192 can comprise a tab 192*a* with a hook 192*b* on the end. The fixation members 192 can be constructed from a resilient material. For example, tabs 192*a* of the fixation members 192 can be configured to deform (e.g., deflect) or otherwise move when a radial (e.g., up and down with respect to FIG. 3H) force is applied to the hooks 192*b*. The regulator base 130 can include angled tabs 134*a* configured to deflect the hooks 192*b* radially (e.g., up and down with respect to FIG. 3H) outward as the tabs 192*a* are inserted into the apertures 134. The hooks 192*b* can snap back in place upon passing through the fixation apertures 134 and can engage with the rear side (e.g., the side away from the regulator nest 190) of the angled tabs 134*a* to secure the regulator nest 190 to the regulator base 130.

As illustrated in FIG. 3G, the regulator nest 190 can include an axial projection 194. The axial projection 194 can extend from the regulator nest 190 toward the regulator base 130 when the regulator nest 190 is coupled with the regulator base 130. The axial projection 190 can, in some embodiments, have a generally annular shape. In some embodiments, the axial projection 194 has a generally oval shape, a generally polygonal shape, a generally circular shape, or any other appropriate shape. The shape of the axial projection 194 can be similar to or the same as the shape of the axial projection 146 of the regulator base 130. As illustrated, the axial projection 194 can contact at least a portion of the diaphragm 163 as the regulator nest 190 is coupled with the regulator base 130. In some embodiments, contact between the axial projection 194 of the regulator nest 190 and the diaphragm 163 can secure at least a portion of the diaphragm 163 in position between the axial projection 194 and the axial projection 146 of the regulator base

130. For example, the axial projections 146, 194 can secure in position a portion of the diaphragm 163 adjacent to or near the lip 163*b*.

As illustrated, in some embodiments the base protrusion 133 can extend further than the axial projection 146 in the direction away from the coupling protrusion 185*a*. In some embodiments, a portion of the diaphragm 163 adjacent the inner aperture 163*a* can be deflected or otherwise moved away from the coupling protrusion 185*a* when the regulator nest 190 is coupled to the regulator base 130. Deflection of the portion of the diaphragm 163 adjacent the inner aperture 163*a* can create a biasing force (e.g., a return force within the material of the diaphragm 163) that can bias the inner aperture 163*a* of the diaphragm 163 toward a lip 165 (e.g., the end of the base protrusion 133 furthest from the regulator base 130, as illustrated in FIG. 3H) of the base protrusion 133. The lip 165 of the base protrusion 133 can be formed with a configuration to help produce a low amount of interface or surface area of contact on its forward edge (such as an angled or beveled configuration). For example, a valve seat 135 can be formed on or near the radially (e.g., up and down with respect to FIG. 3H) outward portion of the base protrusion 133. Engagement between the diaphragm 163 and the valve seat 135 can form a one-way diaphragm valve (e.g., a diaphragm check valve or intake valve, as illustrated) as will be described in more detail below. The valve seat 135 can be located further from the coupling protrusion 185*a* than a radially (e.g., up and down with respect to FIG. 3H) inward portion of the lip 165. In some embodiments, a beveled lip can inhibit or prevent the diaphragm 163 from sticking to the valve seat 135 by producing a low amount of surface area contact or interface between the diaphragm 163 and the valve seat 135.

In some embodiments, the vial adaptor 100 includes an expansion inhibitor, such as an enclosure cover 198. The expansion inhibitor can inhibitor or resist or prevent the expansion or movement of the flexible enclosure 154 within or away from the regulator nest. In some embodiments, the enclosure cover 198 is configured to cover or obscure or retain all of a flexible enclosure 154 within the regulator assembly 150 or to cover or obscure or retain all of the flexible enclosure 154 and a front region of the regulator assembly 150. In some embodiments, the expansion inhibitor or enclosure cover 198 does not cover or obscure or retain all of the flexible enclosure 154. The enclosure cover 198 can be constructed from a resilient, flexible, or semi-flexible material. For example, the enclosure cover 198 can be constructed from rubber, silicone, and/or some other flexible or semi-flexible material. The enclosure cover 198 can be sized and shaped to fit around the radially (e.g., up and down with respect to FIG. 3H) outward portion of the regulator nest 190. For example, as illustrated in FIG. 3G, the enclosure cover 198 can include an inner lip 198*a* configured to wrap around one axial side (e.g., the axial side of the regulator nest 190 closest to the regulator base 130 in the assembled regulator assembly 150) of the regulator nest 190 and an outer lip 198*b* configured to wrap around the other axial side of the regulator nest 190. As illustrated, the inner lip 198*a* can be about the same thickness as or thicker than the outer lip 198*b*. In some embodiments, the inner lip 198*a* of the regulator enclosure cover 198 can be positioned or wedged between the regulator nest 190 and the regulator base 130 when the regulator nest 190 is coupled with the regulator base 130. In some embodiments, wedging the inner lip 198*a* of the enclosure cover 198 can inhibit or prevent the enclosure cover 198 from detaching from the regulator nest 190. In some embodiments, adhesives can be used to adhere the enclosure cover 198 to the regulator nest 190. The outer lip 198*b* of the enclosure cover 198 can include or define an expansion aperture 128. For example, the outer lip 198*b* can define a circular or otherwise shaped opening to define the expansion aperture 128. The expansion aperture 128 can have a width WS4 that is less than a width WS3 of the regulator nest 190.

As illustrated in FIG. 3G, the vial adaptor 100 can include a flexible enclosure 154. The flexible enclosure 154 can be configured to fit within a storage chamber 196 within the regulator nest 190 and/or the enclosure cover 198. In some embodiments, the flexible enclosure 154 is folded into the storage chamber 196 when the flexible enclosure 154 is in a contracted configuration. In some embodiments, as illustrated, the flexible enclosure 154 is not generally expandable by stretching the material of the flexible enclosure 154 in the plane of such material, to avoid creating an opposing pressure against the expansion which would tend to encourage gas within the flexible enclosure 154 to be urged back out of the flexible enclosure 154. Rather, by primarily unfolding instead of primarily stretching the flexible enclosure 154 to increase its volume, the gas inside of the flexible enclosure 154 is not generally urged back out of the flexible enclosure 154 unless and until one or more other forces in the system act upon it to do so. The flexible enclosure 154 can be connected to the regulator nest 190 at an attachment point 156. For example, an adhesive (e.g., glue, tape, foam tape or other appropriate adhesive) can be used to attach an opening of the flexible enclosure 154 to the regulator nest 190. The flexible enclosure 154 can be connected and/or coupled with the regulator nest 190 in a fluid tight fashion. For example, the flexible enclosure 154 can define an inner volume VE1, VE2 in communication with the coupling passage 131 of the regulator base 130. In some embodiments, the interior volume VE1, VE2 of the flexible enclosure 154 is not in fluid communication with ambient when the diaphragm check valve is in the closed position.

In some embodiments, as illustrated in FIG. 3H, the regulator assembly 150 can include one or more intake ports 144. The intake ports 144 can be positioned along or near the coupling protrusion 185*a*. In some embodiments, the intake ports 144 are positioned in a wall of the regulator base 130 away from the coupling protrusion 185*a*. One or more spacers 144*a* can be located adjacent to the intake ports 144. The spacers 144*a* can be configured to limit the extent to which the coupling protrusion 185*a* enters into the lumen 126 when the regulator base 130 is coupled with the lumen 126. In some embodiments, the spacers 144*a* inhibit or prevent intake ports 144 from being blocked by the regulator base 130 and/or the lumen 126.

As illustrated in FIG. 3G, the intake ports 144 can facilitate communication between ambient and the filter 161. In some embodiments, upon withdrawal of fluid from a vial onto which the vial adaptor 100 is attached, a pressure deficit can be realized in the coupling passage 131. A reduction in pressure in the coupling passage 131 can create a pressure differential at the interface between the valve seat 135 and the diaphragm 163. In some embodiments, the diaphragm 163 is configured to deflect or otherwise move away from the valve seat 135 when a predetermined pressure differential (e.g., a pressure differential wherein the pressure in the coupling passage 131 is lower than the ambient pressure) is applied across the diaphragm 163. As shown in FIG. 3H, deflection or other movement of the diaphragm 163 away from the valve seat 135 (e.g., transition of the diaphragm or intake valve to the opened configuration, as illustrated) can facilitate fluid communication between ambient and the coupling passage 131 (e.g., fluid flow into the interior of the regulator assembly 150 between the valve seat 135 and the inner perimeter of the valve member 163 comprising the inner aperture 163*a*, as illustrated). In some embodiments, fluid communication between ambient and the coupling passage 131 can help to equalize the pressure between the interior of the vial 10 and ambient. Fluid passing from ambient to the coupling passage 131 can pass through the filter 161. In some embodiments, the filter 161 can inhibit or prevent introduction of contaminants (e.g., bacteria, viruses, particulates) into the coupling passage 131 when the diaphragm check valve is open (e.g., when the diaphragm 163 is disengaged from the valve seat 135). The diaphragm 163 can be configured to return to its engagement with the valve seat 135 (e.g., the closed configuration of the diaphragm or intake valve) when a predetermined pressure differential (e.g., generally equal pressure, or some other pressure differential) occurs between the interior of the vial (e.g., the coupling passage 131) and ambient.

In some embodiments, a health care practitioner may withdraw fluid from the vial 10 in a vented manner via the access channel 145 after coupling the vial adaptor 100 with the vial 10 both prior to and after injecting fluid into the vial 10 via the access channel 145. For example, a diaphragm check valve formed by the diaphragm 163 and the valve seat 135 can permit fluid withdrawal from the vial 10 via the access channel 145 in a vented manner (e.g., in a manner that maintains a pre-determined pressure range within the vial 10 during withdrawal of fluid) prior to expansion of the flexible enclosure 154 by permitting fluid ingress through the intake ports 144 through the filter 161. In some embodiments, the gas pressure within the vial is maintained at a generally equal level with ambient air pressure so that fluid within a withdrawing medical implement (such as a syringe connected to the vial adapter) is not unintentionally drawn back into the vial and so that the risk of microspraying, gas release, or other undesirable occurrences during connection or disconnection are substantially reduced or eliminated.

In some embodiments, upon introduction of fluid into the vial 10 via the access channel 145, an increase in pressure can be realized within the coupling passage 131. The volume within the flexible enclosure 154 can be configured to expand in response to an increase in pressure within the coupling passage 131 to a desirable or predetermined pressure. For example, upon introduction of fluid into the vial via the access channel 145, the pressure in the coupling channel 131 can increase to a point that the volume within the flexible enclosure 154 expands to the expanding configuration, as illustrated in FIG. 3I. In the expanded configuration, the flexible enclosure can have a width (e.g., a diameter) D7 (e.g, an expanded width or deployed width). The width D7 of the flexible enclosure 154 can be greater than a width (e.g., a diameter) D11 of the regulator nest 190. For example, the width D7 can be greater than or equal to about 110% of the width D11 and/or less than or equal to about 500% of the width D11. In some embodiments, the width D7 of the expanded flexible enclosure 154 is approximately 320% of the width D11 of the regulator nest 190. As shown in the example illustrated in FIG. 3I, the width D11 of the regulator nest 190 can be about the same as or less than the distance between the proximal end of the connector interface 140 and the distal end of the piercing member 120, and/or the width D11 of the regulator nest 190 can be about the same as or less than the distance between the proximal end of the connector interface 140 and the distal end of a connection portion 120 of the vial adaptor 100 that is adapted to grasp a portion of the vial, and/or the width D11 of the regulator nest 190 can be less than a distance between the connector interface 140 and the distal regulator aperture 128*a*. The expanded volume VE4 of the flexible enclosure 154 can be greater than the storage chamber volume VS of the storage chamber 196. For example, the expanded volume DE4 of the flexible enclosure 154 can be greater than or equal to about 500% of the volume VS of the storage chamber 196 and/or less than or equal to about 10,000% of the volume VS of the storage chamber 196. In some embodiments, the expanded volume VE4 of the expanded flexible enclosure 154 is greater than or equal to about 3,000% of the volume VS of the storage chamber 196 and/or less than or equal to about 5,500% of the volume VS of the storage chamber 196. In some embodiments, the expanded volume VE4 of the expanded flexible enclosure 154 is approximately about 4,300% of the volume VS of the storage chamber 196. Many variations are possible.

The volume within the flexible enclosure 154, after transition to the expanded configuration, can be configured to contract to the contracted configuration upon withdrawal of fluid from the vial 10 via the access channel 145. Contraction of the volume within the flexible enclosure 154 can facilitate introduction of regulator fluid from the interior volume of the flexible enclosure 154 to the vial 10 via the regulator channel 125. (e.g., through the proximal regulator passageway and through a distal passageway of the regulator channel 125 between the valve 170 and the distal regulator aperture 128*a*, as illustrated). Introduction of regulator fluid from the interior volume of the flexible enclosure 154 to the vial 10 can facilitate maintenance of the pressure within the vial 10 within a desirable or predetermined range.

As illustrated in FIG. 3G, a radial (e.g., with respect to the centerline CL of the piercing member 120) distance DS3 between the regulator base 130 and the center line of the vial adaptor 100 can be greater than the radial distance DS4 between the radially inner edge of the regulator base 130 and the radially outward edge of the enclosure cover 198. In some embodiments, the radial distance DS3 is greater than or equal to 110% of the radial distance DS4 and/or less than or equal to 200% of the radial distance DS4. In some embodiments, the radial distance DS3 is approximately 140% of the radial distance DS4.

In some embodiments, the flexible enclosure 154 is folded and stored within the storage chamber 196 when the flexible enclosure 154 is in the contracted configuration. In some embodiments, the flexible enclosure 154 is folded into a polygonal shape, circular shape, and/or oval shape before being stored in the storage chamber 196. For example, as illustrated in FIG. 4B, the flexible enclosure 154 can be folded into a substantially rectangular shape within the storage chamber 196.

As discussed above, the flexible enclosure 154 can be configured to transition to an expanded configuration upon introduction of fluid into the vial 10 via the access channel 145. In some embodiments, the flexible enclosure 154 is folded and stored within the storage chamber 196 such that at least a portion of the flexible enclosure 154 realizes a frictional resistance with a portion of the outer lip 198*b* of the enclosure cover 198 as the flexible enclosure 154 transitions to the expanded configuration from the contracted configuration. Frictional resistance between the folded flexible enclosure 154 and the outer lip 198*b* can inhibit or prevent the flexible enclosure 154 from rapidly transitioning to the expanded configuration. Slowing the transition of the flexible enclosure 154 from the contracted configuration to the expanded configuration can inhibit or prevent the check valve 170 from accidentally closing and can generally help diminish stresses within the system of the vial, the vial adaptor, and the medical implement (e.g., syringe) to which vial is being transferred, that may otherwise increase the risk of leaking or other failures.

In some embodiments, the flexible enclosure 154 is configured to unfold from the contracted configuration in a consistent and/or controlled manner in order to promote a consistent, slow, and predictable expansion of the volume within the flexible enclosure 154. For example, the flexible enclosure 154 can be folded in a desirable or predetermined pattern (e.g., the patterns disclosed in FIGS. 5A-6B and described below) and unfolded in a desirable or predetermined pattern (e.g., the folds made in the folding pattern unfold in the reverse order from the order in which they were folded).

In some embodiments, the flexible enclosure 154 is folded into the storage chamber 196 such that the folds of the flexible enclosure 154 form a generally laminate substrate of enclosure layers. For example, as illustrated in FIG. 3G, a plurality of flexible enclosure layers can be positioned between a nest aperture 195 of the regulator nest 190 and the expansion aperture 128 of the outer lip 198*b* of the enclosure cover 198. In some embodiments, the flexible enclosure layers can substantially reduce, minimize, or eliminate the likelihood of material failure (e.g., puncture, tearing, rupture) of the flexible enclosure 154 from impact or other external forces on the layer of the folded flexible enclosure 154 closest to the expansion aperture 128 (e.g., the layer of the folded flexible enclosure 154 most exposed to ambient when the flexible enclosure 154 is in the contracted configuration). For example, the laminate configuration of the folds of the folded flexible enclosure 154 can increase the effective thickness (e.g., the sum thickness of the laminate layers) of the flexible enclosure 154 layers with respect to impact or other forces applied from the exterior of the regulator assembly 150. In some embodiments, the laminate configuration of the folded flexible enclosure 154 can reduce, minimize, or eliminate any likelihood that the flexible enclosure 154 would rupture due to increased pressure from within the vial 10. For example, as described above, the laminate layers can increase the effective thickness of the flexible enclosure 154 with respect to pressure within the vial 10.

As illustrated in FIG. 3G, the flexible enclosure 154 can have a very small internal volume VE3 when in the contracted configuration. For example, folding the flexible enclosure 154 (e.g., according to the processes described below) can diminish the space between the laminate folded layers of the folded flexible enclosure 154 and can eject much or most of the fluid from within the flexible enclosure 154. In some embodiments, ejecting much or most of the fluid from the folded flexible enclosure 154 can increase the volume difference between the contracted flexible enclosure 154 (e.g., as shown in FIG. 3G) and the expanded flexible enclosure 154 (e.g., as shown in FIG. 3I). In some embodiments, increasing the volume difference between the contracted flexible enclosure 154 and the expanded flexible enclosure 154 can reduce, minimize, or eliminate any need to use a stretchable material for the flexible enclosure 154. For example, a flexible material with little or no stretchability (e.g. Mylar® film) can be used to construct the flexible enclosure 154. In some embodiments, the flexible enclosure 154 is constructed from polyethylene or some other appropriate material.

Figure 4A:
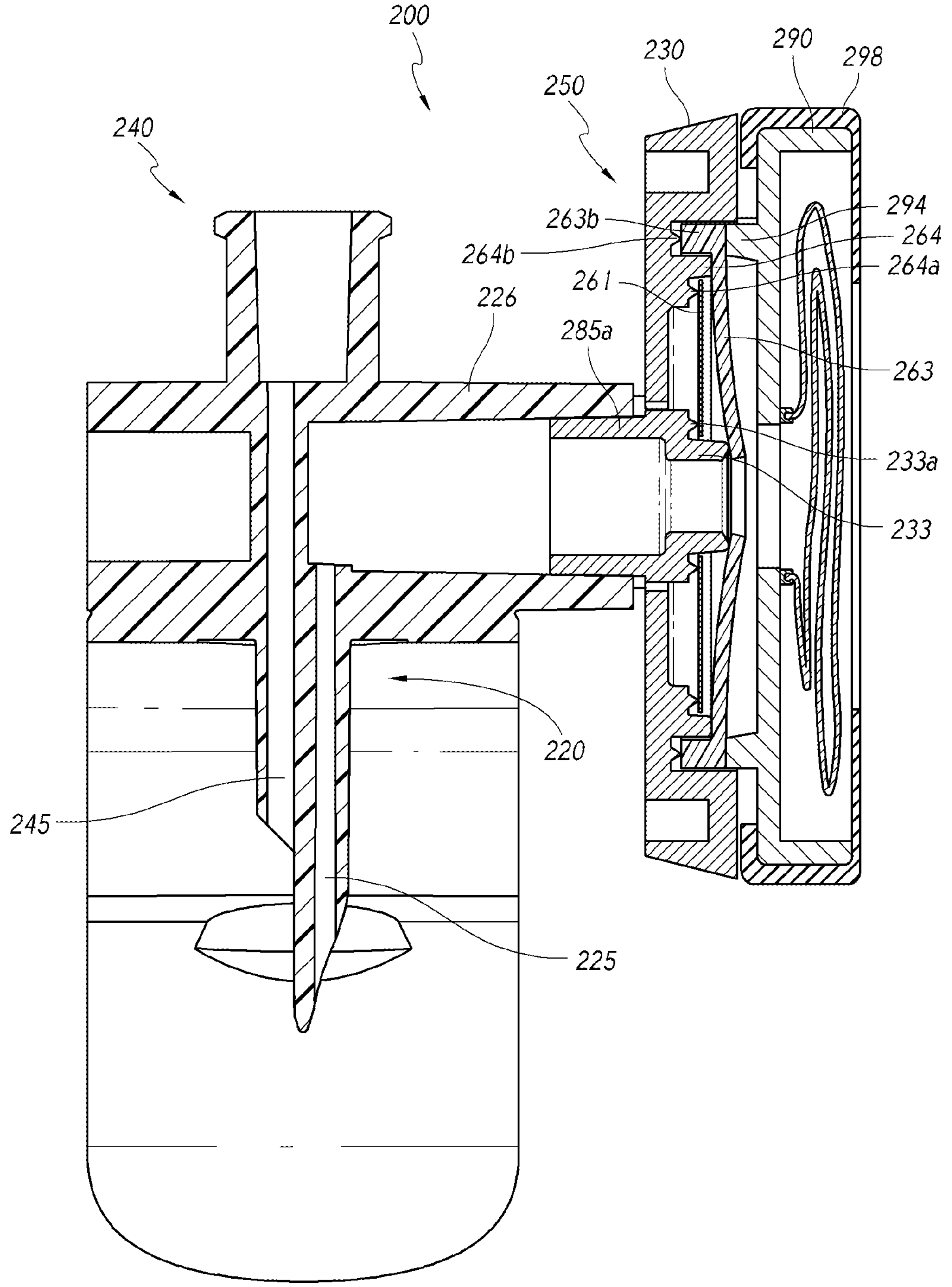
FIG. 4A illustrates a front partial cross-sectional view of another vial adaptor.
Figure 4B:
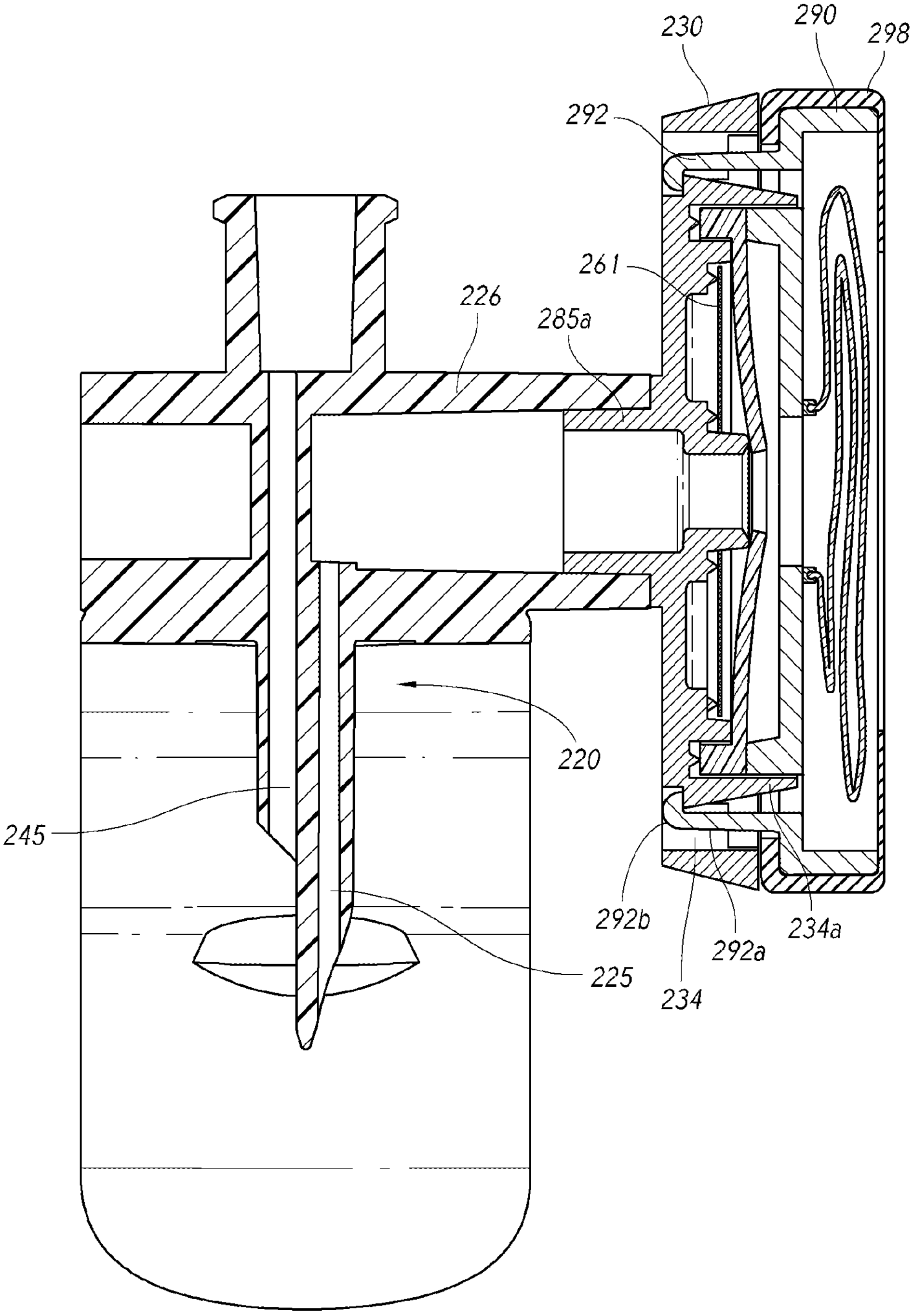
FIG. 4B illustrates a front partial cross-sectional view of the vial adaptor of FIG. 4A with the regulator assembly rotated about its axis by 45°.

FIGS. 4A-4B illustrate an embodiment of a vial adaptor 200 that can have components or portions that are the same as or similar to the components or portions of other vial adaptors disclosed herein. In some embodiments, the vial adaptor 200 includes a connector interface 240 and a piercing member 220 in partial communication with the connector interface 240. In some embodiments, the vial adaptor 200 includes a regulator assembly 250. Some numerical references to components in FIGS. 4A-4B are the same as or similar to those previously described for the vial adaptor 100 (e.g., piercing member 220 v. piercing member 120). It is to be understood that the components can be the same in function or are similar in function to previously-described components. The adaptor 200 of FIGS. 4A-4B shows certain variations to the adaptor 100 of FIGS. 3A-3J.

As illustrated, the filter 261 of the regulator assembly 150 can be a thin filter (e.g., substantially thinner than the diameter or cross-section of the filter 261). The filter 261 can be hydrophobic and/or antimicrobial. In some embodiments, the filter 261 is configured to engage with a first filter seat 233*a* and a second filter seat 264*a*. One or both of the first filter seat 233*a* and the second filter seat 264*a* can be an annular ridge. For example, the first filter seat 233*a* can be an annular ridge positioned on a stepped portion of the base protrusion 233 of the regulator base 130. The second filter seat 264*a* can be, for example, an annular ridge positioned on a stepped portion of the regulator base 130. In some embodiments, the filter 261 is affixed to the first filter seat 233*a* and/or to the second filter seat 264*a* via an adhesive of other appropriate fixation compound or technique.

The diaphragm 263 can be fixed between the regulator nest 190 and the regulator base 130. In some embodiments, the lip 263*b* of the diaphragm 263 can be positioned or wedged between the axial projection 294 of the regulator nest 190 and a base ridge 264*b*. The base ridge 264*b* can be a generally annular ridge. The lip 263*b* of and/or the entire diaphragm 263 can be constructed from a flexible and/or compressible material. In some embodiments, wedged engagement between the lip 263*b* of the diaphragm 263 and the base ridge 264*b* can reduce, minimize, or eliminate the possibility that fluid will unintentionally bypass the diaphragm 263 around the lip 263*b*.

Figure 5A:
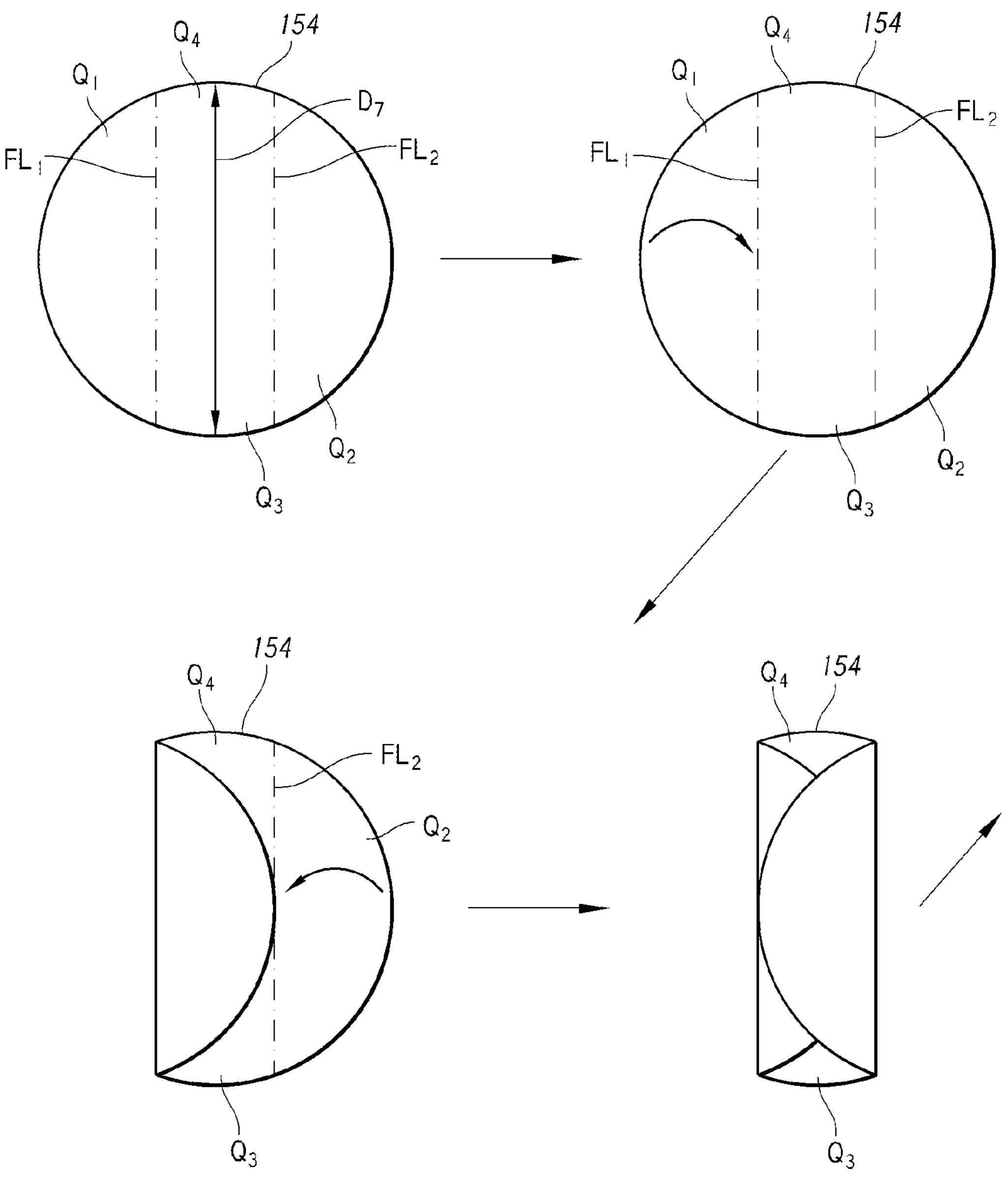
FIG. 5A illustrates an embodiment of a method of folding a flexible enclosure.
Figure 5B:
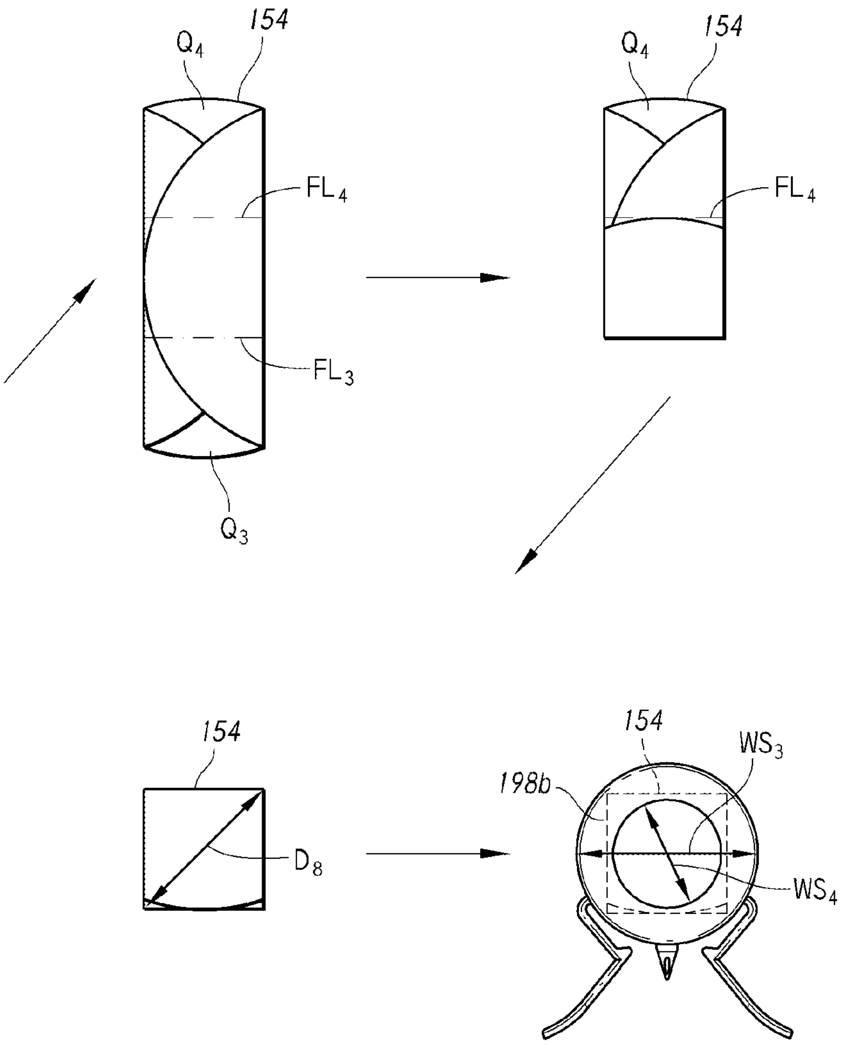
FIG. 5B illustrates steps in an embodiment of the method of FIG. 5A.

FIGS. 5A-5B illustrate an example of a folded flexible enclosure 154 and an example of a method of folding the flexible enclosure 154. In some embodiments, the flexible enclosure 154 can be defined in multiple (e.g., three) horizontal (e.g., left to right with reference to FIG. 5A) portions that have relatively equal horizontal extents. The multiple horizontal portions can be separated by multiple fold lines FL1 and FL2. The method of folding the flexible enclosure 154 can include folding a first portion or quadrant Q1 of the flexible enclosure 154 along the fold line FL1. The method can include folding a second portion or quadrant Q2 over the first portion or quadrant Q1 generally along the fold line FL2. As illustrated in 40B, a method of folding the flexible enclosure 154 can include dividing the flexible enclosure 154 into multiple (e.g., three) vertical portions (e.g., up and down with respect to FIG. 5B). The multiple vertical portions can be separated by another (e.g., a third) fold line FL3 and yet another (e.g., a fourth) fold line FL4. A method of folding the flexible enclosure 154 can include folding another (e.g., a third) portion or quadrant along fold line FL3. Yet another portion (e.g., a fourth) or quadrant Q4 can be folded over the previously formed (e.g., third) portion or quadrant Q3 along fold line FL4. Upon folding quadrant 4 over quadrant 3, as illustrated in FIG. 40B, the flexible enclosure can have a generally square or rectangular shape. The square or rectangle of the flexible enclosure 154 can have a major diagonal line D8. (e.g., a stored or contracted width). The major diagonal line D8 can be less than or about equal to a width WS3 of the regulator nest 190 (e.g., the storage chamber width). As illustrated in FIG. 40B, the diagonal line D8 can be greater than or about equal to the width WS4 of the expansion aperture 128.

Figure 6A:
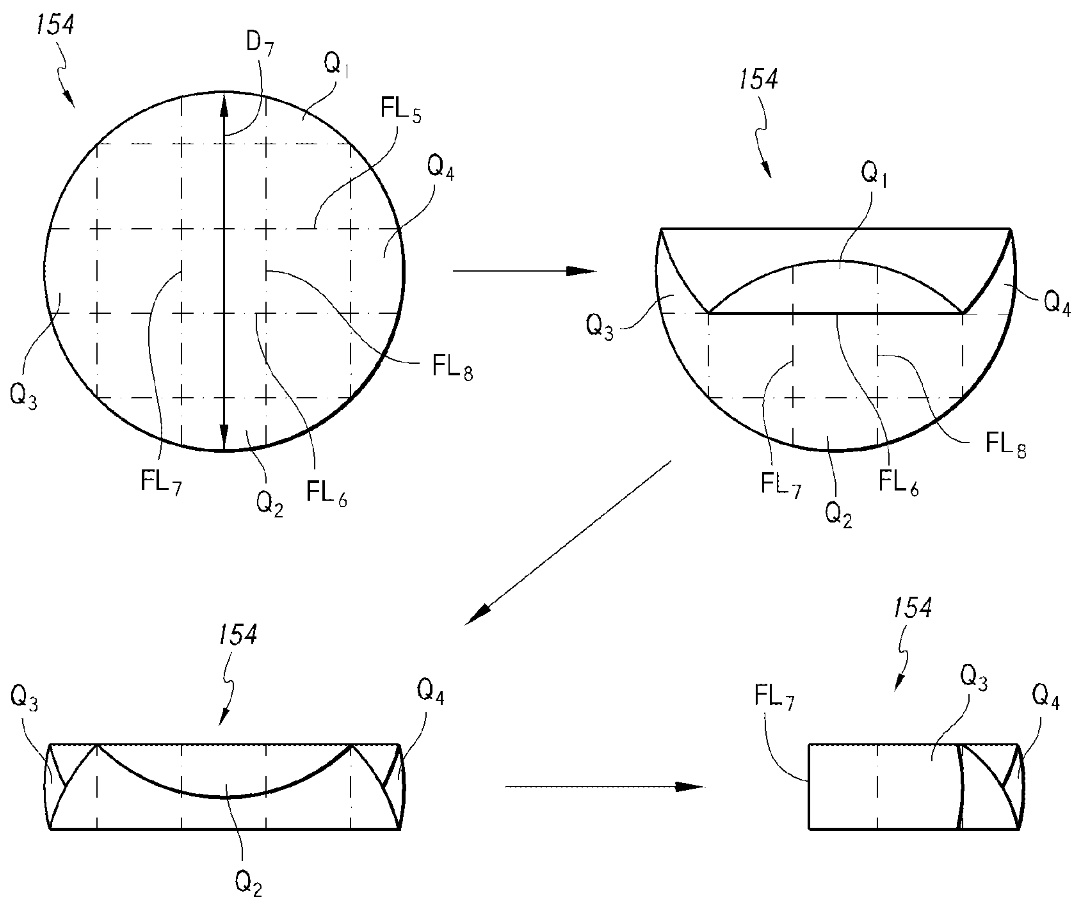
FIG. 6A illustrates an embodiment of a method of folding a flexible enclosure.
Figure 6B:
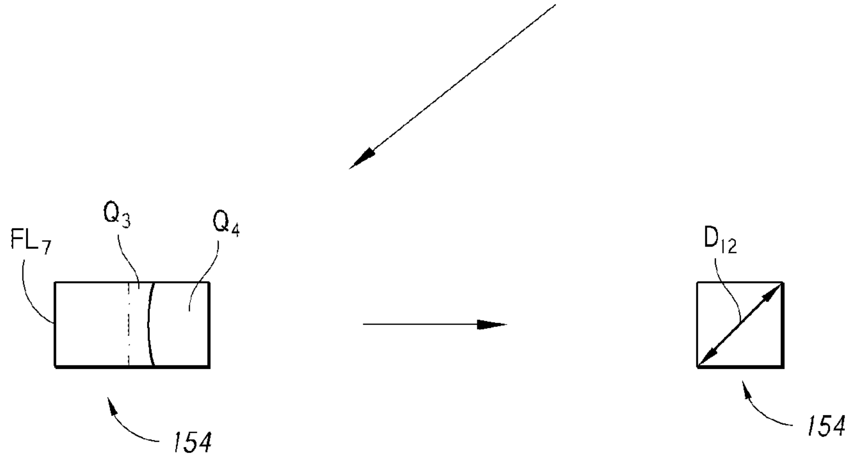
FIG. 6B illustrates steps in an embodiment of the method of FIG. 6A.
Figure 7:
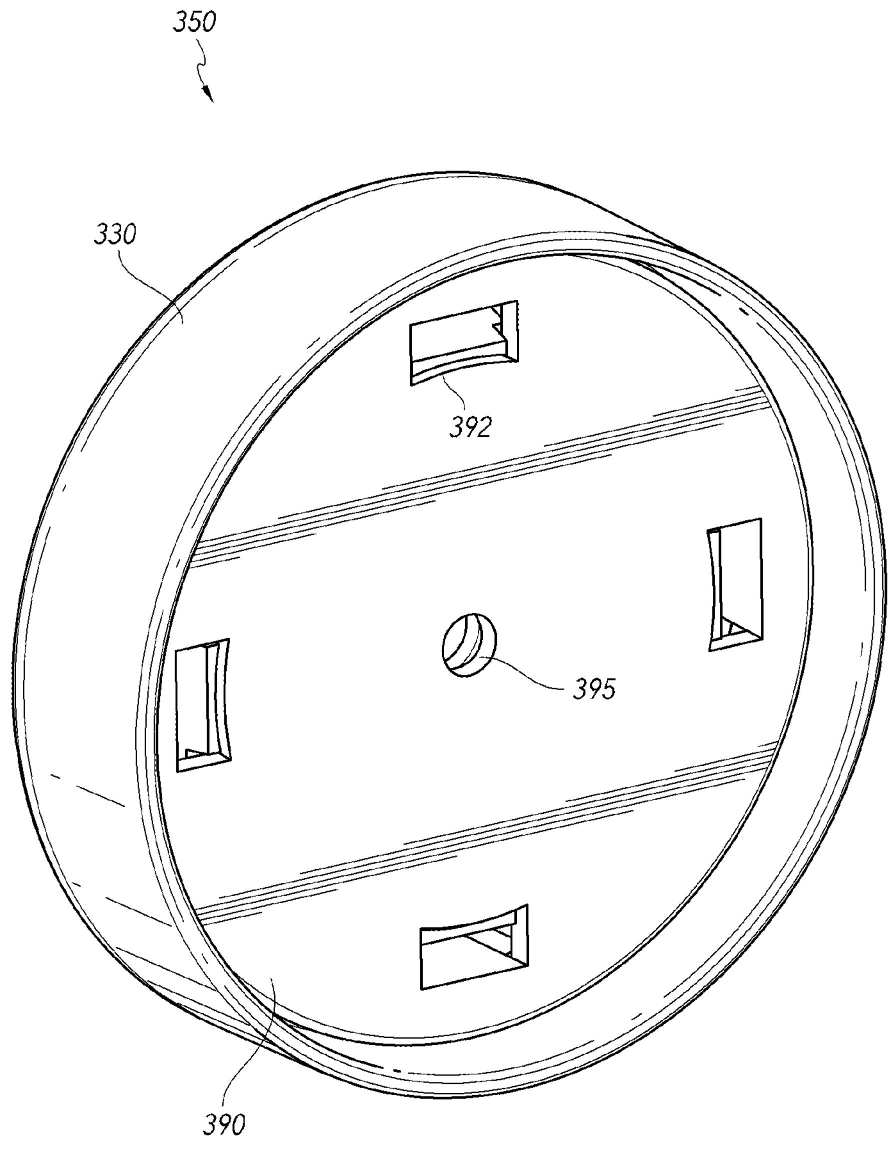
FIG. 7 illustrates a right side perspective view of another embodiment of a regulator assembly without a flexible enclosure.
Figure 8:
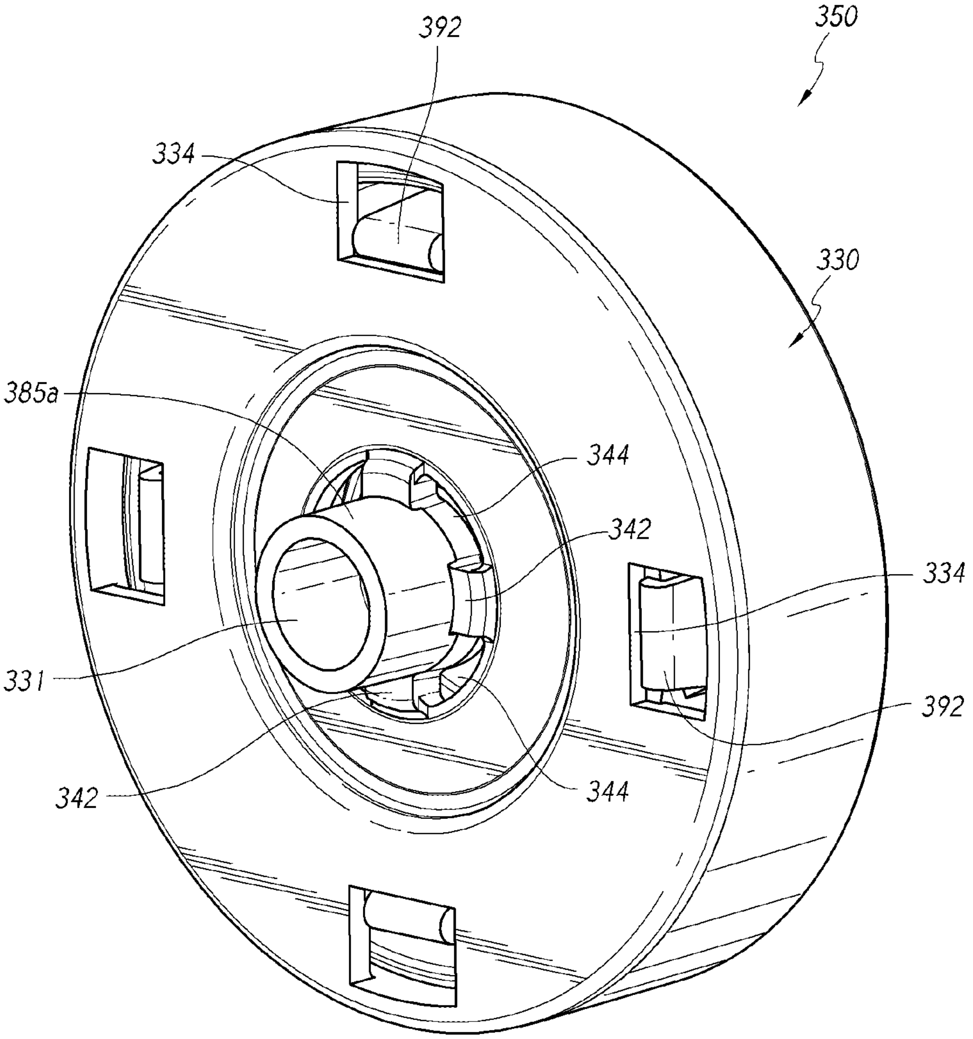
FIG. 8 illustrates a left side perspective view of the regulator assembly of FIG. 7.
Figure 9:
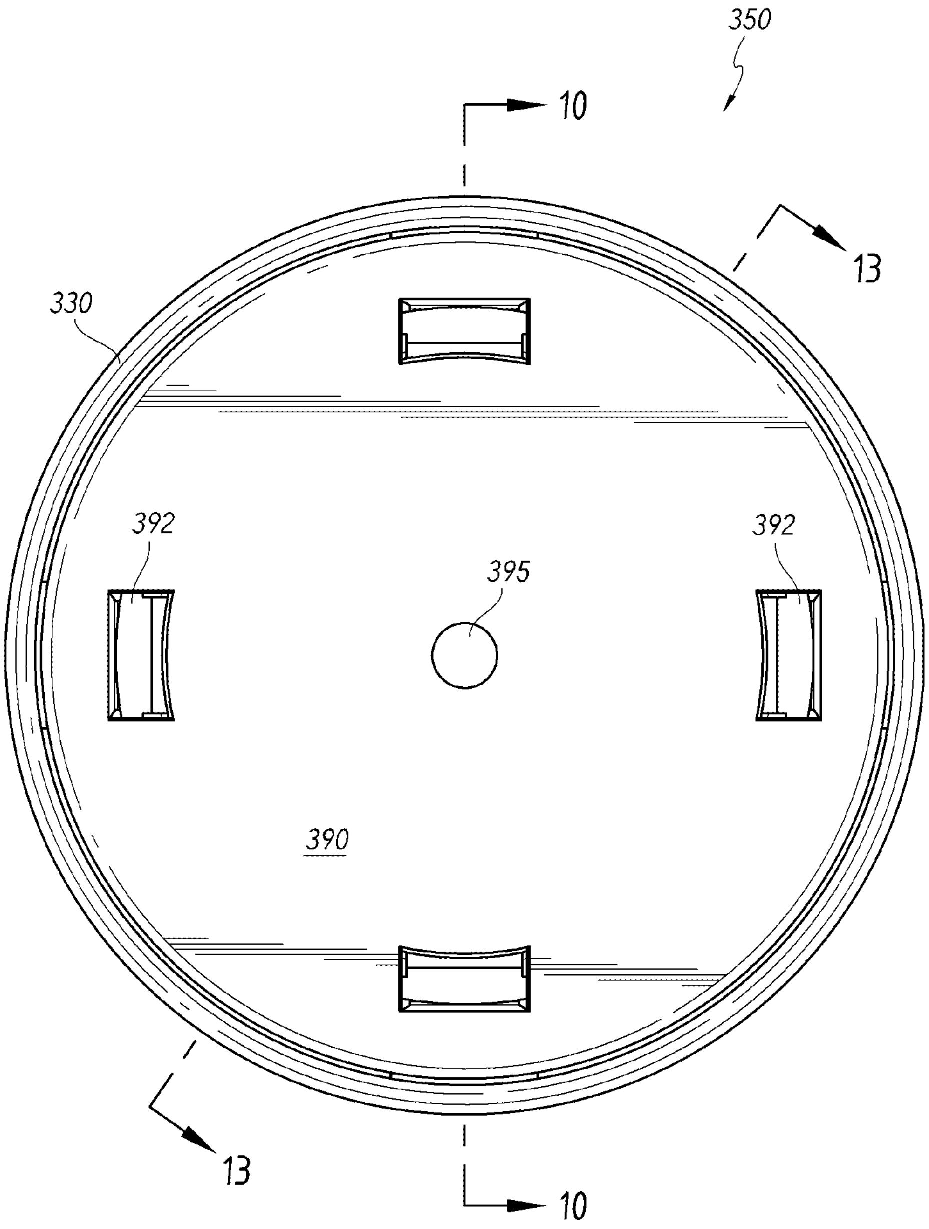
FIG. 9 illustrates a right side plan view of the regulator assembly of FIG. 7 without a flexible enclosure.

FIGS. 6A-6B illustrate a method of folding the flexible enclosure 154. The fold lines of the method illustrated in FIGS. 6A-6B can generally form a square having a diagonal approximately equal to the width D7 of the expanded flexible enclosure 154. The method can include folding a first quadrant Q1*a* of the flexible enclosure 154 toward the second quadrant Q2*a* (e.g., the quadrant on the generally opposite side of the flexible enclosure 154 from the quadrant Q1*a*) along the first fold line FLla. The first quadrant Q1*a* can then be folded back toward the fold line FLla. In some embodiments, the second quadrant Q2*a* is folded over the first quadrant Q1*a* along the second fold line FL2*a*. The second quadrant Q2*a* can then be folded back toward the fold line FL2*a*. The third quadrant Q3*a* may be folded toward the fourth quadrant Q4*a* along the third fold line FL3*a*. According to some configurations, the fourth quadrant Q4*a* is then folded over the third quadrant Q3*a* along the fourth fold line FL4*a*. The generally stacked or laminated third and fourth quadrants Q3*a*, Q4*a* then can be folded along the fifth fold line FL5 to form a substantially rectangular folded flexible enclosure 154 having a diagonal D12. The length of diagonal D12 can be greater than the width WS4 of the expansion aperture 128 and/or less than or equal to about the width WS3 of the regulator nest 130.

FIGS. 7-13 illustrate embodiments of a regulator assembly 350. As with all embodiments in this specification, any structure, feature, material, or step that is illustrated or described in connection with FIGS. 7-13 can be used with or instead of any structure, feature, material, or step that is illustrated or described in any other embodiment in this specification. The vial adaptors and regulator assemblies described in U.S. patent application Ser. No. 14/161,591, filed Jan. 22, 2014 (now published as U.S. Patent Pub. No. 2014/0230932 A1), U.S. Pat. No. 9,132,062, filed Feb. 12, 2014 and issued Sep. 15, 2015, U.S. patent application Ser. No. 14/488,856, filed Sep. 17, 2014 (now published as U.S. Patent Pub. No. 2015/0000787 A1), and U.S. patent application Ser. No. 14/806,520, filed Jul. 22, 2015 are each incorporated by reference in their entirety herein. Any structure, feature, material, or step that is illustrated or described in connection with any embodiment of the foregoing patent applications can be used with or instead of any structure, feature, material, or step that is illustrated or described in any other embodiment in this specification. In some embodiments, the regulator assembly 350 includes a regulator base 330 and a regulator nest 390 configured to fixedly or removably couple with the regulator base 330. Some numerical references to components in FIGS. 7-13 are the same as or similar to those previously described for the regulator assemblies 150 and 250 (e.g., first filter seat 333*a* v. first filter seat 233*a*). It is to be understood that the components can be the same in function or are similar in function to previously-described components. For example, the coupling protrusion 385*a* of the regulator base 330 can be configured to couple with the lumen 126 of the body portion 180 of FIGS. 3A-3J. For example, the coupling portion 385*a* can fit within the lumen 126 and can be connected to the lumen 126 via adhesives, welding, friction-fit, and/or some other connection structure or method. In some embodiments, the coupling portion 385*a* fits around the exterior of the lumen 126 (e.g., the lumen 126 fits within the coupling portion 385*a*). In some embodiments, the regulator assembly 350 is used in combination with a check valve positioned in the regulator channel between the distal regulator aperture 128*a* and the regulator assembly 350. In some embodiments, the regulator assembly 350 is used as part of a system without a check valve positioned between the distal regulator aperture and the regulator assembly 350 (see, e.g., FIGS. 4A-4B). The regulator assembly 350 of FIGS. 7-13 shows certain variations to the regulator assemblies 150 and 250 of FIGS. 3A-6B.

Figure 10:
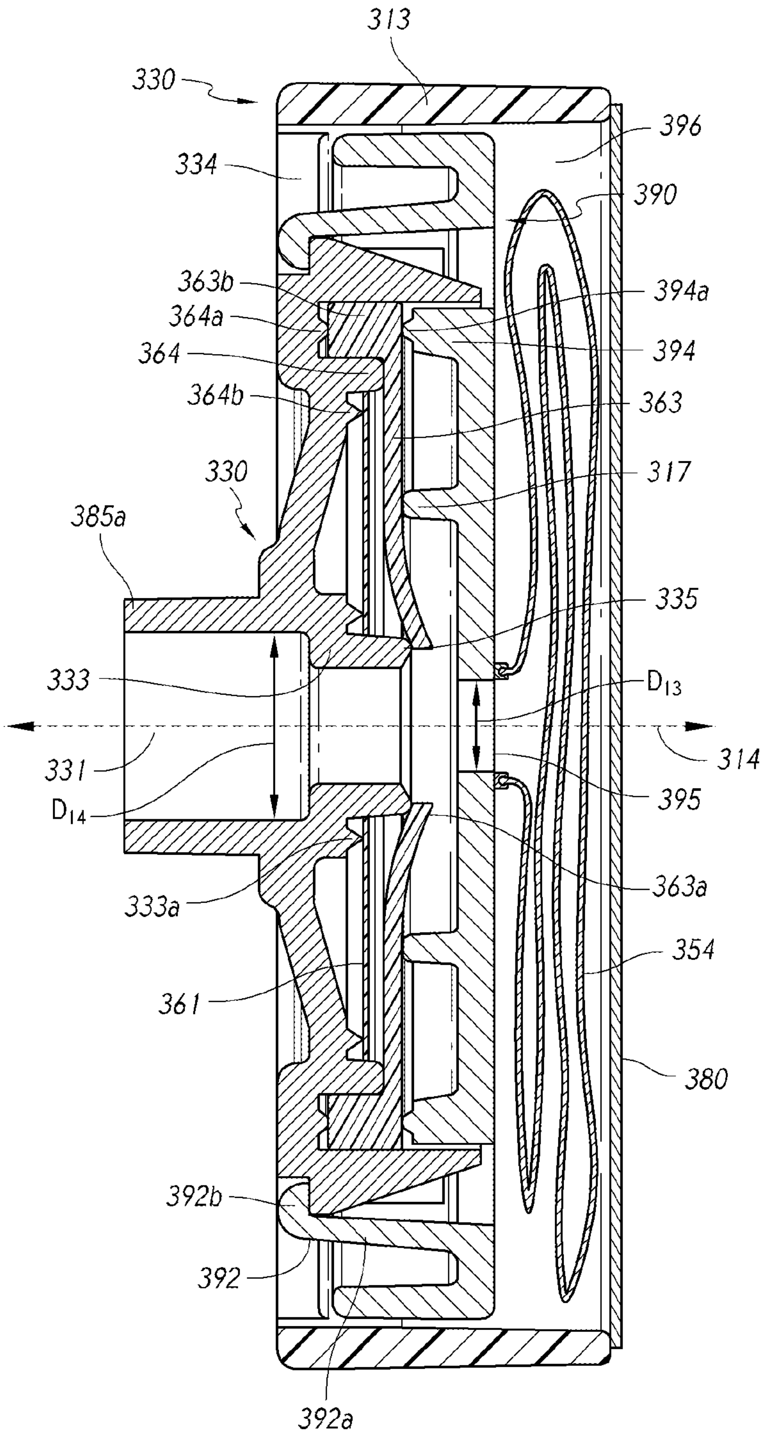
FIG. 10 illustrates a front cross-sectional view of the regulator assembly of FIG. 7 with a flexible enclosure and a cover as viewed along the cut plane 10-10 of FIG. 9.
Figure 10A:
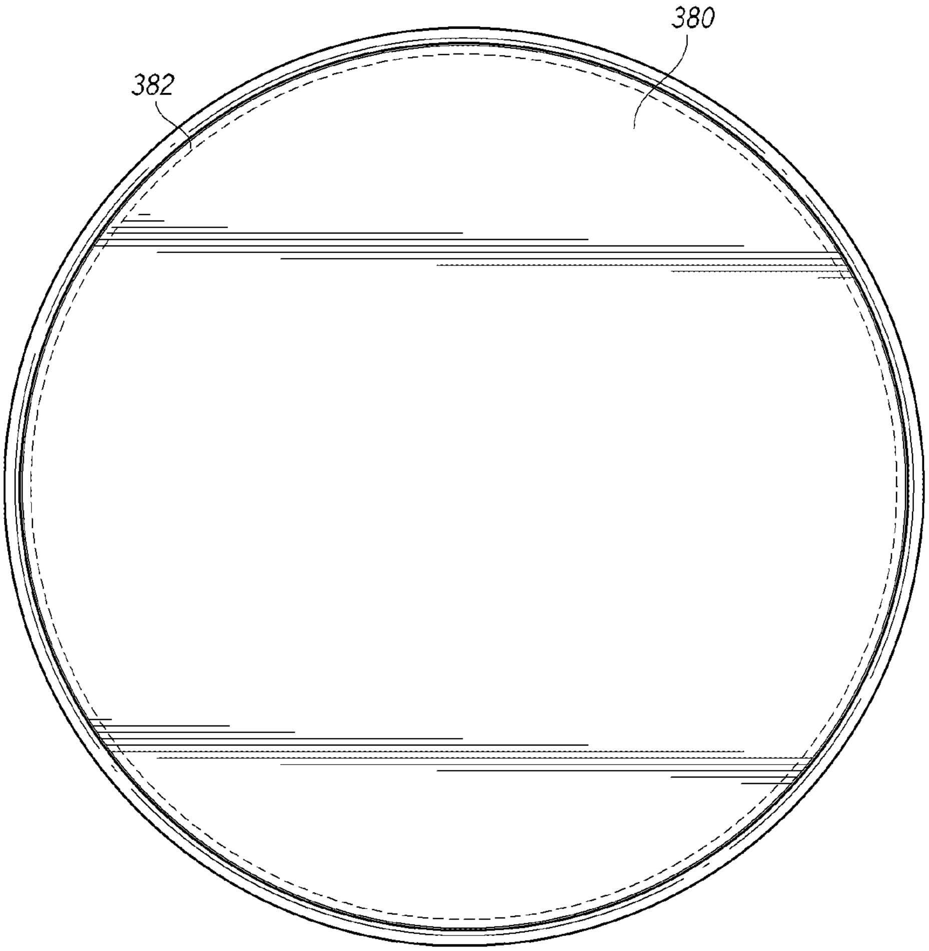
FIG. 10A illustrates a right side plan view of the regulator assembly of FIG. 7 with a perforated cover.

As illustrated in FIG. 10, the regulator base 330 can include an annular wall 313. The annular wall 313 can extend around an outer perimeter of the regulator base 330 (e.g., with respect to a regulator axis 314 of the regulator assembly 350). In some embodiments, the annular wall 313 extends away from the coupling protrusion 385*a* in a direction parallel or approximately parallel to the regulator axis 314. For example, the annular wall 313 can extend beyond the regulator nest 390 when the regulator nest 390 is coupled with the regulator base 330 (see, e.g., FIGS. 7 and 10A). In some embodiments, extending the annular wall 313 beyond the nest 390 can permit attachment of a cover 380 or cap 380*a* to the annular wall 313, as described below. Connecting the cover/cap 380/380*a* to the annular wall 313 can reduce a risk that the regulator nest 390 and regulator base 330 decouple during removal of the cover/cap. The annular wall 313 can define a storage chamber 396 in which the flexible enclosure 354 can be positioned when in a contracted (e.g., stored) configuration, as illustrated in FIG. 10A. In some embodiments, as illustrated, the annular wall 313 can have a seamless or substantially seamless outer surface (e.g., without protrusions, holes, gaps, or other surface features).

Figure 12:
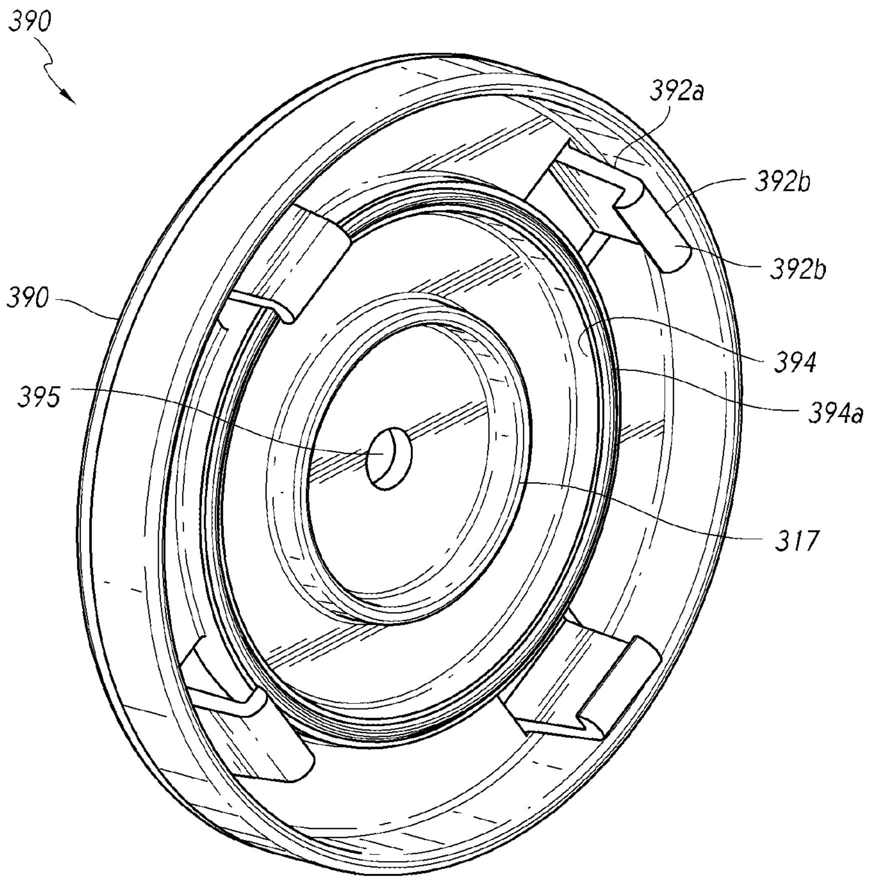
FIG. 12 is a left side perspective view of a regulator nest of the regulator assembly of FIG. 7.

As illustrated in FIGS. 10 and 12, the regulator nest 390 can include one or more protrusions, such as a protrusion 317. The protrusion 317 can have an annular shape. The protrusion 317 can extend from the regulator nest 390 toward the regulator base 330. In some embodiments, the protrusion 317 is positioned radially (e.g., with respect to the regulator axis 314) outward from the nest aperture 395. In some embodiments, the protrusion 317 is positioned radially between the nest aperture 395 and the axial projection 394. In some embodiments, the protrusion 317 is positioned radially inward from the axial projection 394. The protrusion 317 can be sized, shaped, and/or otherwise configured to engage with a portion of the diaphragm 363. For example, the protrusion 317 can contact the diaphragm 363 between the lip 363*b* and inner aperture 363*a* of the diaphragm 363. In some embodiments, the protrusion 317 contacts the diaphragm 363 when the diaphragm is in a closed position, as illustrated in FIG. 10. In some embodiments, the protrusion 317 is separated from the diaphragm 363 when the diaphragm is in the closed position. The protrusion 317 can be configured to bias the diaphragm 363 to the closed position. In some embodiments, the protrusion 317 increases a cracking pressure of the diaphragm 363 (e.g., the pressure differential required to transition the diaphragm from the closed position to an opened position) as compared to an embodiment without the protrusion 317.

The nest aperture 395 can have a diameter D13. In some embodiments, the diameter D13 of the nest aperture 395 is smaller than the diameter D14 of the coupling protrusion 385*a*. For example, the diameter D13 of the nest aperture 395 can be less than or equal to about ¾, less than or equal to about ⅘, less than or equal to about 9/10, less than or equal to about ⅔, less than or equal to about ½, and/or less than or equal to about ¼, of the diameter D14 of the coupling protrusion 385*a*. In some embodiments, the diameter D13 of the nest aperture 395 is less than or equal to about 10 mm, less than or equal to about 7 mm, less than or equal to about 5 mm, less than or equal to about 3 mm, less than or equal to about 1 mm, and/or less than or equal to about 0.5 mm. Many variations are possible.

As illustrated in FIG. 10, a cover 380 can be connected to the regulator assembly 350. For example, the cover 380 can be connected to the annular wall 313. The cover 380 can be configured to inhibit accidental deployment (e.g., transition from contracted to expanded state of the flexible enclosure 354) or partial deployment (e.g., movement of at least a portion of the flexible enclosure 354 from within the nest 390 to outside of the nest 390). In some embodiments, the cover 380 maintains a uniform, compact profile and appearance to assist in transportation and storage, and reduces the risk of damage to or contamination of the flexible enclosure 354 prior to use of the regulator assembly 350.

The cover 380 can be liquid and/or gas-impermeable. In some embodiments, the cover 380 is constructed from coated paper, silicone, polymer(s), foils, Mylar® film, and/or some other suitable material. In some embodiments, the cover 380 is constructed from polyolefin, polyvinyl chloride, polyethylene, polypropylene, and/or a multi-layer polymer composition. In some embodiments, the cover 380 is constructed from a copolymer such as, for example, ethylene propylene or ethylene vinyl acetate. In some embodiments, the cover 380 is constructed from an extruded material, a co-extruded material, a laminate, and/or a biaxially oriented polypropylene. The cover material can be flexible, stretchable, and/or tearable. The cover 380 can be transparent, translucent, or opaque.

The cover 380 can be removably or temporarily coupled to the regulator assembly 350 in any suitable manner, such as adhered, rotated into or onto, screwed into or onto, wrapped, clipped, friction fit, stretched onto, magnetically attached, shrink-wrapped, welded, and/or otherwise attached to the regulator assembly 350 (e.g., to an inside and/or outside surface of the annular wall 313 of the regulator base 330). In some embodiments, the cover 380 includes one or more separable or separating regions configured to easily and predictably produce a separation or split or tear or divide or rupture in the cover when pushed or pulled or influenced by another suitable movement by the user. For example, the one or more separable or separating regions can be one or more perforations or one or more break-away portions. As with all embodiments in this specification, any type of separable or separating region that is illustrated and/or described in this embodiment can be included with or used instead of any structure, feature, material, or step of any other embodiment. For example, as illustrated in FIG. 10A, the cover 380 includes an annular perforation 382. The annular perforation 382 can extend around a perimeter of the cover 380 near (e.g., within about 10%, within about 20%, or within about 5% of the radius of the cover 380) the outer edge of the cover 380. The annular perforation 382 can provide a weakened location on the cover 380 configured to be more easily torn and/or punctured than other portions of the cover 380.

Figure 10B:
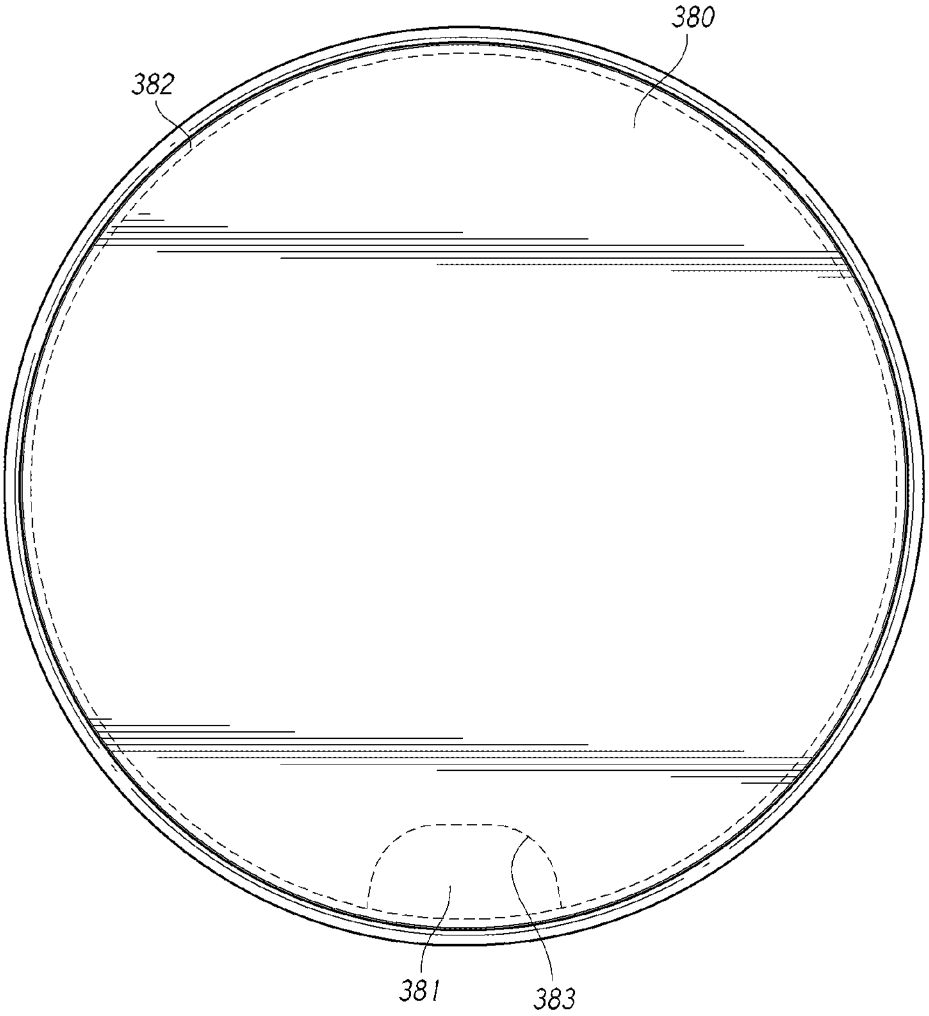
FIG. 10B illustrates a right side plan view of the regulator assembly of FIG. 7 with a perforated cover having a weakened portion.

As illustrated in FIG. 10B, the cover 380 can include a localized perforation 383. The localized perforation 383 can be used in addition to or instead of the annular perforation 382. In some embodiments the localized perforation 383 forms, alone or in combination with the annular perforation 382, a localized weakened portion 381 of the cover 380. The weakened portion 381 of the cover 382 can be configured to be removed, punched-through or otherwise moved or oriented or manipulated to facilitate removal of the cover 380 from the regulator assembly 350 and/or to facilitate uncovering of the flexible enclosure 354, or to create or move or orient a tab to assist in removal of the cover 380. In some embodiments (not shown) a tab or other graspable structure is attached to the weakened portion 381 to facilitate pulling and/or tearing of the weakened portion 381.

Figure 10C:
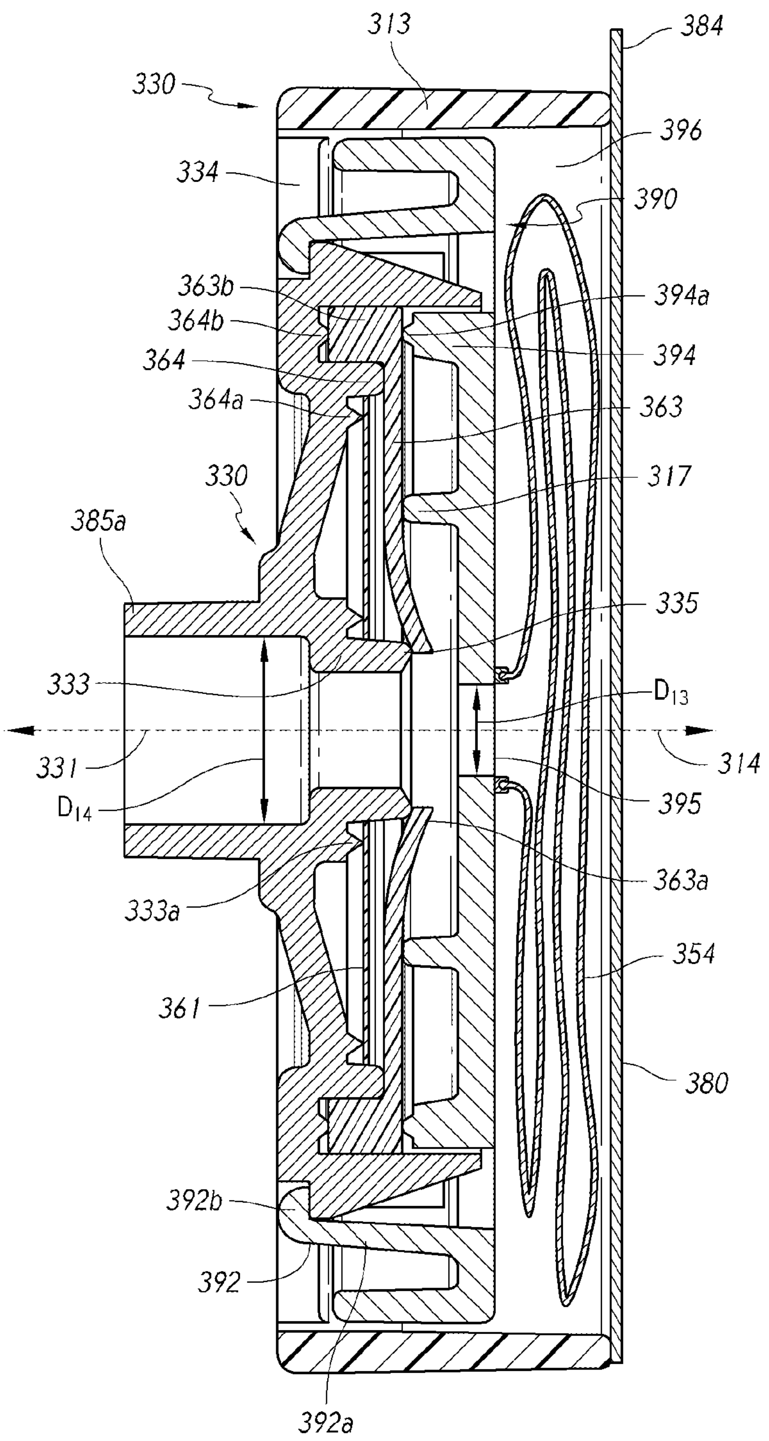
FIG. 10C illustrates a front cross-sectional view of the regulator assembly of FIG. 7 with a flexible enclosure and a cover having a tab, as viewed along the cut plane 10-10 of FIG. 9.
Figure 10D:
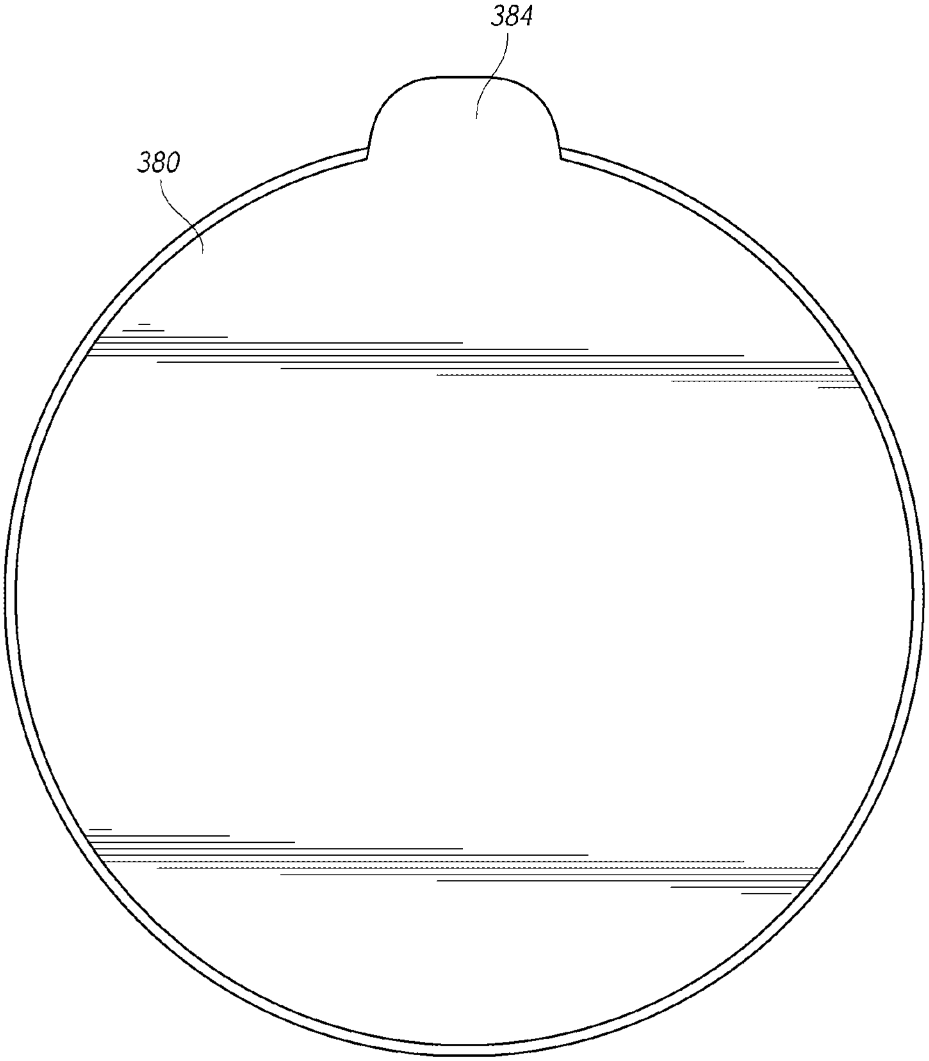
FIG. 10D illustrates a right side plan view of the regulator assembly of FIG. 7 with a flexible enclosure and the cover of FIG. 10C.

As illustrated in FIGS. 10C and 10D, the cover 380 can include a tab 384 or other gripping portion. The tab 384 can be configured to be grasped by a user of the regulator assembly 350. The tab 384 can be configured to facilitate easier removal (e.g., peeling away) of the cover 380 from the regulator base 330. In some embodiments, the tab 384 is used in addition to or instead of a perforation. In some embodiments, as illustrated, the tab 384 extends outward from an outer perimeter of the cover 380. In some embodiments, the tab 384 is attached to the cover 380 at least partially within the perimeter of the cover 380. The tab 384 can be configured to be grasped and pulled in a direction away from the coupling protrusion 385*a* of the regulator assembly 350.

Figure 10E:
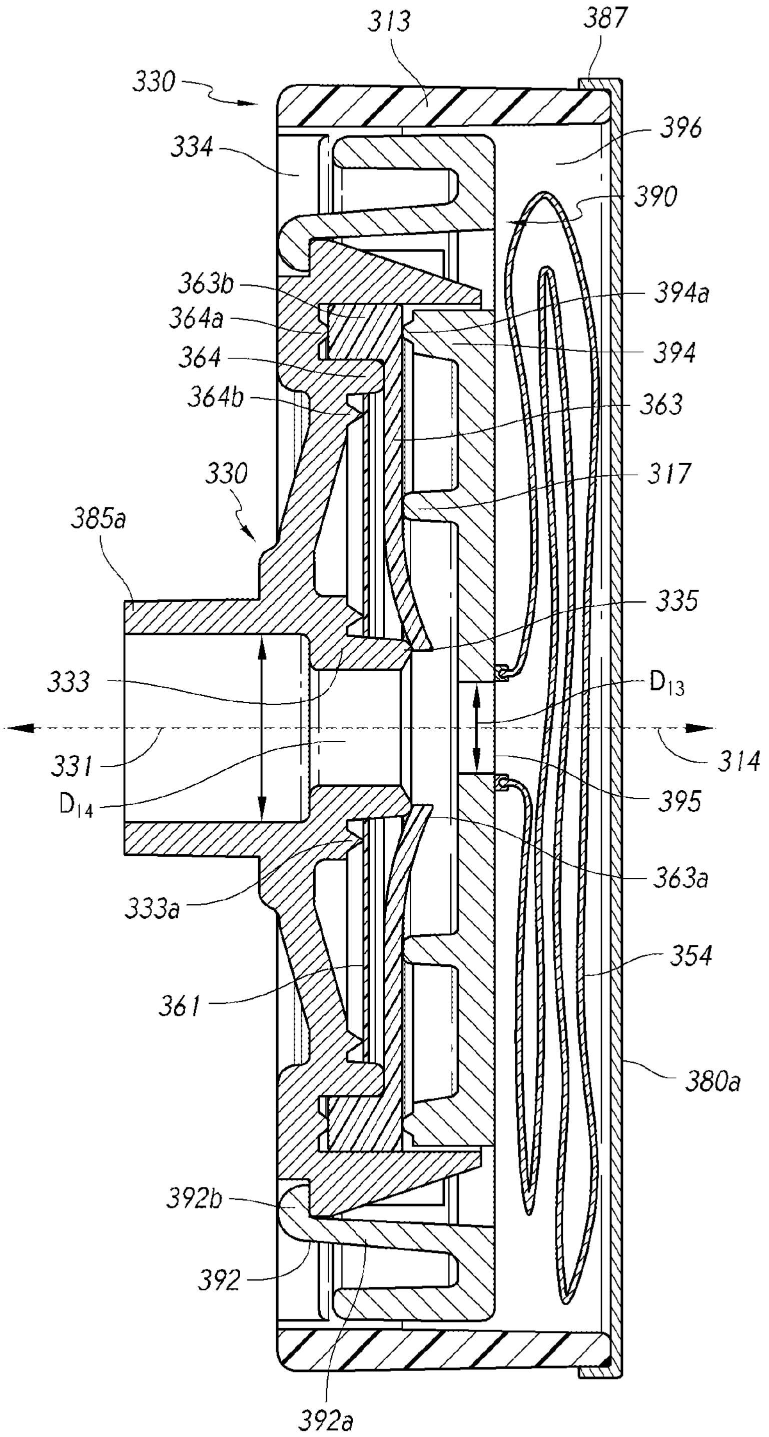
FIG. 10E illustrates a front cross-sectional view of the regulator assembly of FIG. 7 with a flexible enclosure and a cap as viewed along the cut plane 10-10 of FIG. 9.
Figure 10F:
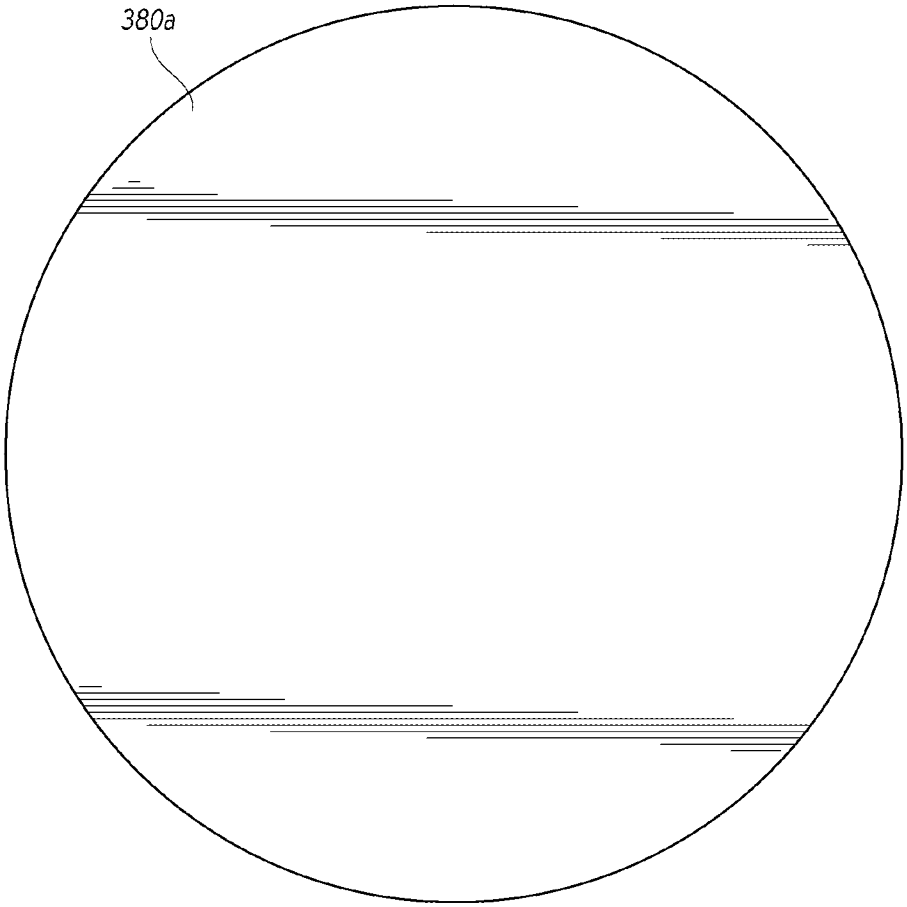
FIG. 10F illustrates a right side plan view of the regulator assembly of FIG. 7 with the cap of FIG. 10E.
Figure 11:
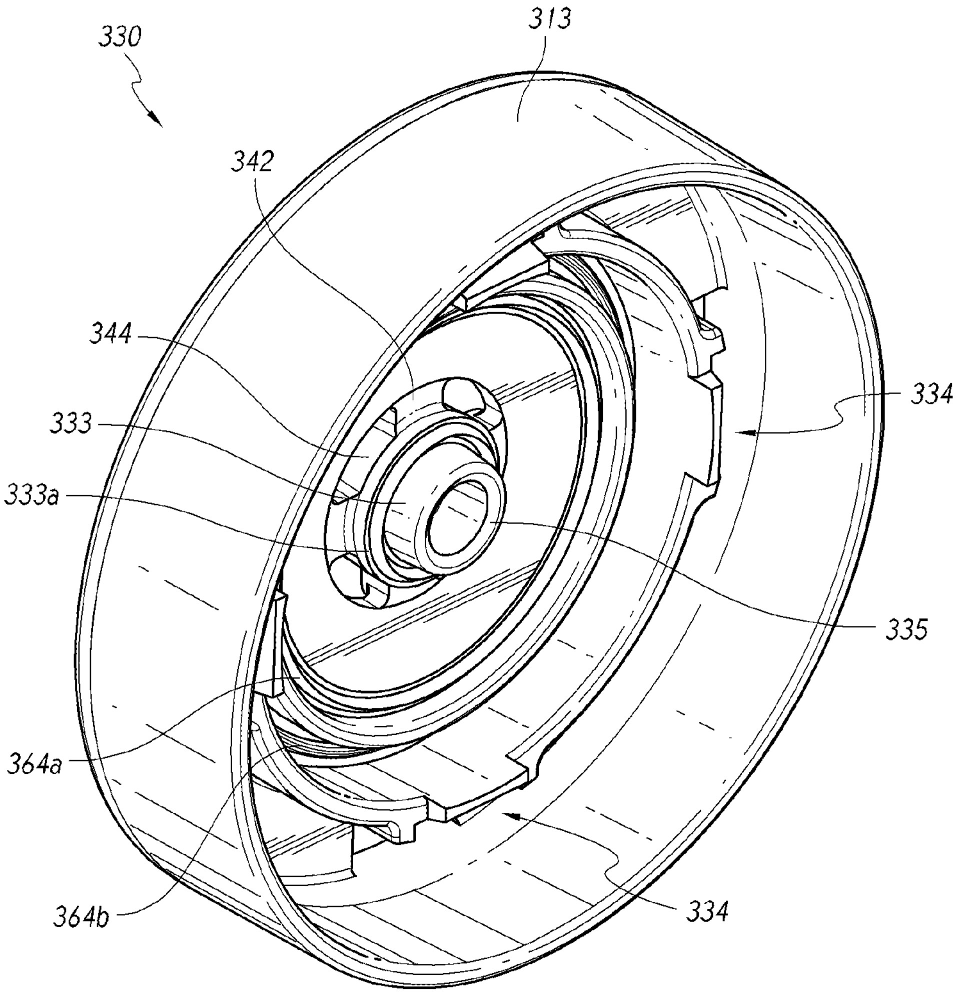
FIG. 11 is a right side perspective view of a regulator base of the regulator assembly of FIG. 7.

As illustrated in FIG. 10E, the regulator assembly 350 can include a cap 380*a* instead of or in addition to a cover 380. The cap 380*a* can be constructed from any of one or more of the same materials recited above for the cover 380, and/or of one or more different materials. In some embodiments, the cap 380*a* includes an annular rim 387. The annular rim 387 can be sized, shaped, and/or otherwise configured to fit around or inside of a portion of the annular wall 313 of the regulator base 330. In some embodiments, the annular wall 313 includes one or more mating features (not shown) configured to engage with the annular rim 387 of the cap 380*a*. For example, the annular wall 313 can include one or more ridges, ribs, protrusions, detents, channels, indentations, and/or other features configured to facilitate mating with the cap 380*a* (e.g., with the annular rim 387 of the cap 380*a*. In some embodiments, the cap 380*a* includes one or more tabs or other structures configured to facilitate gripping of the cap 380*a*. The cap 380*a* can be connected to the annular wall 313 via friction fit, adhesive, heat-shrinking, and/or some other structure and/or method of connection. The cap 380*a* can be configured to inhibit accidental deployment (e.g., transition from contracted to expanded) of the flexible enclosure 354. In some embodiments, the cap 380*a* reduces the risk of damage to the flexible enclosure 354 prior to use of the regulator assembly 350.

Figure 13:
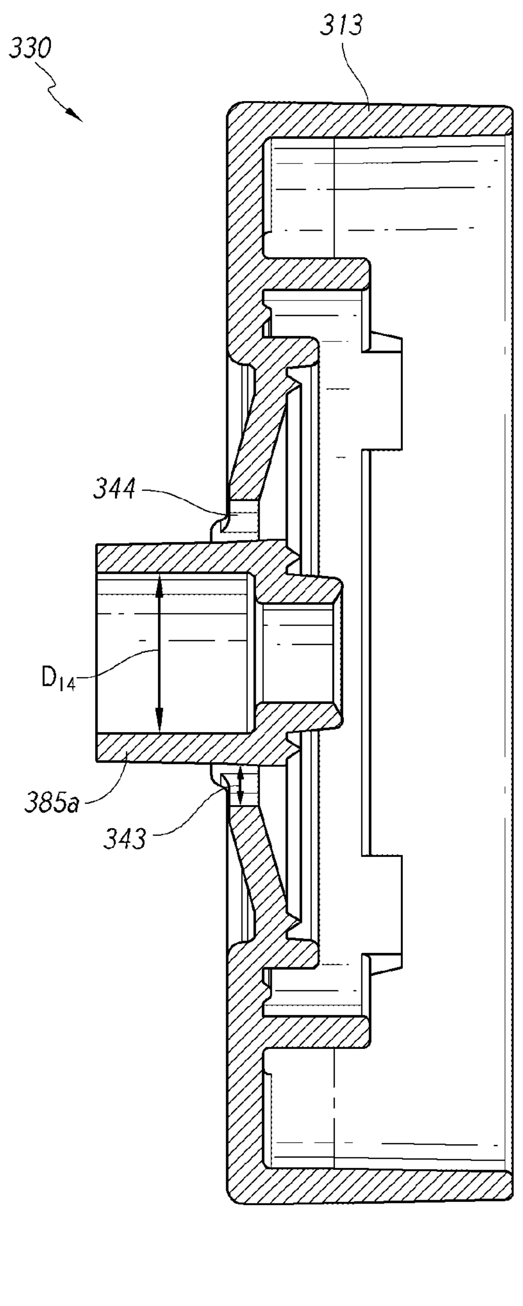
FIG. 13 is a front cross-sectional view of the regulator base of the regulator assembly of FIG. 7, as viewed along the cut plane 13-13 of FIG. 9.
Figure 14:
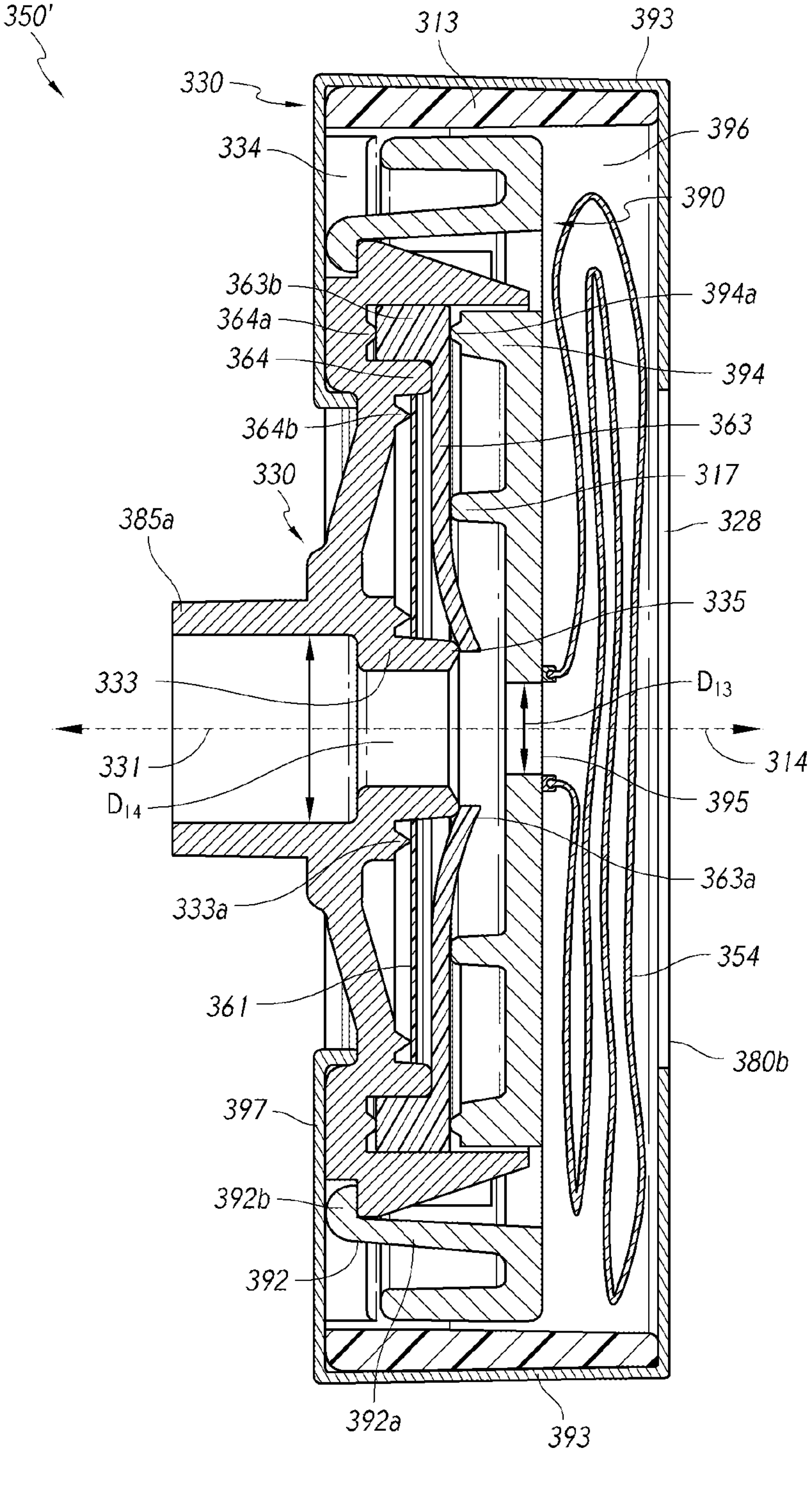
FIG. 14 illustrates a front partial cross-sectional view of another embodiment of regulator assembly of a vial adaptor.

As illustrated in FIG. 13, the regulator assembly (e.g., the regulator base 330) can include one or more intake ports 344. The intake ports 344 can function in a manner similar to or the same as the intake ports 144 described above. The intake ports 344 can have port heights 343 (e.g., as measured perpendicular to the regulator axis 314) greater than or equal to about: 1/20, 1/10, 1/5, 1/4, and/or 1/3 of the diameter D14 of the coupling protrusion 385*a*.

A method of using the regulator assembly 350 can include intentionally removing or modifying the cover 380 or cap 380*a* by a user prior to injection of fluid through the connector interface (e.g., into the vial) or permitting the expanding or moving flexible enclosure 354 to automatically remove or modify the cover 380 in a manner to permit or facilitate further expansion or movement of the flexible enclosure 354. According to some methods, the cover 380 or cap 380*a* is removed prior to withdrawal of fluid through the connector interface. According to some methods, the cover 380 or cap 380*a* is merely loosened or widened or stretched to permit further expansion or movement of the flexible enclosure 354, but the cover 380 or cap 380*a* essentially remains in place. In some embodiments, the flexible enclosure 354 cannot be inflated to a volume beyond that of the storage chamber 396 prior to removal of the cover or cap 380*a*. For example, the cap 380*a* or cover 380 can be configured to prevent expansion of the flexible enclosure 354 out of the storage chamber 396 under normal operating conditions prior to removal of the cap 380*a* or cover 380 from the regulator assembly 350. In some embodiments, after removal or modification of the cap 380*a* or cover 380, fluid can be injected through the connector interface 140. Injection of fluid through the connector interface 140 into a vial can drive or urge fluid through the regulator channel and into the flexible enclosure 354. The flexible enclosure 354 and diaphragm 363 can be configured to operate in any of the one or more steps or manners of the flexible enclosures 154, 254 and diaphragms 163, 263 described elsewhere in this specification (e.g., after the cap or cover 380*a*, 380 is removed). In some embodiments, the cap or cover 380*a*, 380 is configured to be removed only via deliberate user actions such as, for example, pulling of a tab of the cap or cover, tearing of a portion of the cap or cover, and/or otherwise removing the cap or cover from the regulator assembly 350. In some embodiments, the cap or cover 380*a*, 380 is configured to remain in place in the absence of the deliberate user actions described herein (e.g., the cap or cover can be configured to remain connected to the regulator assembly 350 in response to injection of fluid into the vial). The action of removing a cover is used herein in its broad and ordinary sense and includes, for example, having a user pull at least a portion of the cover off the adaptor, having a user rip at least a portion of the cover, inflating the flexible enclosure to cause removal of at least a portion of the cover, inflating the flexible enclosure to tear at least a portion of the cover, causing a perforated portion of the cover to separate, and/or any combination of these actions.

FIGS. 14-17 illustrate embodiments of a regulator assembly 350' that can have components or portions that are the same as or similar to the components or portions of other regulator assemblies disclosed herein. For example, many of the components of the regulator assembly 350' are the same as and have identical reference numbers to those components described above with respect to the regulator assembly 350. As with all embodiments in this specification, any structure, feature, material, or step that is illustrated and/or described in connection with FIGS. 14-17 can be used with or instead of any structure, feature, material, or step that is illustrated and/or described elsewhere in this specification.

The regulator assembly 350' can utilize a cover 380*b*. The cover 380*b* can be configured to wrap around or otherwise cover a substantial portion or a majority of the outer surface area of the regulator base 330 and/or regulator nest 390. In some embodiments, the cover 380*b* includes an annular side portion 393 sized and shaped to fit around a radially-outward portion (e.g., with respect to the regulator axis 314) of the regulator base 330. In some embodiments, the side portion 393 of the cover 380*b* is configured to cover an outer surface of the annular wall 313 of the regulator base 330.

The regulator base 380*b* can include a rear flange 397. The rear flange 397 can be connected to and/or integral with the side portion 393 of the cover 380*b*. The rear flange 397 can wrap around the regulator base 330 (e.g., the annular wall 313) on the side of the base 330 nearest the coupling protrusion 385*a*. In some embodiments, the rear flange 397 extends radially inward toward the regulator axis 314 from the side portion 393 of the cover 380*b*.

As illustrated in FIGS. 14-17, the cover 380*b* can include an aperture 328. The aperture 328 can be positioned on a side of the cover 380*b* opposite the coupling protrusion 385*a*. The aperture 328 can have a width (e.g., diameter) D15. The width D15 of the aperture 328 can be less than a width (e.g., diameter) D16 of the regulator assembly 350'. In some embodiments, the width D15 of the aperture 328 is less than or equal to about ⅔, less than or equal to about ¾, less than or equal to about ⅗, less than or equal to about ½, greater than or equal to about ¼, greater than or equal to about ⅓, greater than or equal to about ⅕, and/or greater than or equal to about 3/10 of the width D16 of the regulator assembly 350'. In some embodiments, the width D15 of the aperture 328 is between about 3/10 and about ½ of the width D16 of the regulator assembly 350'. In some embodiments, the width D15 of the aperture 328 is approximately ⅖ of the width D16 of the regulator assembly 350'. Many variations are possible.

The cover 380*b* can be constructed from a flexible and/or stretchable material. For example, the cover 380*b* can be constructed from polyethylene or from some other material. The cover 380*b* can be constructed from multiple layers. In some embodiments, one or more of the layers of the cover 380*b* is constructed from a material different from the material of one or more other layers.

Figure 15:
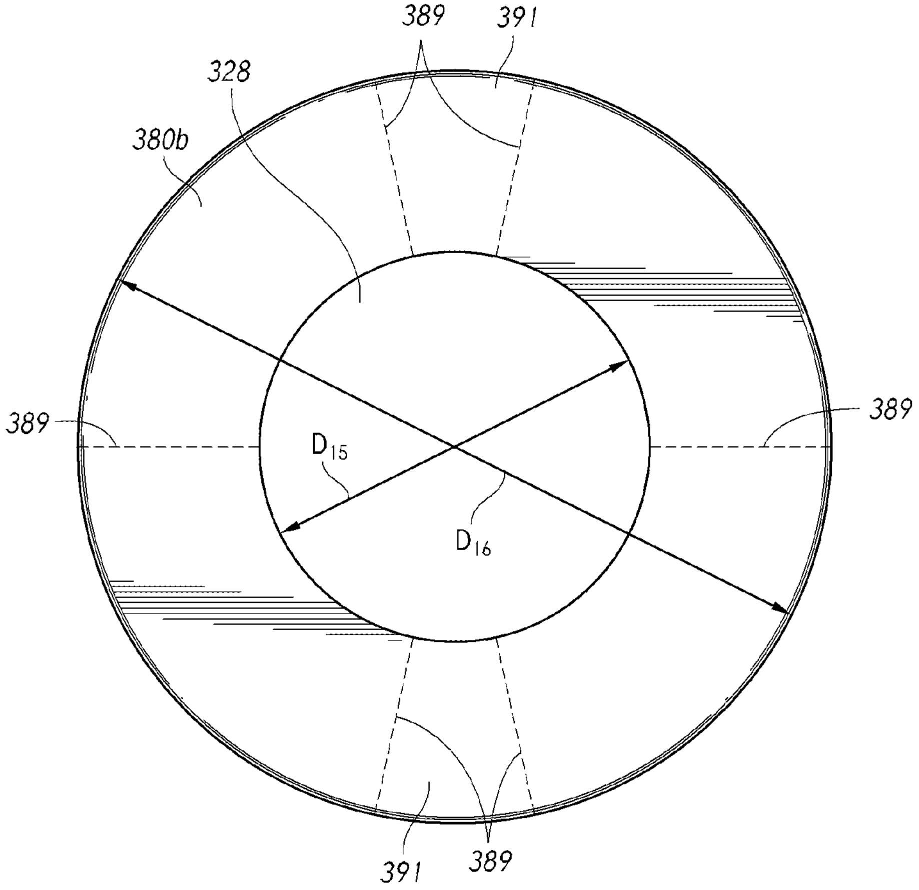
FIG. 15 is a right side plan view of the regulator assembly of FIG. 14, having a cover with a plurality of perforated portions.
Figure 16:
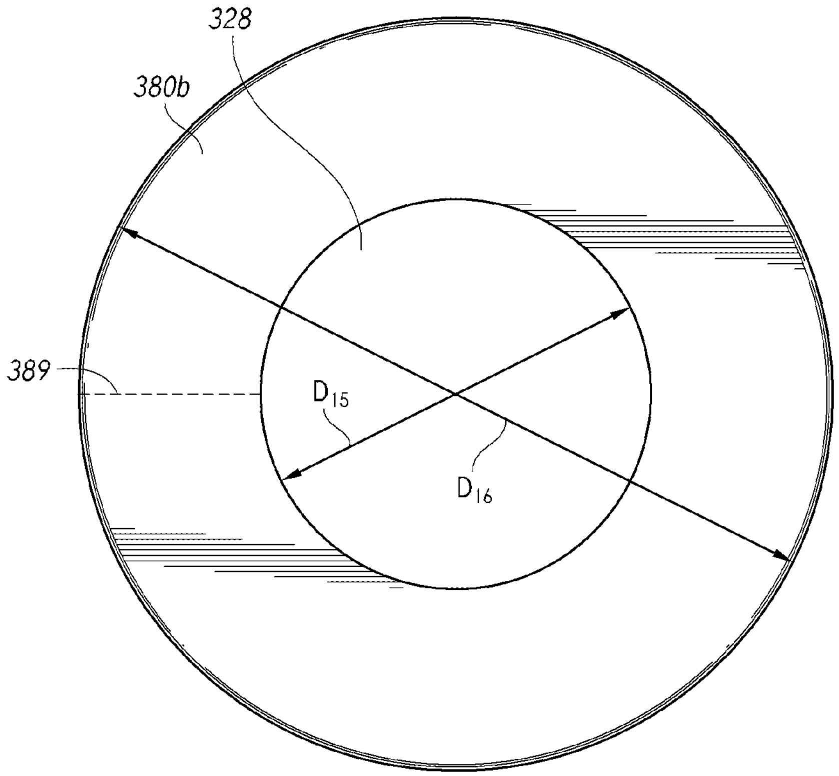
FIG. 16 is a right side plan view of the regulator assembly of FIG. 14, having a cover with a single perforated portion.
Figure 17:
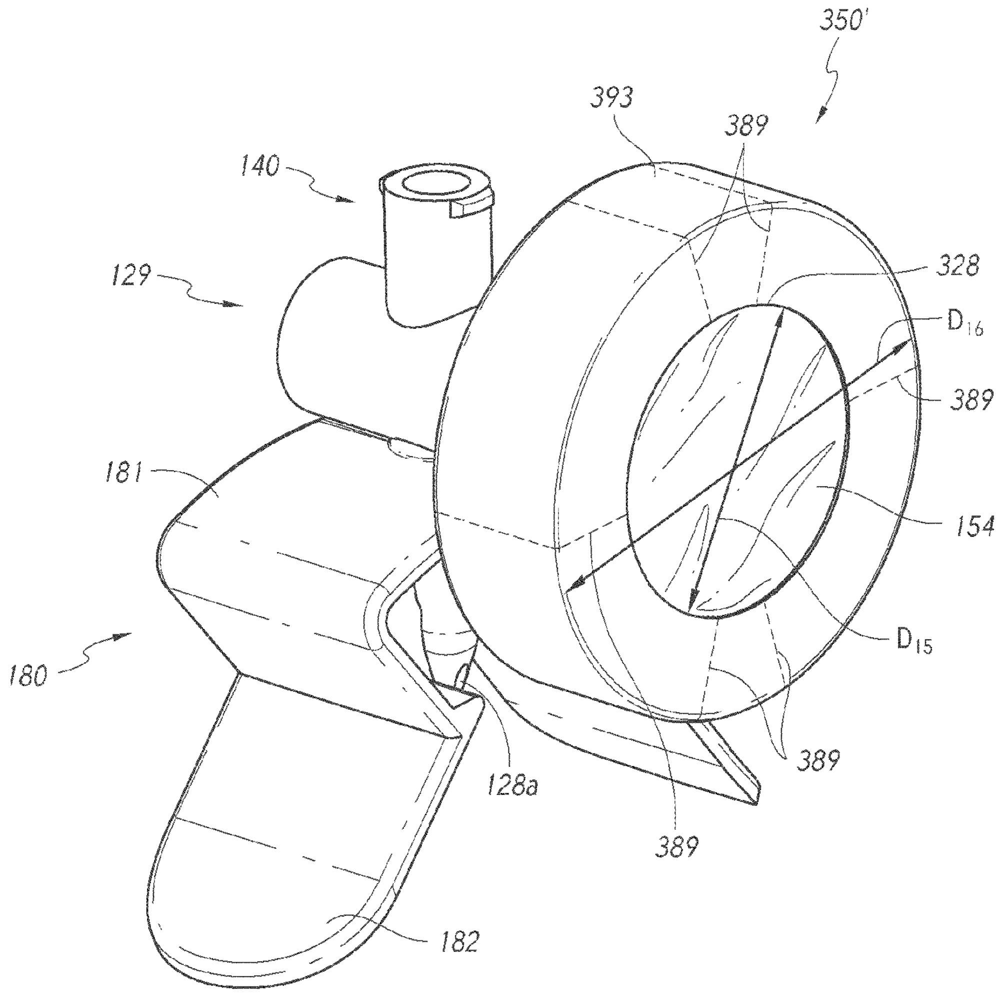
FIG. 17 is a perspective view of a vial adaptor including the regulator assembly of FIG. 14.

The cover 380*b* can include one or more weakened portions configured to tear at a lower stress than the unweakened portions of the cover 380*b*. For example, as illustrated in FIG. 15, the cover 380*b* can include one or more perforations 389. In some embodiments, the cover 380*b* includes only a single perforation 389 (see, e.g., FIG. 16)). The weakened portions/perforations 389 can extend through every layer of the cover 380*b* or through less than all of the layers of the cover 380*b*. The weakened portions 389 of the cover 380*b* can be configured to facilitate tearing of the cover 380*b* during inflation of the flexible enclosure 354. For example, the weakened portions 389 can facilitate tearing of the cover 380*b* to allow for expansion of the flexible enclosure 354 out from the cover 380*b*. The weakened portions 389 can be configured to resist tearing during manufacture, assembly, and shipment of the regulator assembly 350'.

In some embodiments, the perforations 389 extend from the aperture 328 toward the side portion 393 of the cover 380*b*. In some embodiments, the perforations 389 extend through the side portion 393 and/or through all or part of the rear flange 397 of the cover 380*b* (see, e.g., FIG. 17).

As illustrated in FIG. 15, two or more perforations 389 can be positioned close to each other to form one or more pull or break-away perforated segments 391. In some embodiments, the perforated segments 391 can be pulled, broken away, moved or modified, and/or torn away from the remainder of the cover 380*b* prior to or during inflation of the flexible enclosure 354.

A method of using a vial adaptor utilizing the regulator assembly 350' can include connecting the vial adaptor to a vial. This step can include piercing the vial with a piercing member of the vial adaptor. A syringe or other fluid source may be connected to a connector interface of the vial adaptor. Fluid can be injected into the vial via the connector interface and the piercing member. Injection of the fluid into the vial can increase pressure within the vial. Increased pressure within the vial can force fluid through a regulator channel of the regulator assembly 350' into the flexible enclosure 354. The flexible enclosure 354 can expand in response to the introduction of fluid from the vial. Expansion of the flexible enclosure 354 can stress the cover 380*b*. Stress of the cover 380*b* from the expansion of the flexible enclosure 354 can facilitate tearing of one or more of the perforations 389. Tearing of one or more of the perforations 389 can facilitate expansion of the flexible enclosure 354 out from the cover 380*b*.

As used herein, the terms "attached," "connected," "mated," and other such relational terms should be construed, unless otherwise noted, to include removable, moveable, fixed, adjustable, and/or releasable connections or attachments. The connections/attachments can include direct connections and/or connections having intermediate structure between the two components discussed.

The terms "approximately", "about", "generally" and "substantially" as used herein represent an amount close to the stated amount that still performs a desired function or achieves a desired result. Any terms generally associated with circles, such as "radius" or "radial" or "diameter" or "circumference" or "circumferential" or any derivatives or similar types of terms are intended to be used to designate any corresponding structure in any type of geometry, not just circular structures. For example, "radial" as applied to another geometric structure should be understood to refer to a direction or distance between a location corresponding to a general geometric center of such structure to a perimeter of such structure; "diameter" as applied to another geometric structure should be understood to refer to a cross sectional width of such structure; and "circumference" as applied to another geometric structure should be understood to refer to a perimeter region. Nothing in this specification or drawings should be interpreted to limit these terms to only circles or circular structures.

Although the vial adaptor has been disclosed in the context of certain embodiments and examples, it will be understood by those skilled in the art that the vial adaptor extends beyond the specifically disclosed embodiments to other alternative embodiments and/or uses of the embodiments and certain modifications and equivalents thereof. For example, some embodiments are configured to use a regulating fluid that is a liquid (such as water or saline), rather than a gas. As another example, in certain embodiments the bag comprises a bellows. It should be understood that various features and aspects of the disclosed embodiments can be combined with or substituted for one another in order to form varying modes of the vial adaptor. For example, one or more valves, such as the check valve 170, can be positioned in the regulator channels of the valve adaptors described above. Accordingly, it is intended that the scope of the vial adaptor herein-disclosed should not be limited by the particular disclosed embodiments described above, but should be determined only by a fair reading of the claims that follow.

The following is claimed:

1. A method of manufacturing a pressure-regulating vial adaptor, the method comprising:

selecting a body portion comprising a regulator channel extending between a piercing member and a proximal regulator aperture; and coupling a regulator assembly with the regulator channel, the regulator assembly comprising:

a regulator base comprising an annular wall;

a regulator nest being configured to couple with the regulator base;

a flexible enclosure being at least partially positioned within the regulator nest, the flexible enclosure being configured to transition between a stored configuration and an expanded configuration; and a cover being coupled to the regulator base such that the cover at least partially extends along the flexible enclosure, the annular wall, and the regulator nest, the cover comprising an aperture, the cover being further configured to permit the flexible enclosure to at least partially extend through the aperture as the flexible enclosure transitions from the stored configuration towards the expanded configuration, the cover comprising an annular side portion extending along the annular wall and a rear flange extending towards a longitudinal axis of the regulator assembly, such that the cover wraps around at least a portion of the regulator base.

2. The method of claim 1, wherein the annular wall extends around an outer perimeter of the regulator base.

3. The method of claim 1, wherein the annular wall extends beyond the regulator nest such that the cover engages the annular wall.

4. The method of claim 1, wherein the annular wall comprises an outer surface, and wherein the outer surface is seamless.

5. The method of claim 1, further comprising wrapping the cover at least partially around the flexible enclosure, the annular wall, and the regulator nest.

6. The method of claim 1, further comprising adhering the cover to at least one of the annular wall or the regulator nest.

7. The method of claim 1, further comprising covering an outer surface of the regulator base with the annular side portion by fitting the annular side portion around the annular wall of the regulator base.

8. The method of claim 1, wherein the cover is configured to stretch as the flexible enclosure transitions from the stored configuration towards the expanded configuration.

9. The method of claim 8, wherein the cover is further configured to remain coupled to the regulator base when the flexible enclosure transitions from the stored configuration towards the expanded configuration.

10. The method of claim 1, wherein the cover is fluid impermeable.

11. The method of claim 1, further comprising forming the cover from at least one of coated paper, silicone, foil, polyolefin, polyvinyl chloride, polyethylene, polypropylene, a multilayer polymer composition, or a copolymer.

12. The method of claim 1, wherein the cover is transparent.

13. The method of claim 1, wherein the cover is opaque.

14. The method of claim 1, wherein the cover is toroidal.

15. The method of claim 1, wherein the cover comprises a compact profile.

16. The method of claim 1, wherein the aperture comprises an aperture width less than a regulator width of the regulator assembly.

17. The method of claim 16, wherein the aperture width is less than or equal to two-thirds of the regulator width.

* * * * *